(12) United States Patent
Cooper et al.

(10) Patent No.: US 8,969,350 B2
(45) Date of Patent: Mar. 3, 2015

(54) PHARMACEUTICAL PRODUCT COMPRISING A P38 KINASE INHIBITOR AND A SECOND ACTIVE INGREDIENT

(75) Inventors: Anne Elizabeth Cooper, Loughborough (GB); Timothy Jon Luker, Loughborough (GB); Jerzy Andrzej Schmidt, Loughborough (GB)

(73) Assignee: Astrazeneca AB, Sodertalje (SE)

( * ) Notice: Subject to any disclaimer, the term of this patent is extended or adjusted under 35 U.S.C. 154(b) by 442 days.

(21) Appl. No.: 13/140,477

(22) PCT Filed: Dec. 17, 2009

(86) PCT No.: PCT/SE2009/051444
§ 371 (c)(1),
(2), (4) Date: Sep. 14, 2011

(87) PCT Pub. No.: WO2010/071583
PCT Pub. Date: Jun. 24, 2010

(65) Prior Publication Data
US 2012/0028941 A1 Feb. 2, 2012

Related U.S. Application Data

(60) Provisional application No. 61/138,595, filed on Dec. 18, 2008.

(51) Int. Cl.
| | | |
|---|---|---|
| *A61K 31/50* | (2006.01) |
| *A61K 31/501* | (2006.01) |
| *A61K 45/06* | (2006.01) |
| *A61K 31/416* | (2006.01) |
| *A61K 31/444* | (2006.01) |
| *A61K 31/4545* | (2006.01) |
| *A61K 31/4965* | (2006.01) |

(52) U.S. Cl.
CPC .............. *A61K 45/06* (2013.01); *A61K 31/416* (2013.01); *A61K 31/444* (2013.01); *A61K 31/4545* (2013.01); *A61K 31/4965* (2013.01)
USPC ..................................................... 514/252.1

(58) Field of Classification Search
CPC ............ A61K 31/4965; A61K 31/573; A61K 2300/00
USPC ....................................................... 514/252.1
See application file for complete search history.

(56) References Cited

U.S. PATENT DOCUMENTS

2004/0248853 A1    12/2004   Dyckman et al.

FOREIGN PATENT DOCUMENTS

| WO | WO-2007/091176 A1 | 8/2007 |
| WO | WO-2008/057775 A2 | 5/2008 |
| WO | WO 2009/001132    | * 12/2008 |
| WO | WO-2009/001132 A1 | 12/2008 |

* cited by examiner

*Primary Examiner* — Marcos Sznaidman
(74) *Attorney, Agent, or Firm* — Harness, Dickey & Pierce, P.L.C.

(57) ABSTRACT

The invention provides a pharmaceutical product, kit or composition comprising a first active ingredient which is N-Cyclopropyl-3-fluoro-4-methyl-5[3-[[1-[2-[2-(methylamino) ethoxy]phenyl]cyclopropyl]amino]-2-oxo-1(2H)-pyrazinyl]-benzamide or a salt thereof, and a second active ingredient selected from: a non-steroidal Glucocorticoid Receptor (GR Receptor) Agonist; an antioxidant; a β2 adrenoceptor agonist; a CCR1 antagonist; a chemokine antagonist (not CCR1); a corticosteroid; a CRTh2 antagonist; a DPI antagonist; an Histone Deacetylase activator; an IKK2 kinase inhibitor; a COX inhibitor; a lipoxygenase inhibitor; a leukotriene receptor antagonist; a MABA compound; an MPO inhibitor; a muscarinic antagonist; a PDE4 inhibitor; a PPARγ agonist; a protease inhibitor; a Statin; a thromboxane antagonist; a vasodilator; or, an ENAC blocker (Epithelial Sodium-channel blocker); and its use in the treatment of respiratory disease.

1 Claim, 28 Drawing Sheets

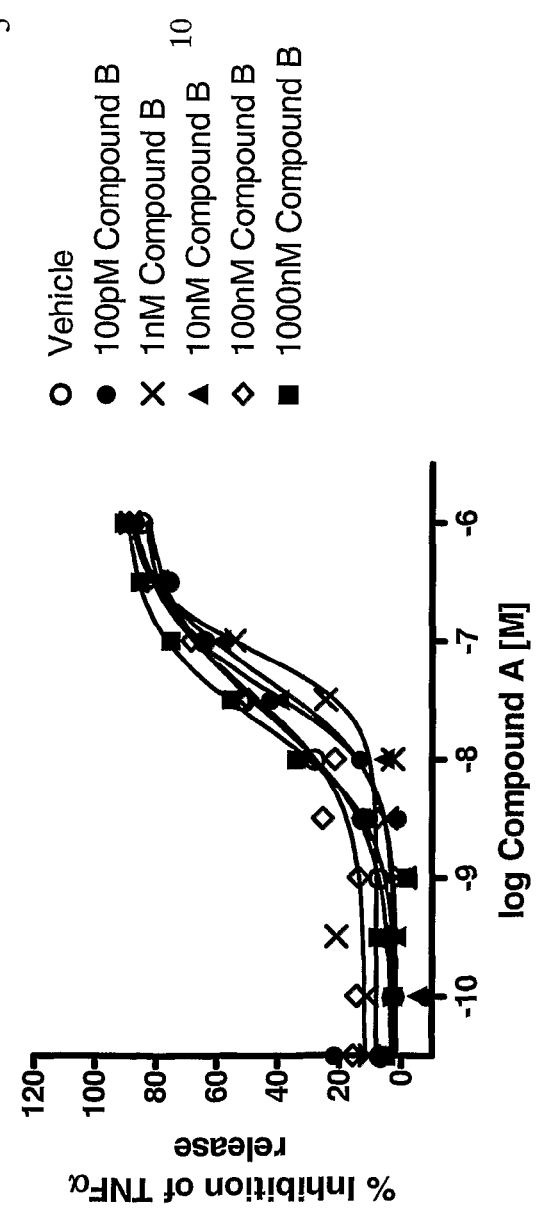
Figure 1: Effect of the combination of Compound A and Compound B on LPS stimulated TNFα production from human PBMC.

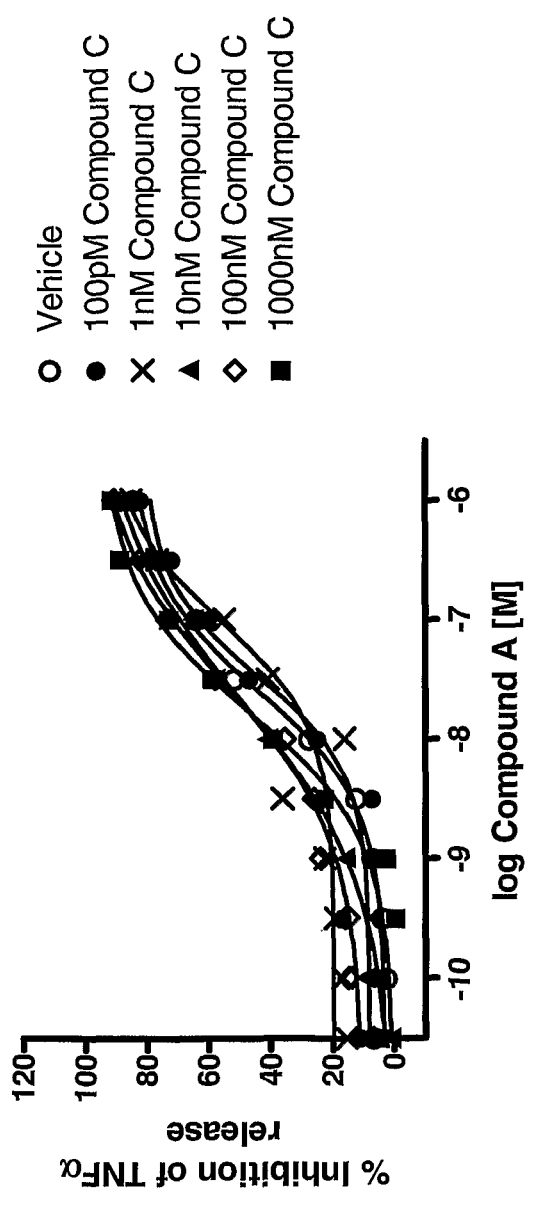
Figure 2: Effect of the combination of Compound A and Compound C on LPS stimulated TNFα production from human PBMC

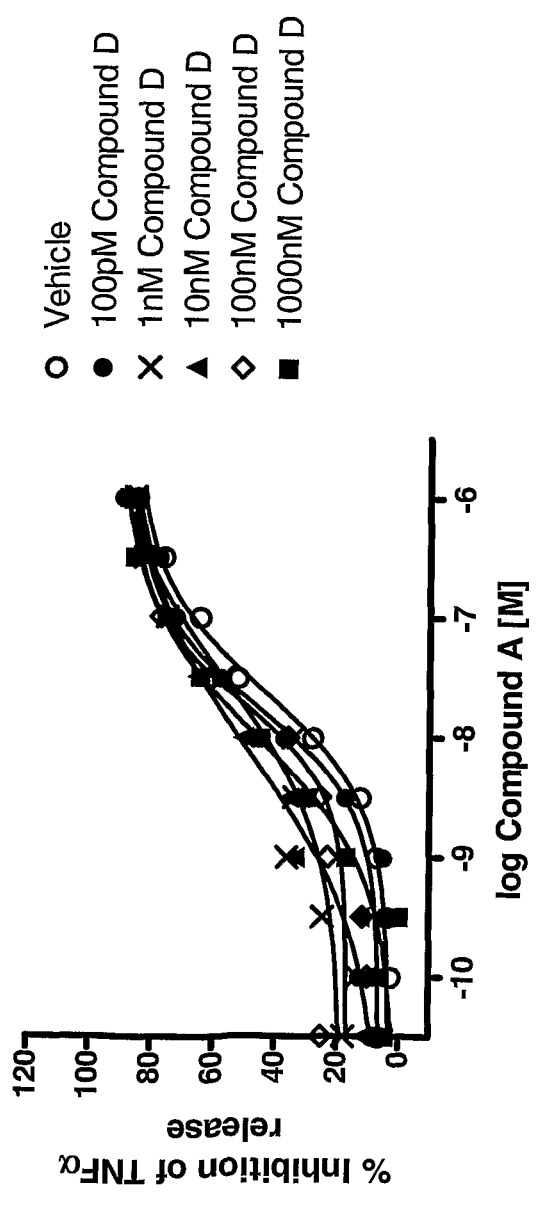
Figure 3: Effect of the combination of Compound A and Compound D on LPS stimulated TNFα production from human PBMC

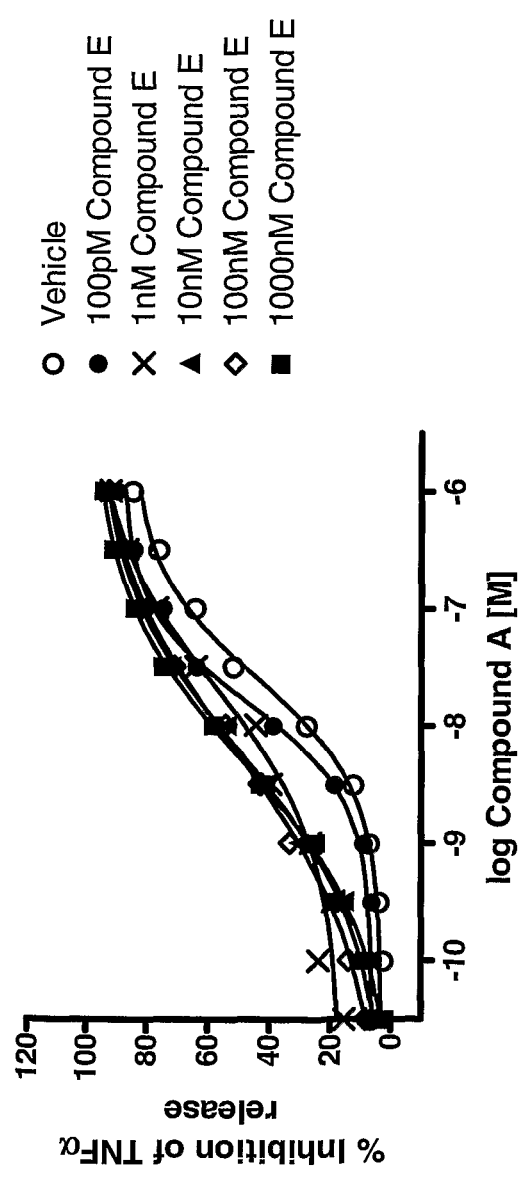
Figure 4: Effect of the combination of Compound A and Compound E on LPS stimulated TNFα production from human PBMC

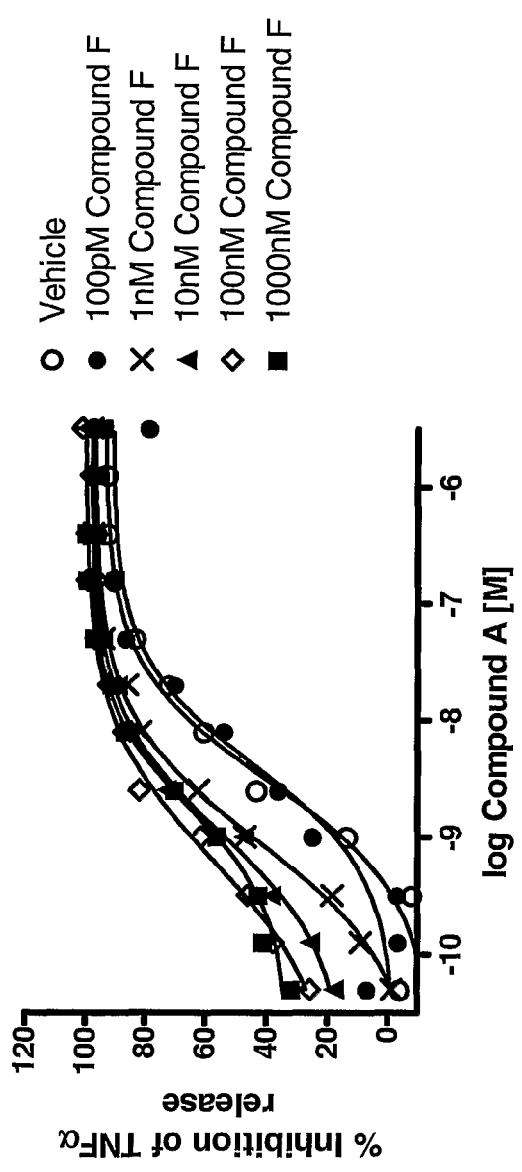
Figure 5: Effect of the combination of Compound A and Compound F on LPS stimulated TNFα production from human PBMC

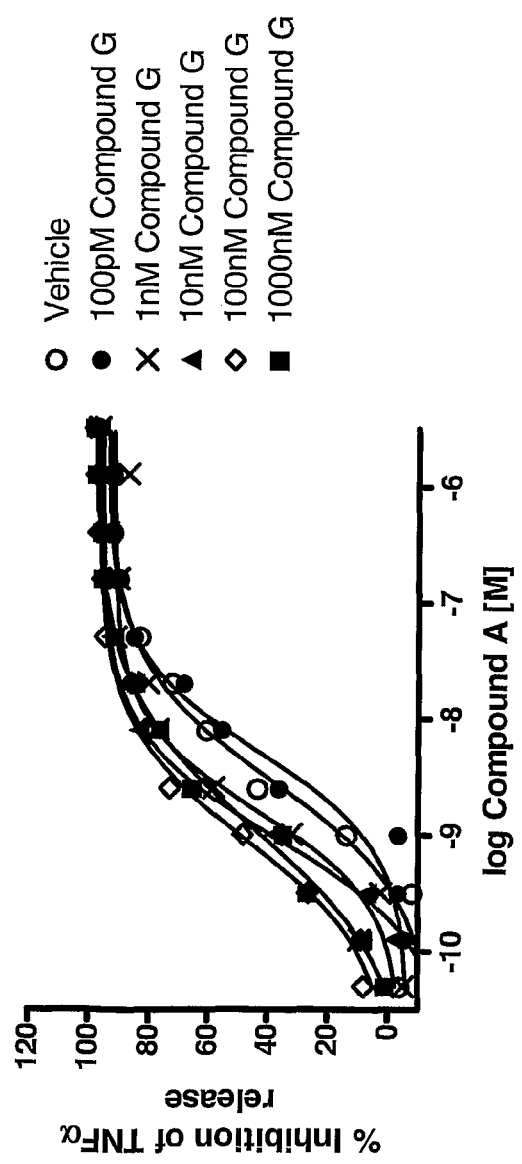
Figure 6: Effect of the combination of Compound A and Compound G on LPS stimulated TNFα production from human PBMC

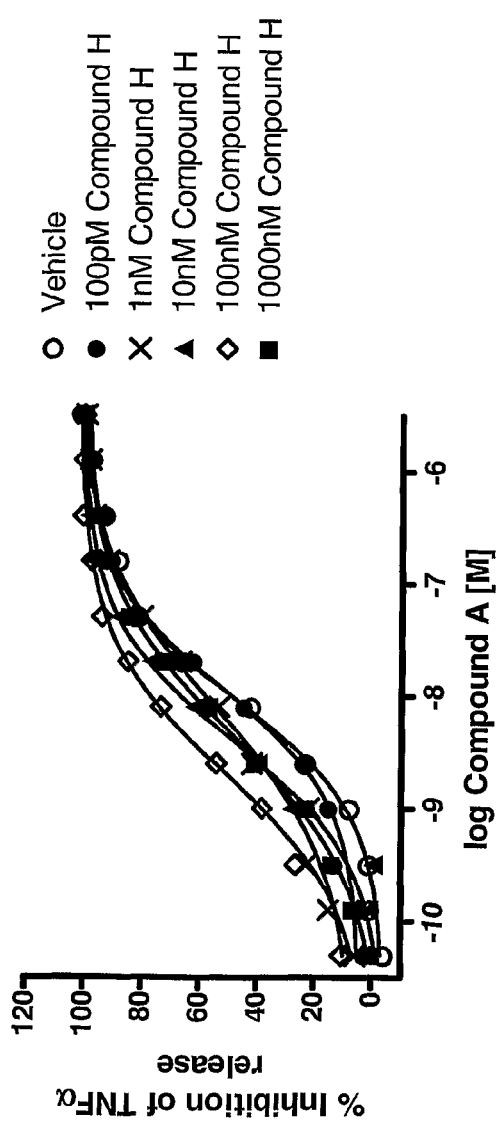
Figure 7: Effect of the combination of Compound A and Compound H on LPS stimulated TNFα production from human PBMC

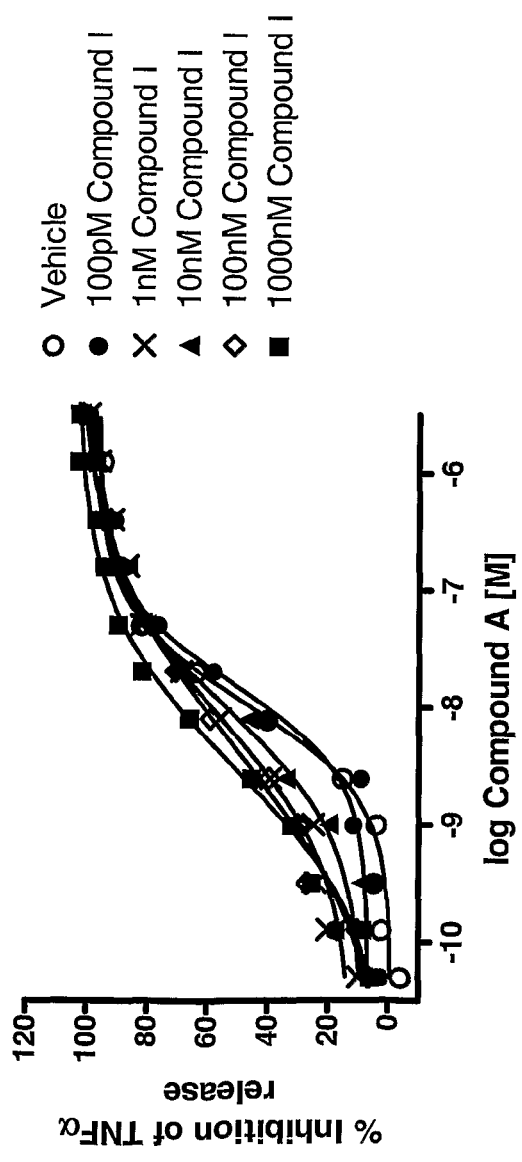
Figure 8: Effect of the combination of Compound A and Compound I on LPS stimulated TNFα production from human PBMC

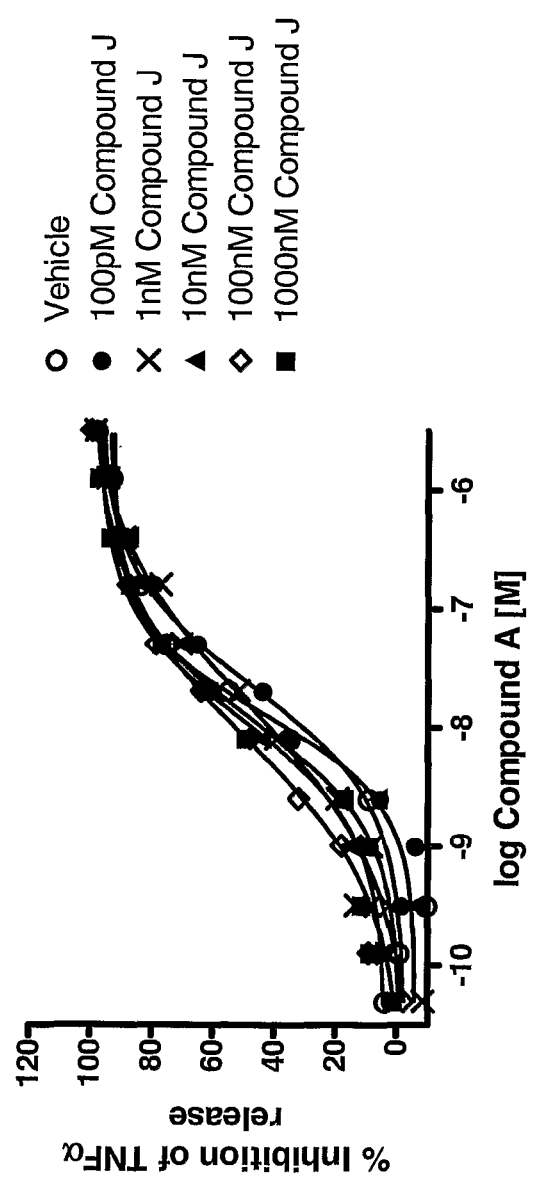
Figure 9: Effect of the combination of Compound A and Compound J on LPS stimulated TNFα production from human PBMC

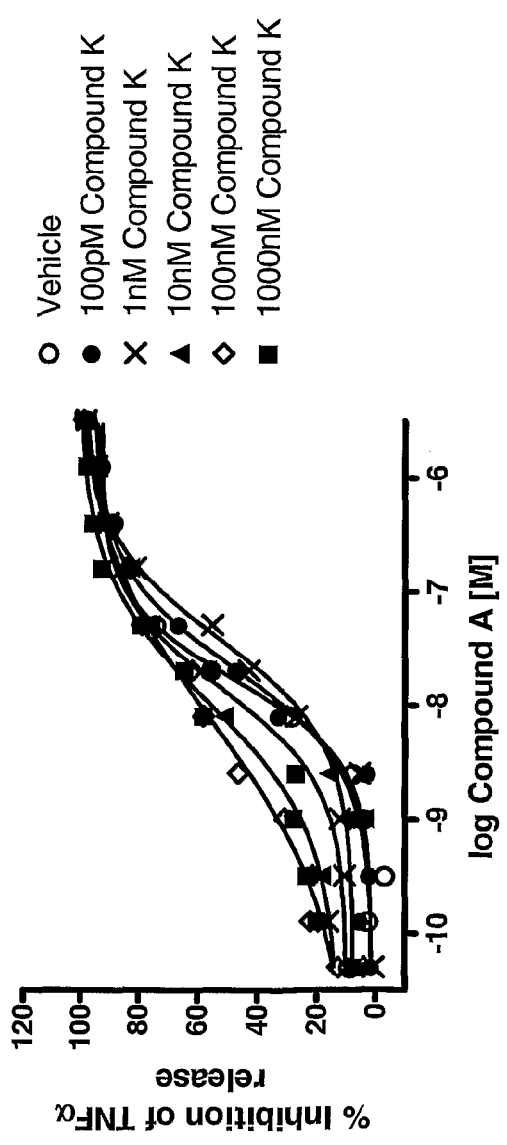
Figure 10: Effect of the combination of Compound A and Compound K on LPS stimulated TNFα production from human PBMC

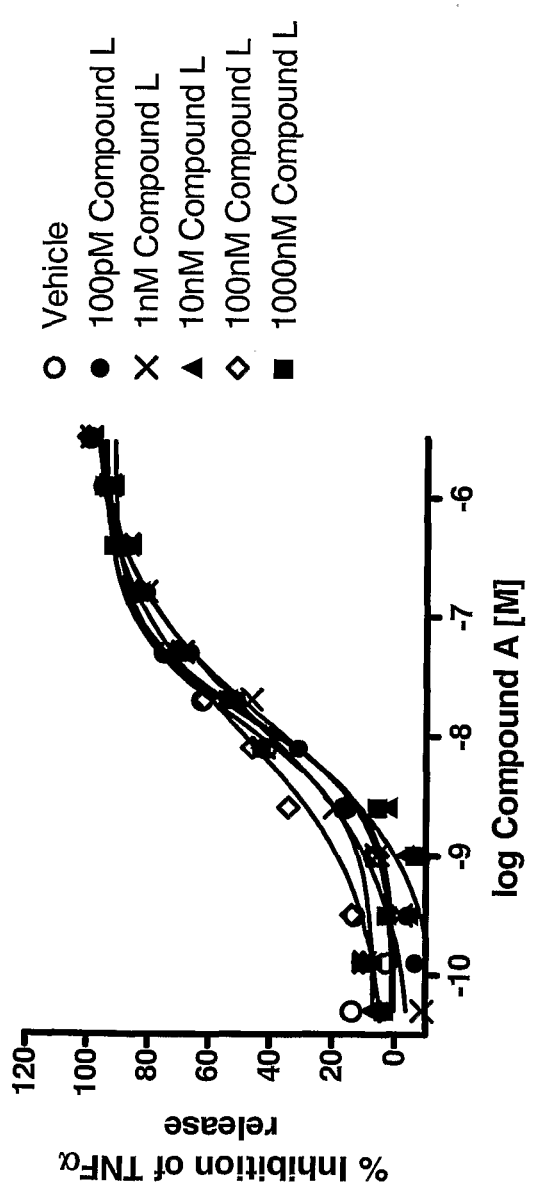
Figure 11: Effect of the combination of Compound A and Compound L on LPS stimulated TNFα production from human PBMC

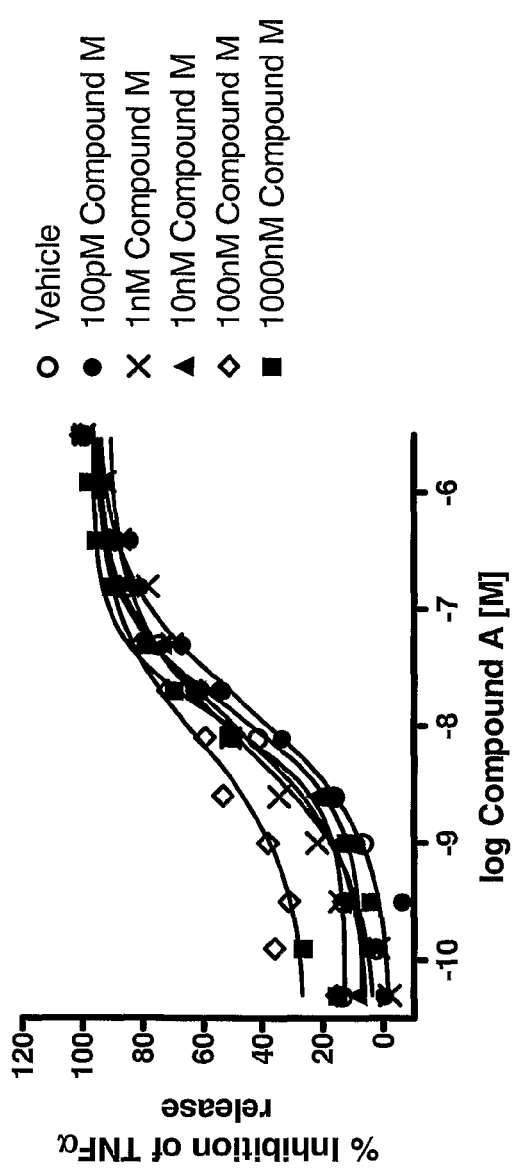
Figure 12: Effect of the combination of Compound A and Compound M on LPS stimulated TNFα production from human PBMC

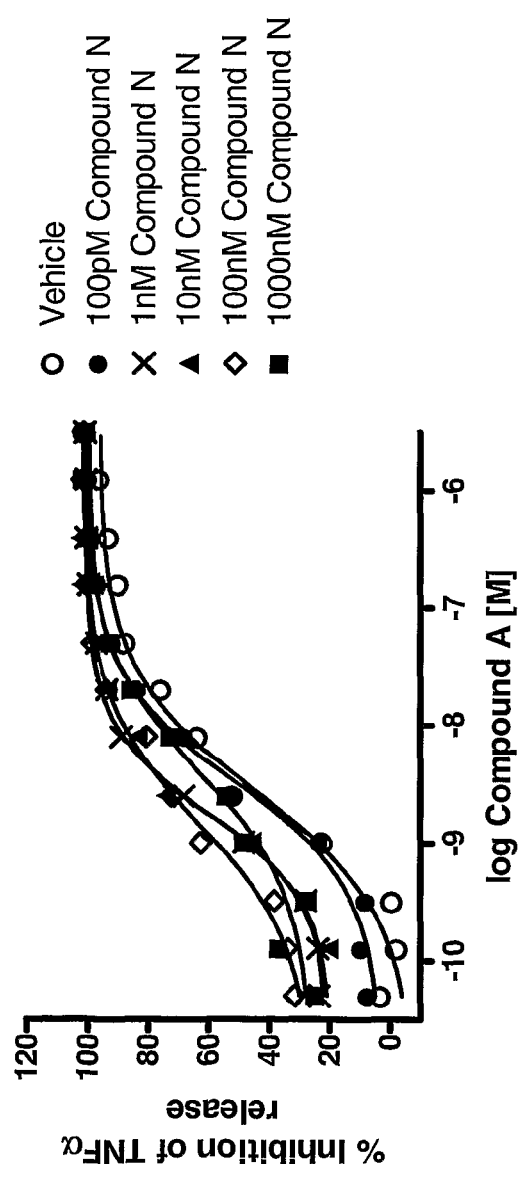
Figure 13: Effect of the combination of Compound A and Compound N on LPS stimulated TNFα production from human PBMC

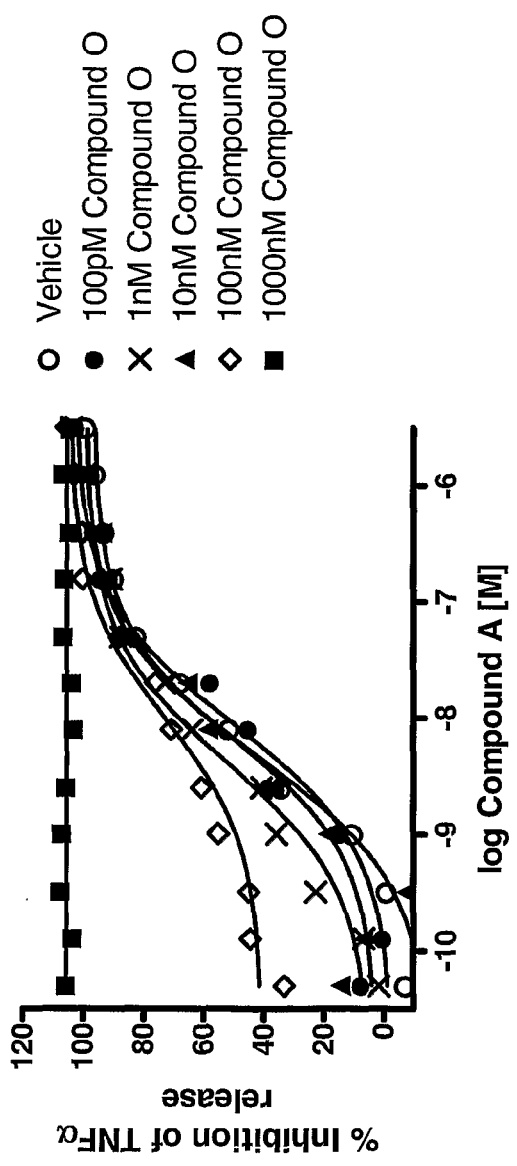
Figure 14: Effect of the combination of Compound A and Compound O on LPS stimulated TNFα production from human PBMC

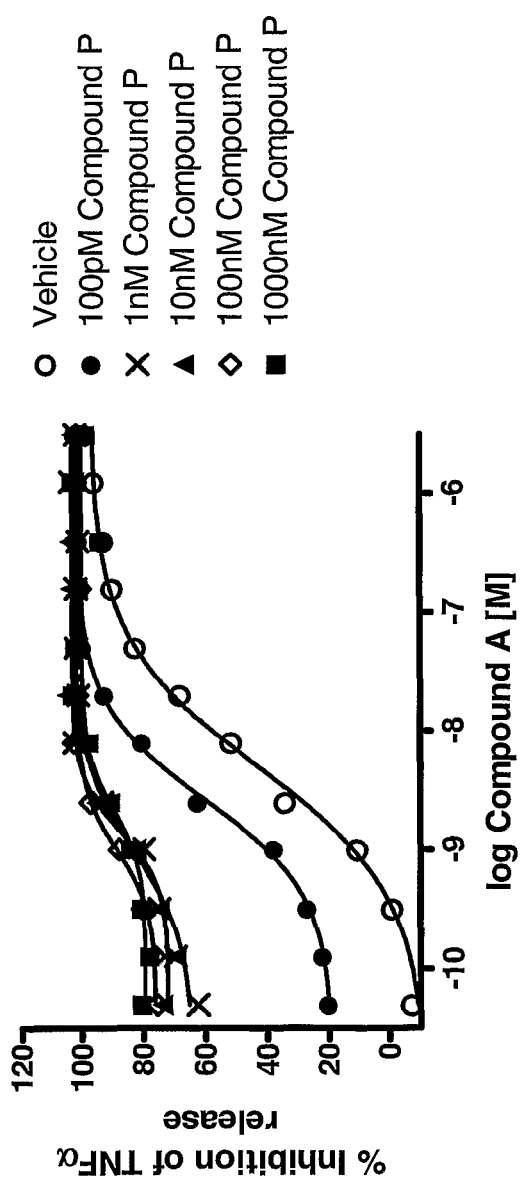
Figure 15: Effect of the combination of Compound A and Compound P on LPS stimulated TNFα production from human PBMC

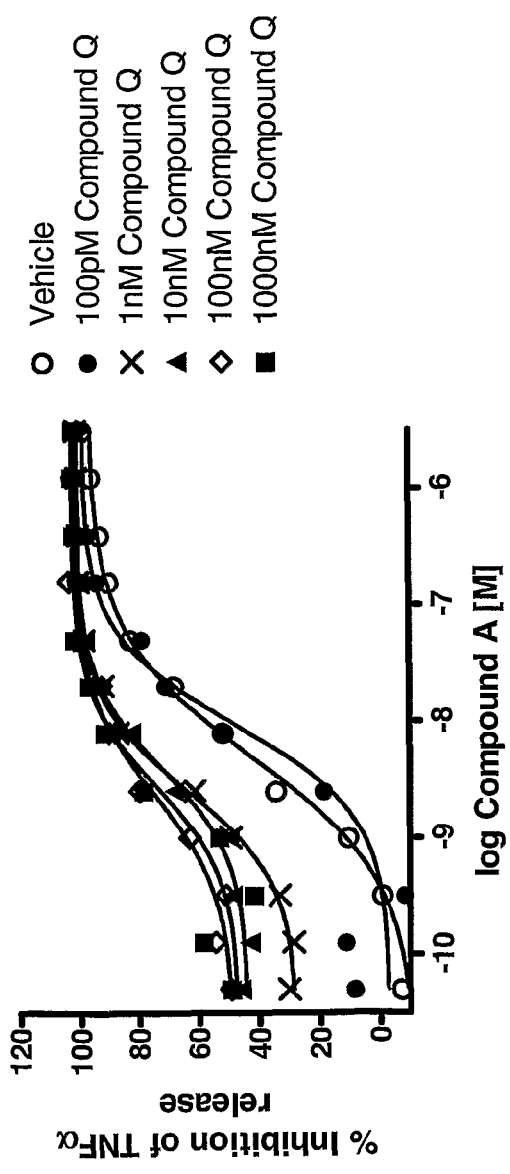
Figure 16: Effect of the combination of Compound A and Compound Q on LPS stimulated TNFα production from human PBMC

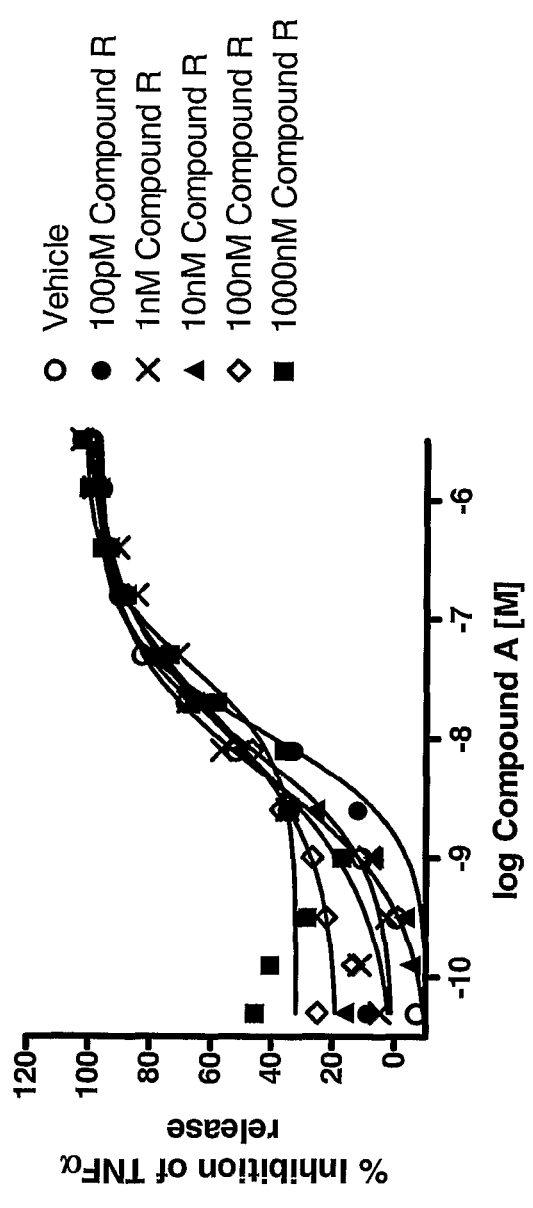
Figure 17: Effect of the combination of Compound A and Compound R on LPS stimulated TNFα production from human PBMC

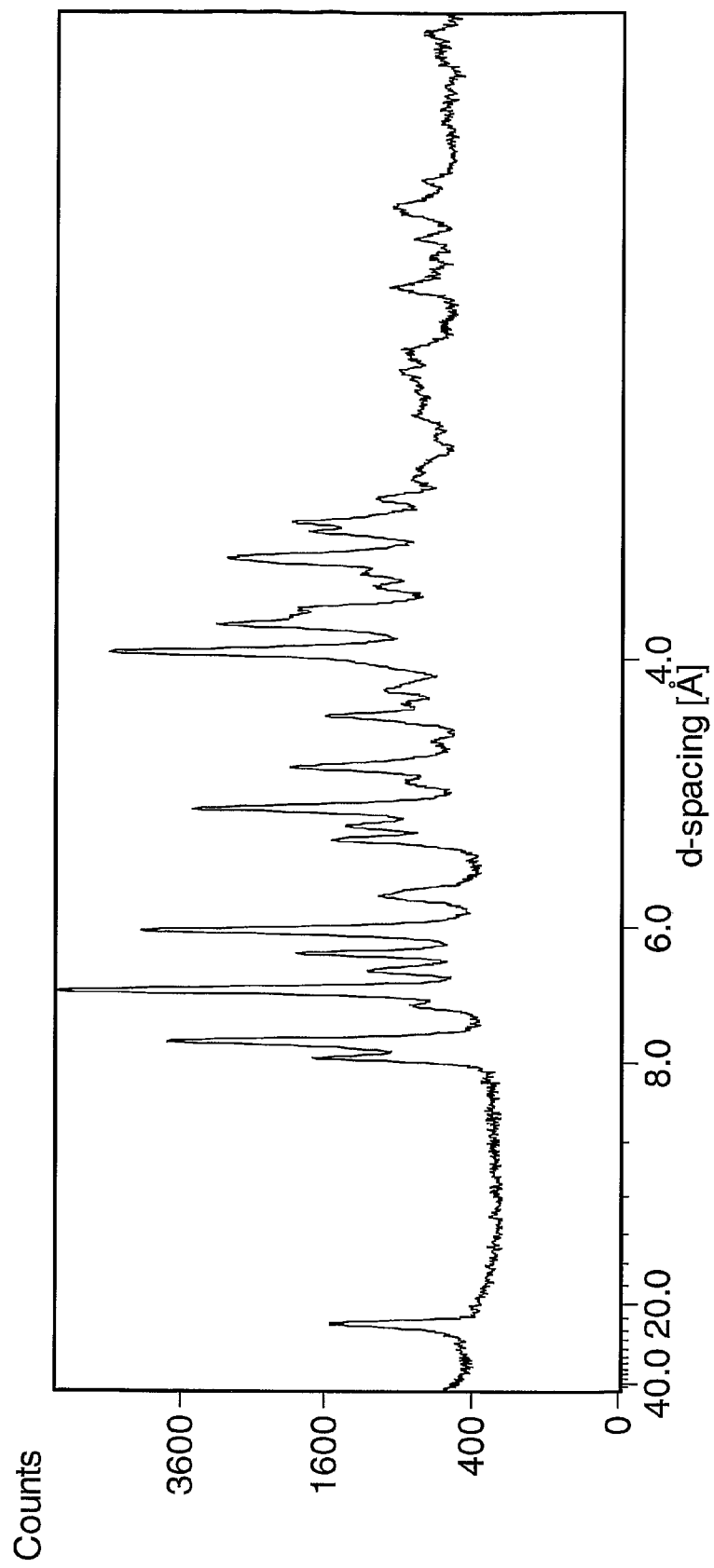
Figure 101: X-ray powder diffraction pattern of Crystalline Form A of Preparation 1 free base

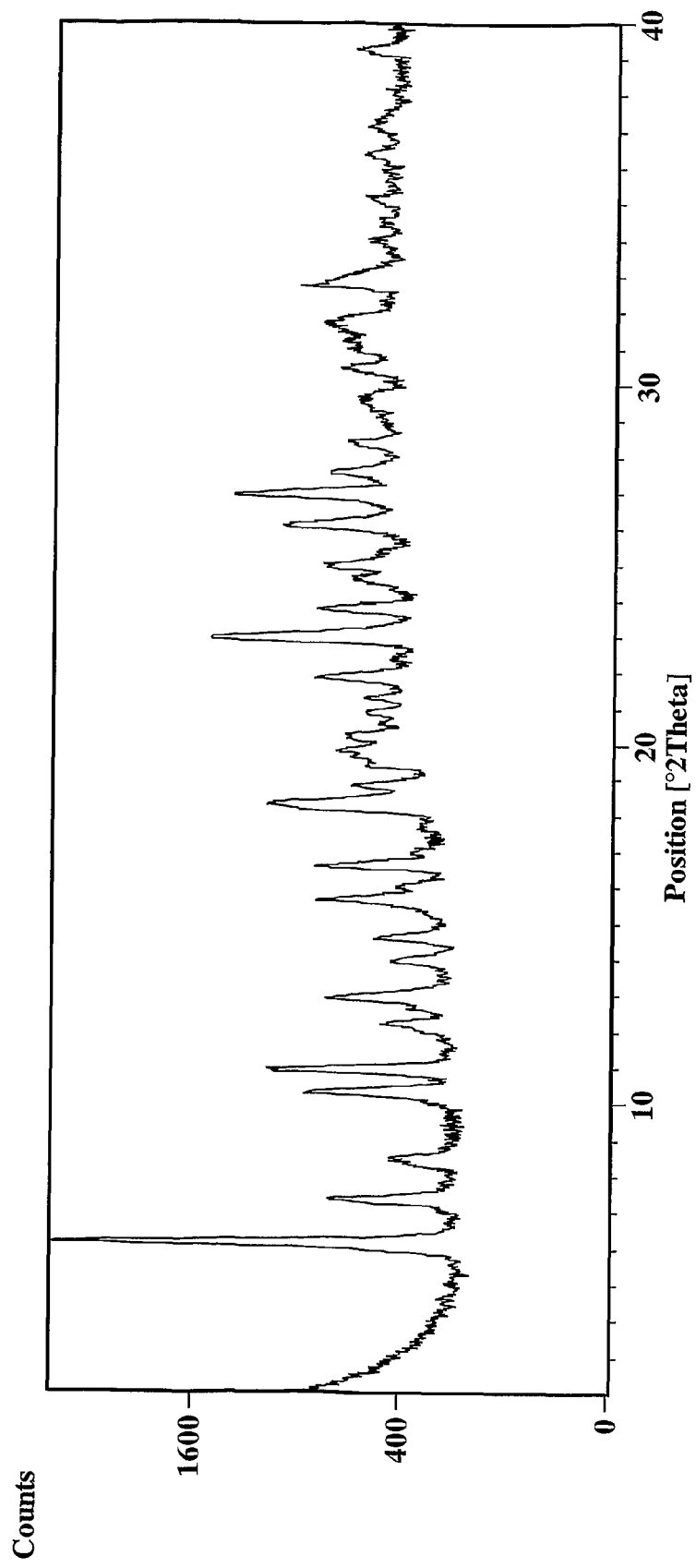
Figure 102: X-ray powder diffraction pattern of Crystalline Form A of Preparation 2 dihydrochloride salt

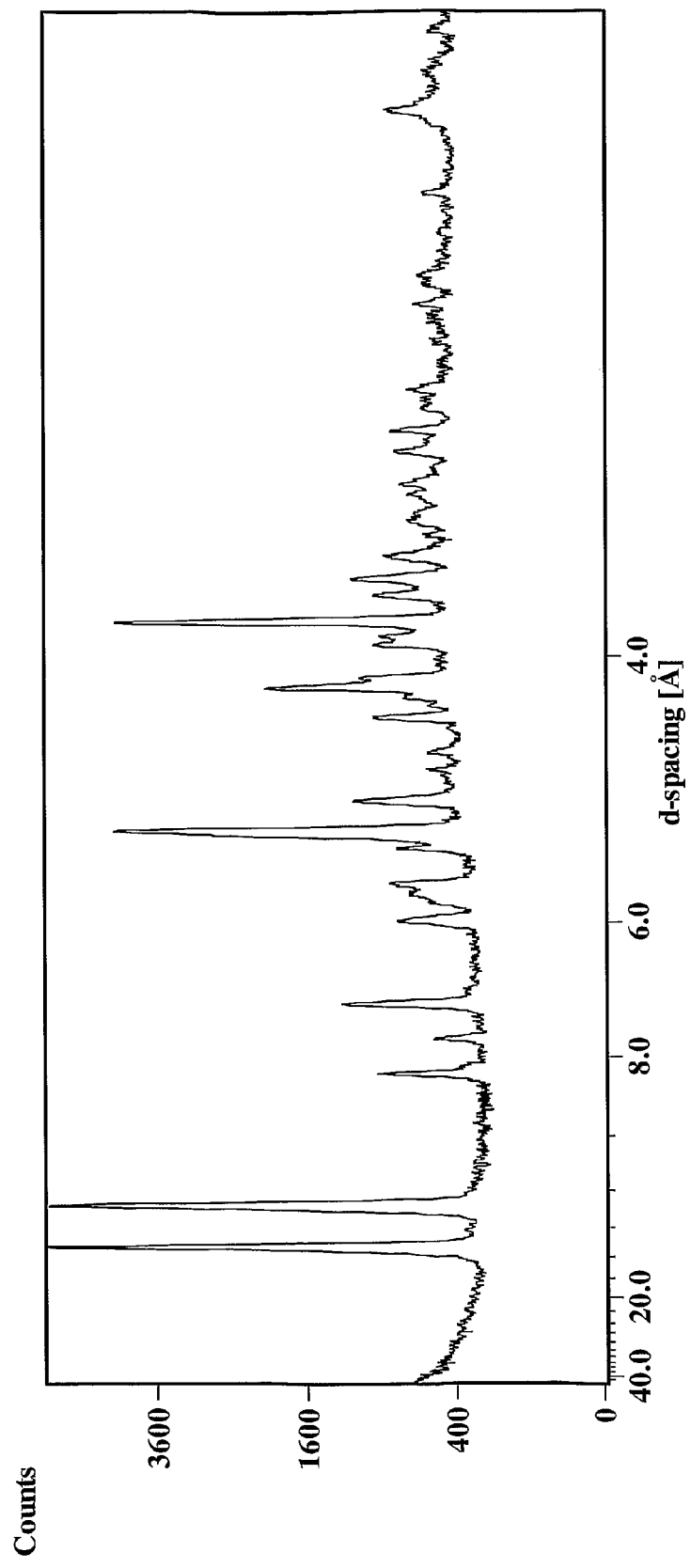
Figure 103: X-ray powder diffraction pattern of Crystalline Form A of Preparation 3
L-Tartrate Salt

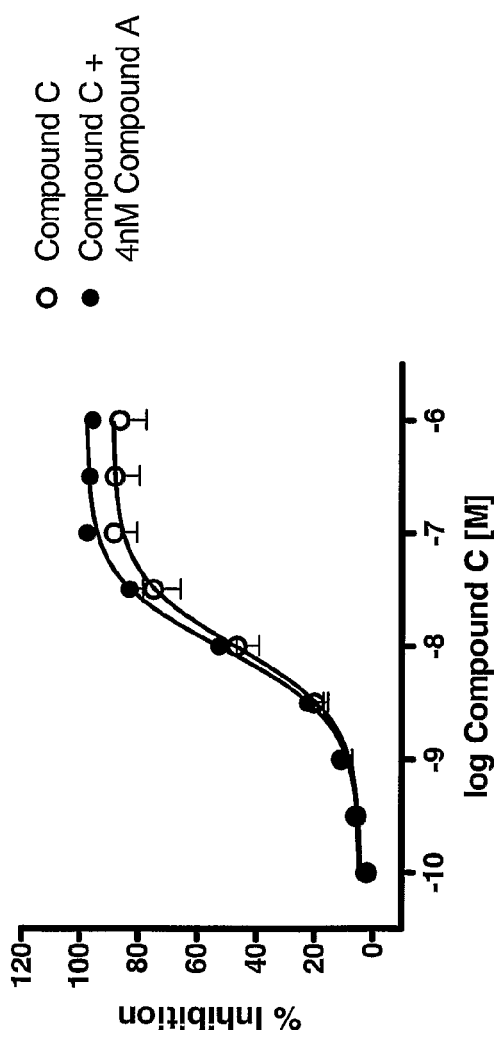
Figure 104: Cumulative concentration-response curves to Compound C in the presence of vehicle and Compound A (4 nM) in guinea pig trachea *in vitro*.

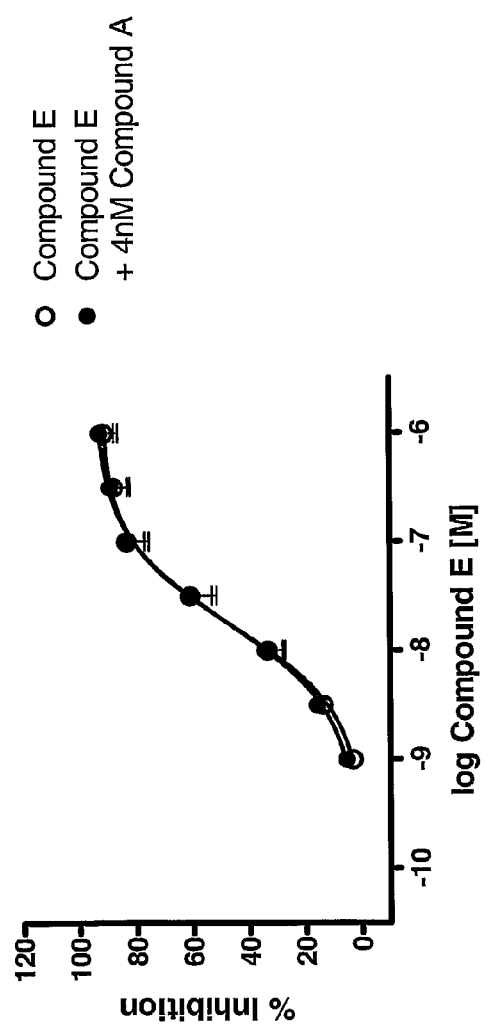
Figure 105: Cumulative concentration-response curves to Compound E in the presence of vehicle and Compound A (4 nM) in guinea pig trachea *in vitro*

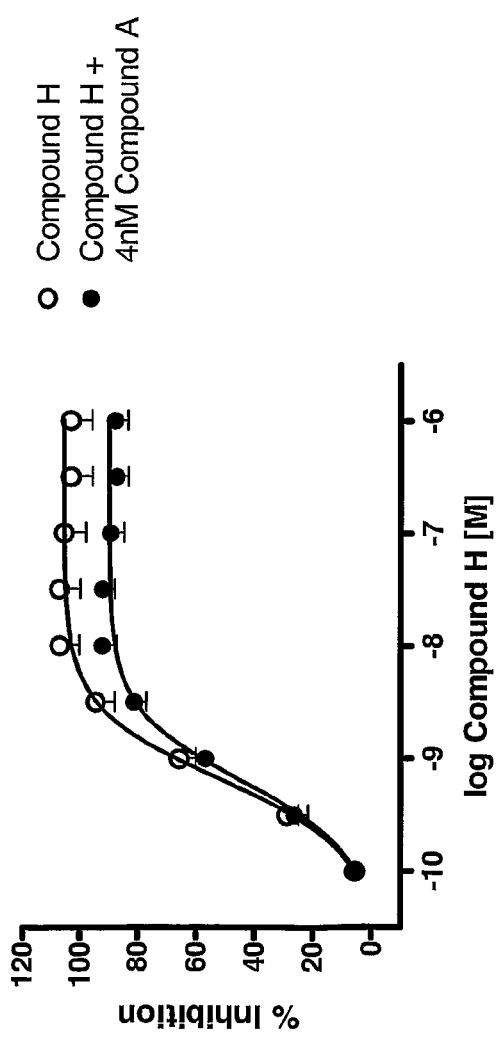
Figure 106: Cumulative concentration-response curves to Compound H in the presence of vehicle and Compound A (4 nM) in guinea pig trachea *in vitro*

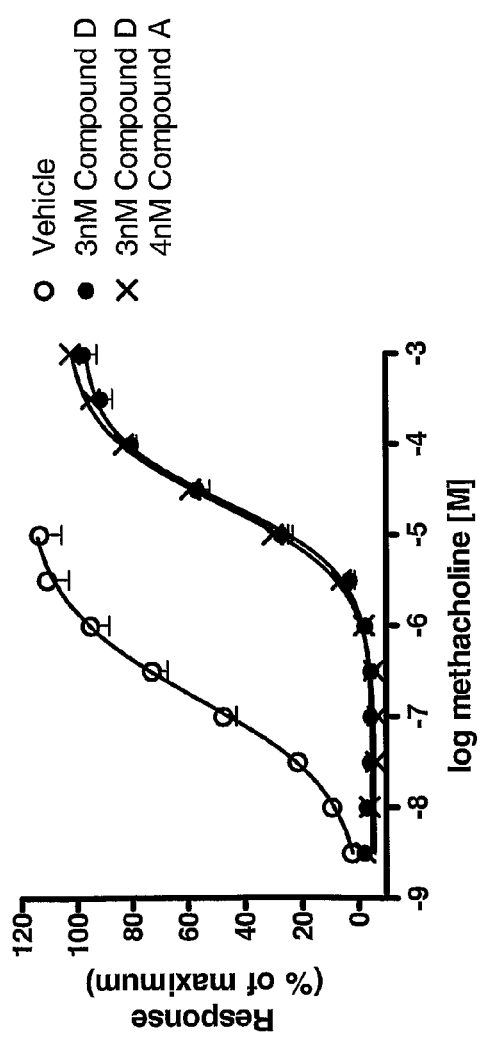
Figure 107: Cumulative concentration-response curves to methacholine in the presence of vehicle, Compound D (3 nM) and a combination of Compound D (4 nM) and Compound A (4 nM) in guinea pig trachea *in vitro*

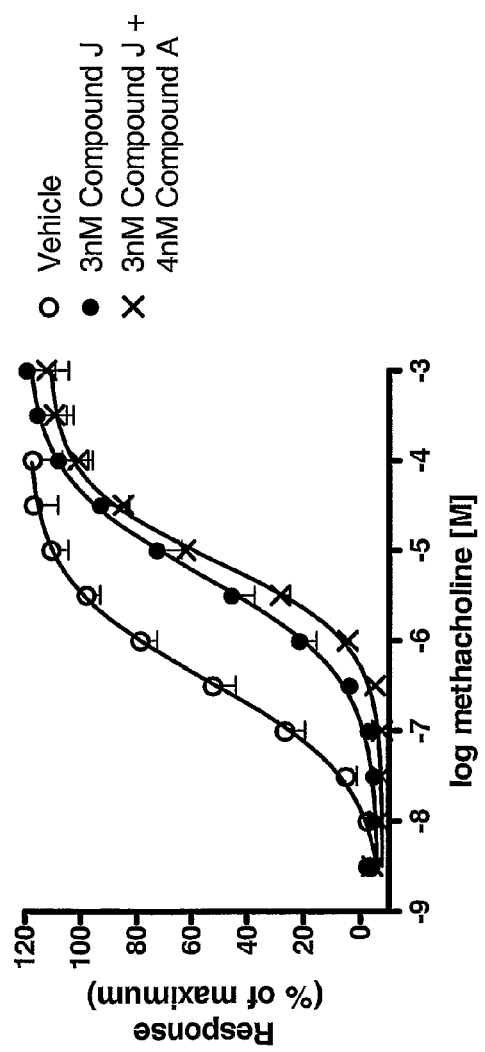
Figure 108: Cumulative concentration-response curves to methacholine in the presence of vehicle, Compound J (3 nM) and a combination of Compound J (3 nM) and Compound A (4 nM) in guinea pig trachea *in vitro*

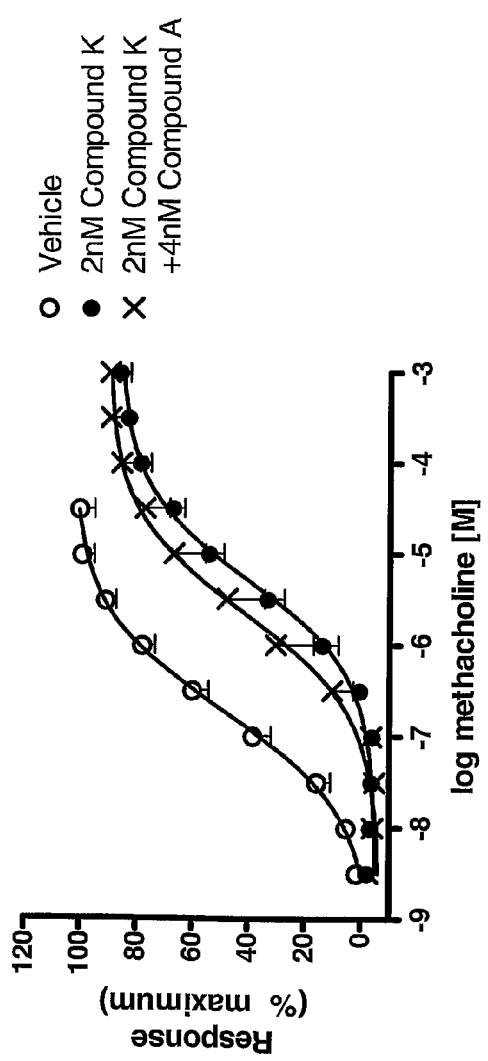
Figure 109: Cumulative concentration-response curves to methacholine in the presence of vehicle, Compound K (2 nM) and a combination of Compound K (2 nM) and Compound A (4 nM) in guinea pig trachea *in vitro*

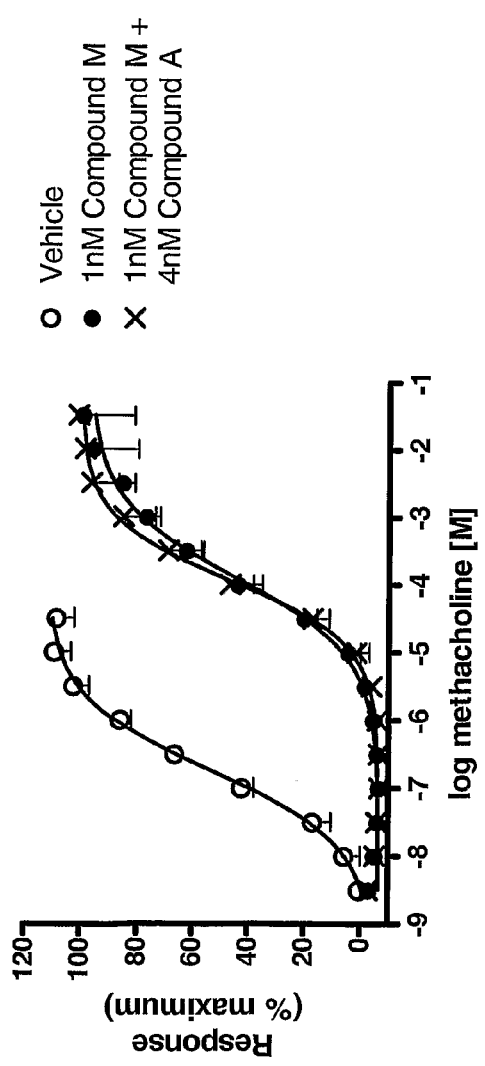
Figure 110: Cumulative concentration-response curves to methacholine in the presence of vehicle, Compound M (1 nM) and a combination of Compound M (1 nM) and Compound A (4 nM) in guinea pig trachea *in vitro*

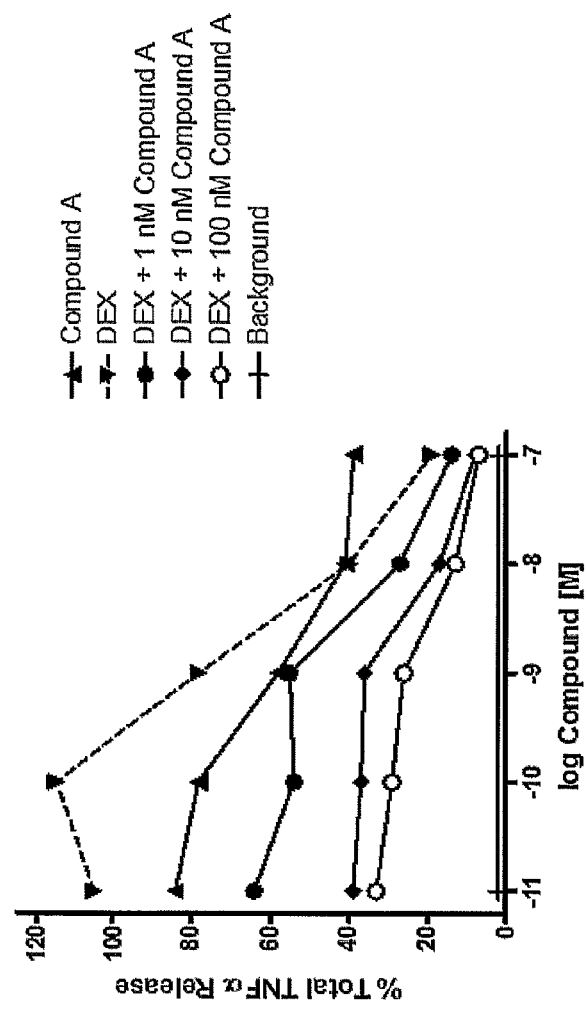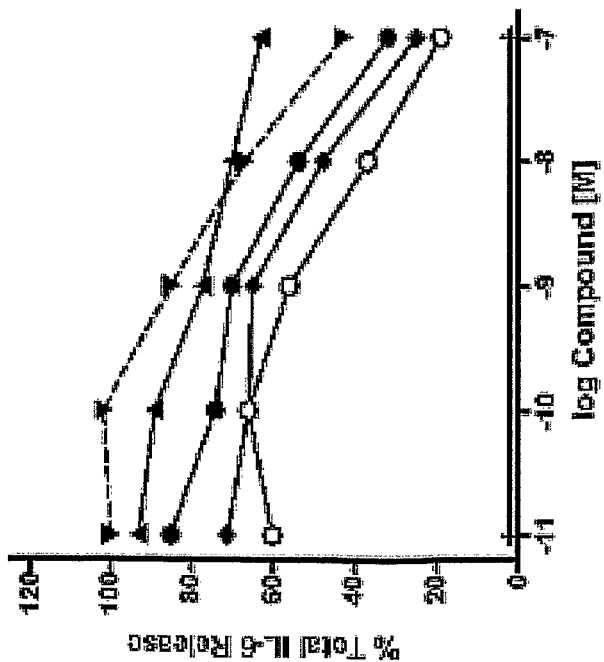
Figure 111: Effect of the combination of Compound A and Dexamethasone (DEX) on LPS- stimulated production of IL-6 from COPD Alveolar Macrophages (Panel a); and
Effect of the combination of Compound A and Dexamethasone (DEX) on LPS- stimulated production of TNFα from COPD Alveolar Macrophages (Panel b)
Panel a)
Panel b)

PHARMACEUTICAL PRODUCT COMPRISING A P38 KINASE INHIBITOR AND A SECOND ACTIVE INGREDIENT

RELATED APPLICATIONS

This application is a national stage application (under 35 U.S.C. §371) of PCT/SE2009/051444, filed Dec. 17, 2009, which claims benefit of U.S. Provisional Application 61/138,595, filed Dec. 18, 2008.

The present invention relates to a combination of two or more pharmaceutically active substances for use in the treatment of respiratory diseases (for example chronic obstructive pulmonary disease (COPD) or asthma).

The essential function of the lungs requires a fragile structure with enormous exposure to the environment, including pollutants, microbes, allergens, and carcinogens. Host factors, resulting from interactions of lifestyle choices and genetic composition, influence the response to this exposure. Damage or infection to the lungs can give rise to a wide range of diseases of the respiratory system (or respiratory diseases). A number of these diseases are of great public health importance. Respiratory diseases include Acute Lung Injury, Acute Respiratory Distress Syndrome (ARDS), occupational lung disease, lung cancer, tuberculosis, fibrosis, pneumoconiosis, pneumonia, emphysema, Chronic Obstructive Pulmonary Disease (COPD) and asthma.

Among the most common of the respiratory diseases is asthma. Asthma is generally defined as an inflammatory disorder of the airways with clinical symptoms arising from intermittent airflow obstruction. It is characterised clinically by paroxysms of wheezing, dyspnea and cough. It is a chronic disabling disorder that appears to be increasing in prevalence and severity. It is estimated that 15% of children and 5% of adults in the population of developed countries suffer from asthma. Therapy should therefore be aimed at controlling symptoms so that normal life is possible and at the same time provide basis for treating the underlying inflammation.

COPD is a term which refers to a large group of lung diseases which can interfere with normal breathing. Current clinical guidelines define COPD as a disease state characterized by airflow limitation that is not fully reversible. The airflow limitation is usually both progressive and associated with an abnormal inflammatory response of the lungs to noxious particles and gases. The most important contributory source of such particles and gases, at least in the western world, is tobacco smoke. COPD patients have a variety of symptoms, including cough, shortness of breath, and excessive production of sputum; such symptoms arise from dysfunction of a number of cellular compartments, including neutrophils, macrophages, and epithelial cells. The two most important conditions covered by COPD are chronic bronchitis and emphysema.

Chronic bronchitis is a long-standing inflammation of the bronchi which causes increased production of mucous and other changes. The patients' symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

Therapeutic agents used in the treatment of respiratory diseases include corticosteroids. Corticosteroids (also known as glucocorticosteroids or glucocorticoids) are potent anti-inflammatory agents. Whilst their exact mechanism of action is not clear, the end result of corticosteroid treatment is a decrease in the number, activity and movement of inflammatory cells into the bronchial submucosa, leading to decreased airway responsiveness. Corticosteroids may also cause reduced shedding of bronchial epithelial lining, vascular permeability, and mucus secretion. Whilst corticosteroid treatment can yield important benefits, the efficacy of these agents is often far from satisfactory, particularly in COPD. Moreover, whilst the use of steroids may lead to therapeutic effects, it is desirable to be able to use steroids in low doses to minimise the occurrence and severity of undesirable side effects that may be associated with regular administration. Recent studies have also highlighted the problem of the acquisition of steroid resistance amongst patients suffering from respiratory diseases. For example, cigarette smokers with asthma have been found to be insensitive to short term inhaled corticosteroid therapy, but the disparity of the response between smokers and non-smokers appears to be reduced with high dose inhaled corticosteroid (Tomlinson et al., Thorax 2005; 60:282-287).

A further class of therapeutic agent used in the treatment of respiratory diseases are bronchodilators. Bronchodilators may be used to alleviate symptoms of respiratory diseases by relaxing the bronchial smooth muscles, reducing airway obstruction, reducing lung hyperinflation and decreasing shortness of breath. Types of bronchodilators in clinical use include $\beta_2$ adrenoceptor agonists, muscarinic receptor antagonists and methylxanthines. Bronchodilators are prescribed mainly for symptomatic relief and they are not considered to alter the natural history of respiratory diseases.

The serine/threonine kinase, p38, is a member of the stress and mitogen activated protein kinase family (SAPK/MAPK) and participates in intracellular signalling cascades involved in a number of responses associated with inflammatory processes. Four isoforms of p38 kinase are known to exist, identified as p38α, p38β, p38γ and p38δ.

The p38 pathway is activated by stress (including tobacco smoke, infections or oxidative products) and pro-inflammatory cytokines (e.g. IL-1 or TNFα) and is involved in induction of cytokines such as TNF-α, IL-1, IL-6 and matrix metalloprotease by bacterial lipopolysaccharide (LPS). Activation of p38 by dual phosphorylation of thr$^{180}$ and tyr$^{182}$ located in the activation loop is achieved by two dual specificity upstream MAP kinase kinases (MKK); MKK3 and MKK6. In turn p38 phosphorylates numerous targets including other kinases and transcription factors. In addition to effects on transcription, p38 is involved in the control of mRNA stability of several cytokines including TNFα, IL-3, IL-6 and IL-8. Thus through this cascade, p38 kinase is thought to play a significant role in the control of transcription and translation responsible for the induction of pro-inflammatory genes and the subsequent release of pro-inflammatory cytokines such as TNFα from cells. This mechanism has been validated by investigation of the effects of inhibiting the p38 kinase enzyme on chronic inflammation and arthritis (Kumar et al, Nature Reviews Drug Discovery (2003) 2: 717-725). In particular, p38 kinase inhibitors have been described as potential agents for treating rheumatoid arthritis. PCT/GB2008/050491 (WO2009/001132) describes a novel class of compound that has high potency at the p38 kinase receptor. One compound described in WO 2009/001132 is N-cyclopropyl-3-fluoro-4-methyl-5-[3-[[1-[2-[2-(methylamino)

ethoxy]phenyl]cyclopropyl]amino]-2-oxo-1(2H)-pyrazinyl]-benzamide and salts thereof.

Combination products comprising a β₂ adrenoceptor agonist and a corticosteroid are available. One such product is a combination of budesonide and formoterol fumarate (marketed by AstraZeneca under the tradename Symbicort®), which has proven to be effective in controlling asthma and COPD, and improving quality of life in many patients.

In view of the complexity of respiratory diseases such as asthma and COPD, it is unlikely that any one mediator can satisfactorily treat a respiratory disease alone. Moreover, whilst combination treatments using a β₂ adrenoceptor agonist and a corticosteroid deliver significant patient benefits, there remains a medical need for new therapies against respiratory diseases such as asthma and COPD, in particular for therapies with disease modifying potential.

Accordingly, the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof, and a second active ingredient selected from:
an Adenosine A2A receptor antagonist;
an anti-infective;
a non-steroidal Glucocorticoid Receptor (GR Receptor) Agonist;
an antioxidant;
a β₂ adrenoceptor agonist;
a CCR1 antagonist;
a chemokine antagonist (not CCR1);
a corticosteroid;
a CRTh2 antagonist;
a DP1 antagonist;
a formyl peptide receptor antagonist;
a Histone Deacetylase activator;
a chloride channel hCLCA1 blocker
an Epithelial sodium channel blocker (ENAC blocker)).
an Inter-cellular adhesion molecule 1 blocker (ICAM blocker);
an IKK2 kinase inhibitor;
a JNK kinase inhibitor;
a cyclooxygenase inhibitor (COX inhibitor);
a lipoxygenase inhibitor;
a leukotriene receptor antagonist;
a dual β₂ adrenoceptor agonist/M₃ receptor antagonist (MABA compound);
a MEK-1 kinase inhibitor
a myeloperoxidase inhibitor (MPO inhibitor);
a muscarinic antagonist;
a phosphodiesterase PDE4 inhibitor;
a phosphatidylinositol 3 (PI3)-kinase γ inhibitor (PI 3 kinase γ inhibitor)
a peroxisome proliferator activated receptor agonist (PPARγ agonist);
a protease inhibitor;
a retinoic acid receptor modulator (RAR γ modulator)
a Statin;
a thromboxane antagonist; or
a vasodilator.

A beneficial therapeutic effect may be observed in the treatment of respiratory diseases if the first active ingredient according to the present invention is used in combination with a second active ingredient according to the present invention. The beneficial effect may be observed when the two active substances are administered simultaneously (either in a single pharmaceutical preparation or via separate preparations), or sequentially or separately via separate pharmaceutical preparations.

The pharmaceutical product of the present invention may, for example, be a pharmaceutical composition comprising the first and second active ingredients in admixture. Alternatively, the pharmaceutical product may, for example, be a kit comprising a preparation of the first active ingredient and a preparation of the second active ingredient and, optionally, instructions for the simultaneous, sequential or separate administration of the preparations to a patient in need thereof.

The first active ingredient of the present invention is a member of a novel class of compound described in PCT application PCT/GB2008/050491 (WO 2009/001132) which display high potency at the p38 kinase receptor. The name N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide was generated using the commercially available chemical naming software package ACDLABS and was generated from the structure:

A suitable salt of N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide is, for example, a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-Camphorsulfonic acid salt), formate, glutamate, glutarate, glycolate, hippurate (2-(benzoylamino)acetate), orotate, xylate (p-xylene-2-sulphonate), pamoic (2,2'-dihydroxy-1,1'-dinaphthylmethane-3,3'-dicarboxylate), palmitate or furoate. It is to be understood for the avoidance of confusion that salts may exist in varying stoichiometries, for example, but not limited to, hemi-, mono-, and di-, and that the invention encompasses all such forms.

In one aspect the present invention provides a pharmaceutical product wherein the first active ingredient is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide.

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1 (2H)-pyrazinyl]-benzamide or a salt thereof (such as the hydrochloride or L-tartaric acid salt), and a second active ingredient selected from:

a muscarinic antagonist;

a $\beta_2$ adrenoceptor agonist;

a dual $\beta_2$ adrenoceptor agonist/$M_3$ receptor antagonist (MABA compound);

a corticosteroid;

a non-steroidal Glucocorticoid Receptor (GR Receptor) Agonist;

an IKK2 kinase inhibitor;

a phosphodiesterase PDE4 inhibitor or an inhibitor of neutrophil elastase.

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1 (2H)-pyrazinyl]-benzamide or a salt thereof and a second active ingredient which is a muscarinic antagonist.

Examples of muscarinic antagonists that may be utilised in accordance with the present invention include aclidinium bromide, glycopyrrolate (such as R,R-, R,S-, S,R-, or S,S-glycopyrronium bromide), oxitropium bromide, pirenzepine, telenzepine, tiotropium bromide, darotropium ((1R,3R,5S)-3-(2-cyano-2,2-diphenylethyl)-8,8-dimethyl-8-azoniabicyclo[3,2,1]octane bromide), 3(R)-(2-hydroxy-2,2-dithien-2-ylacetoxy)-1-(3-phenoxypropyl)-1-azoniabicyclo[2.2.2] octane bromide (see WO 01/04118), 3(R)-1-phenethyl-3-(9H-xanthene-9-carbonyloxy)-1-azoniabicyclo[2.2.2]octane bromide or (3R)-3-[(2S)-2-cyclopentyl-2-hydroxy-2-thien-2-ylacetoxy]-1-(2-phenoxyethyl)-1-azoniabicyclo[2.2.2]actane bromide (see WO 01/04118); or a quaternary ammonium salt (such as [2-((S)-cyclohexyl-hydroxy-phenyl-methyl)-oxazol-5-ylmethyl]-dimethyl-(3-phenoxy-propyl)-ammonium salt, [2-((R)-cyclohexyl-hydroxy-phenyl-methyl)-oxazol-5-ylmethyl]-dimethyl-(3-phenoxy-propyl)-ammonium salt, [2-((R)-cyclohexyl-hydroxy-phenyl-methyl)-oxazol-5-ylmethyl]-dimethyl-(2-phenethyloxy-ethyl)-ammonium salt, [2-((R)-cyclohexyl-hydroxy-phenyl-methyl)-oxazol-5-ylmethyl]-[3-(3,4-dichloro-phenoxy)-propyl]dimethyl-ammonium salt, [2-((R)-cyclohexyl-hydroxy-phenyl-methyl)-oxazol-5-ylmethyl]-[2-(3,4-dichloro-benzyloxy)-ethyl]-dimethyl-ammonium salt, [2-(4-chloro-benzyloxy)-ethyl]-[2-((R)-cyclohexyl-hydroxy-phenyl-methyl)-oxazol-5-ylmethyl]-dimethyl-ammonium salt, or (R)-1-[2-(4-fluoro-phenyl)-ethyl]-3-((S)-2-phenyl-2-piperidin-1-yl-propionyloxy)-1-azonia-bicyclo[2.2.2]octane; wherein the counter-ion is, for example, chloride, bromide, sulfate, methanesulfonate, benzenesulfonate (besylate), toluenesulfonate (tosylate), napthalenebissulfonate (napadisylate), hemi-napthalenebissulfonate (hemi-napadisylate), phosphate, acetate, citrate, lactate, tartrate, mesylate, maleate, fumarate or succinate.

In a further embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1 (2H)-pyrazinyl]-benzamide or a salt thereof (such as the hydrochloride or L-tartaric acid salt), and a second active ingredient which is selected from:

a [2-((R)-cyclohexyl-hydroxy-phenyl-methyl)-oxazol-5-ylmethyl]-dimethyl-(3-phenoxy-propyl)-ammonium salt, a [2-(4-chloro-benzyloxy)-ethyl]-[2-((R)-cyclohexyl-hydroxy-phenyl-methyl)-oxazol-5-ylmethyl]-dimethyl-ammonium salt, a (R)-1-[2-(4-fluoro-phenyl)-ethyl]-3-((S)-2-phenyl-2-piperidin-1-yl-propionyloxy)-1-azonia-bicyclo[2.2.2]octane salt, a ((R)-3-(1-phenyl-cycloheptanecarbonyloxy)-1-(pyridin-2-ylcarbamoylmethyl)-1-azonia-bicyclo[2.2.2]octane salt, and a a (R)-1-[3-(cyclohexyl-hydroxy-phenyl-methyl)-isoxazol-5-ylmethyl]-3-(3-fluoro-phenoxy)-1-azonia-bicyclo[2.2.] octane salt, wherein each salt has a counter-ion which may be any pharmaceutically acceptable anion for example, chloride, bromide, sulfate, methanesulfonate, benzenesulfonate (besylate), 4-methylbenzenesulfonate (tosylate), naphthalene-1,5-bissulfonate (napadisylate), hemi-naphthalene-1,5-bissulfonate (hemi-napadisylate), 2-hydroxyethanesulfonate, phosphate, acetate, citrate, lactate, tartrate, mesylate, maleate, fumarate or succinate.

In one embodiment of the invention, the second active ingredient is a [2-((R)-cyclohexyl-hydroxy-phenyl-methyl)-oxazol-5-ylmethyl]-dimethyl-(3-phenoxy-propyl)-ammonium salt. [2-((R)-Cyclohexyl-hydroxy-phenyl-methyl)-oxazol-5-ylmethyl]-dimethyl-(3-phenoxy-propyl)-ammonium salts are described in WO 2007/017669, e.g. [2-((R)-cyclohexyl-hydroxy-phenyl-methyl)-oxazol-5-ylmethyl]-dimethyl-(3-phenoxy-propyl)-ammonium bromide.

In one embodiment of the invention, the second active ingredient is a [2-(4-chloro-benzyloxy)-ethyl]-[2-((R)-cyclohexyl-hydroxy-phenyl-methyl)-oxazol-5-ylmethyl]-dimethyl-ammonium salt. [2-(4-Chloro-benzyloxy)-ethyl]-[2-((R)-cyclohexyl-hydroxy-phenyl-methyl)-oxazol-5-ylmethyl]-dimethyl-ammonium salts are described in WO 2007/017669, e.g. [2-(4-chloro-benzyloxy)-ethyl]-[2-((R)-cyclohexyl-hydroxy-phenyl-methyl)-oxazol-5-ylmethyl]-dimethyl-ammonium methane sulfonate and WO 2008/096149 e.g. [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-bissulfonate.

In one embodiment of the invention, the second active ingredient is a (R)-1-[2-(4-fluoro-phenyl)-ethyl]-3-((S)-2-phenyl-2-piperidin-1-yl-propionyloxy)-1-azonia-bicyclo [2.2.2]octane salt. (R)-1-[2-(4-Fluoro-phenyl)-ethyl]-3-((S)-2-phenyl-2-piperidin-1-yl-propionyloxy)-1-azonia-bicyclo [2.2.2]octane salts are described in WO2008/75005, e.g. as (R)-1-[2-(4-fluoro-phenyl)-ethyl]-3-((S)-2-phenyl-2-piperidin-1-yl-propionyloxy)-1-azonia-bicyclo[2.2.2]octane bromide and (R)-1-[2-(4-fluoro-phenyl)-ethyl]-3-((S)-2-phenyl-2-piperidin-1-yl-propionyloxy)-1-azonia-bicyclo[2.2.2] octane chloride, and in PCT/SE2009/050743 e.g. (R)-1-[2-(4-fluoro-phenyl)-ethyl]-3-((S)-2-phenyl-2-piperidin-1-yl-propionyloxy)-1-azonia-bicyclo[2.2.2]octane 4-methylbenzenesulfonate.

In one embodiment of the invention, the second active ingredient is a ((R)-3-(1-phenyl-cycloheptanecarbonyloxy)-1-(pyridin-2-ylcarbamoylmethyl)-1-azonia-bicyclo[2.2.2] octane salt. ((R)-3-(1-phenyl-cycloheptanecarbonyloxy)-1-(pyridin-2-ylcarbamoylmethyl)-1-azonia-bicyclo[2.2.2] octane salts are described in WO 2009/138707 and WO 2009/139708 e.g. ((R)-3-(1-phenyl-cycloheptanecarbonyloxy)-1-(pyridin-2-ylcarbamoylmethyl)-1-azonia-bicyclo[2.2.2] octane bromide.

In one embodiment of the invention, the second active ingredient is a (R)-1-[3-(cyclohexyl-hydroxy-phenyl-methyl)-isoxazol-5-ylmethyl]-3-(3-fluoro-phenoxy)-1-azonia-bicyclo[2.2.]octane salt. (R)-1-[3-(Cyclohexyl-hydroxyphenyl-methyl)-isoxazol-5-ylmethyl]-3-(3-fluoro-phenoxy)-1-azonia-bicyclo[2.2.]octane salts are described in WO 2008/099186, e.g. (R)-1-[3-(cyclohexyl-hydroxy-phenyl-methyl)-isoxazol-5-ylmethyl]-3-(3-fluoro-phenoxy)-1-azonia-bicyclo[2.2.]octane chloride, and PCT/SE2009/050926 e.g. (R)-1-[3-(cyclohexyl-hydroxy-phenyl-methyl)-isoxazol-5-ylmethyl]-3-(3-fluoro-phenoxy)-1-azonia-bicyclo[2.2.]octane 2-hydroxy-ethanesulfonate.

In another embodiment, the second active ingredient is aclidinium or a pharmaceutically acceptable salt thereof (e.g. bromide).

In another embodiment, the second active ingredient is glycopyrrolate or a pharmaceutically acceptable salt thereof (e.g. iodide).

In another embodiment, the second active ingredient is tiotropium or a pharmaceutically acceptable salt thereof (e.g. iodide or bromide).

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof and a second active ingredient is a $\beta_2$ adrenoceptor agonist.

A $\beta_2$-adrenoceptor agonist is any compound or substance capable of stimulating the $\beta_2$-receptors and acting as a bronchodilator. In the context of the present specification, unless otherwise stated, any reference to a $\beta_2$-adrenoceptor agonist includes an active salt, solvate or derivative that may be formed from said $\beta_2$-adrenoceptor agonist or any enantiomer or mixture thereof. Examples of possible salts or derivatives of $\beta_2$-adrenoceptor agonist are acid addition salts such as the salts of hydrochloric acid, hydrobromic acid, sulphuric acid, phosphoric acid, methanesulphonic acid, acetic acid, fumaric acid, succinic acid, lactic acid, citric acid, tartaric acid, 1-hydroxy-2-naphthalenecarboxylic acid, maleic acid, and pharmaceutically acceptable esters (e.g. $C_1$-$C_6$ alkyl esters). The $\beta_2$-agonists may also be in the form of solvates, e.g. hydrates.

Examples of a $\beta_2$-adrenoceptor agonist that may be used in the pharmaceutical product according to one embodiment include
    metaproterenol
    isoproterenol
    isoprenaline
    albuterol
    salbutamol (e.g. as sulphate)
    formoterol (e.g. as fumarate)
    salmeterol (e.g. as xinafoate)
    terbutaline
    orciprenaline
    bitolterol (e.g. as mesylate)
    pirbuterol or
    indacaterol.

The $\beta_2$-adrenoceptor agonist of an alternative embodiment may be a long-acting $\beta_2$-agonist (i.e. a $\beta_2$-agonist with activity that persists for more than 24 hours), for example
    salmeterol (e.g. as xinafoate)
    formoterol (e.g. as fumarate)
    bambuterol (e.g. as hydrochloride
    carmoterol (TA 2005, chemically identified as [R—(R*,R*)]-8-hydroxy-5-[1-hydroxy-2-[[2-(4-methoxy-phenyl)-1-methylethyl]-amino]ethyl]-2(1H)-quinolone monohydrochloride, also identified by Chemical Abstract Service Registry Number 137888-11-0 and disclosed in U.S. Pat. No. 4,579,854)
    a benzothiazolone as disclosed in WO2005074924, or WO2006056741 (for example 7-[(R)-2-((1S,2S)-2-Benzyloxy-cyclopentylamino)-1-hydroxyethyl]-4-hydroxy-3H-benzothiazol-2-one)
    an aryl aniline as disclosed in WO 2003042164 or WO2006133942 (for example N-[2-[4-[(3-phenyl-4-methoxyphenyl)amino]phenyl]ethyl]-(R)-2-hydroxy-2-(8-hydroxy-1,2-dihydro-2-oxoquinolin-5-yl)ethylamine)
    compounds disclosed in WO200607489 (for example 5-[(R)-2-(2-{4-[4-(2-amino-2-methyl-propoxy)-phenylamino]-phenyl}-ethylamino)-1-hydroxyethyl]-8-hydroxy-1H-quinolin-2-one)
    a formanilide as disclosed in WO2004011416, WO2005030678, or 2006066907 (for example N-(2-[4-((R)-2-hydroxy-2-phenylethylamino)phenyl]ethyl)-(R)-2-hydroxy-2-(3-formamido-4-hydroxyphenyl)ethylamine)
    compounds disclosed in WO2005121065 (for example 8-hydroxy-5-[(1R)-1-hydroxy-2-[6-(phenethylamino)hexylamino]ethyl]-1H-quinolin-2-one)
    compounds disclosed in WO2003024439 (for example (1R)-4-[2-[6-[2-[(2,6-dichlorophenyl)methoxy]ethoxy]hexylamino]-1-hydroxyethyl]-2-(hydroxymethyl)phenol)
    compounds disclosed in WO2004037773 (for example 4-[(1R)-2-[6-[4-(3-cyclopentylsulfonylphenyl)butoxy]hexylamino]-1-hydroxyethyl]-2-(hydroxymethyl)phenol).
    a benzenesulfonamide derivative as disclosed in WO2002066422 (for example 3-(4-{[6-({(2R)-2-hydroxy-2-[4-hydroxy-3-(hydroxy-methyl)phenyl]ethyl}amino)-hexyl]oxy}butyl)benzenesulfonamide)
    a formanilide disclosed in WO2002076933 (for example 3-(4-{[6-({(2R)-2-[3-(formylamino)-4-hydroxyphenyl]-2-hydroxyethyl}amino)hexyl]oxy}-butyl)-benzenesulfonamide)
    a compound GSK159797, GSK159802, GSK597901, GSK642444 or GSK678007
    an indole derivative as disclosed in WO2004032921 (for example N-[(2,6-dimethoxyphenyl)methyl]-5-[2-[[2-hydroxy-2-[4-hydroxy-3-(hydroxymethyl)phenyl]ethyl]amino]propyl]-1H-indole-2-carboxamide).
    compounds disclosed in WO2006051375 (for example N-(1-adamantyl)-2-[3-[(2R)-2-[[(2R)-2-hydroxy-2-[4-hydroxy-3-(hydroxymethyl)phenyl]ethyl]amino]propyl]phenyl]acetamide).
    compounds disclosed in WO2008017637 (for example 8-[(1R)-2-[[4-[3-(4-chlorophenyl)-5-methyl-1,2,4-triazol-1-yl]-2-methylbutan-2-yl]amino]-1-hydroxyethyl]-6-hydroxy-4H-1,4-benzoxazin-3-one).
    compounds disclosed in WO2008023003 (for example N-[5-[(1R)-2-[[4-(4,4-diethyl-2-oxo-3,1-benzoxazin-1-yl)-2-methylbutan-2-yl]amino]-1-hydroxyethyl]-2-hydroxyphenyl]methanesulfonamide).
    compounds disclosed in WO2006122788, and WO2008095720 (for example 5-(2-{[6-(2,2-difluoro-2-phenylethoxy)hexyl]amino}-1-hydroxyethyl)-8-hydroxyquinolin-2(1H)-one).
    compounds disclosed in WO2008046598 (for example 5-[(1R)-2-[2-[4-(2,2-difluoro-2-phenylethoxy)phenyl]ethylamino]-1-hydroxyethyl]-8-hydroxy-1H-quinolin-2-one).
    compounds disclosed in WO2007124898 (for example 5-(2-[(6-(2-[(2,6-dichlorobenzyl)(methyl)amino]ethoxy)hexyl]amino]-1-hydroxyethyl]-8-hydroxyquinolin-2(1H)-one).

In yet another alternative embodiment of the invention, the $\beta_2$-adrenoceptor agonist is selected from:

N-[2-(Diethylamino)ethyl]-N-(2-{[2-(4-hydroxy-2-oxo-2,3-dihydro-1,3-benzothiazol-7-yl)ethyl]amino]ethyl)-3-[2-(1-naphthyl)ethoxy]propanamide; as disclosed in WO2008096111

N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-chlorophenyl)ethoxy]propanamide; as disclosed in WO2008096121

7-[(1R)-2-({2-[(3-{[2-(2-Chlorophenyl)ethyl]amino}propyl)thio]ethyl}amino)-1-hydroxyethyl]-4-hydroxy-1,3-benzothiazol-2(3H)-one; as outlined in WO2008104776

4-Hydroxy-7-[1-hydroxy-2-(2-{3-[(2-methoxy-benzylamino)-methyl]-phenyl}-ethylamino)-ethyl]-3H-benzothiazol-2-one, as disclosed in WO2008106016, and, N-Cyclohexyl-3-[2-(3-fluorophenyl)ethylamino]-N-[2-[2-(4-hydroxy-2-oxo-3H-1,3-benzothiazol-7-yl)ethylamino]ethyl]propanamide, as disclosed in WO2008075026 or a pharmaceutically acceptable salt thereof.

In yet a further embodiment of the invention, the β$_2$-adrenoceptor agonist is selected from:

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide;

N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-chlorophenyl)ethoxy]propanamide dihydrobromide;

7-[(1R)-2-({2-[(3-{[2-(2-Chlorophenyl)ethyl]amino}propyl)thio]ethyl}amino)-1-hydroxyethyl]-4-hydroxy-1,3-benzothiazol-2(3H)-one dihydrobromide;

4-Hydroxy-7-[1-hydroxy-2-(2-{3-[(2-methoxy-benzylamino)-methyl]-phenyl}-ethylamino)-ethyl]-3H-benzothiazol-2-one dihydrobromide, and, N-Cyclohexyl-3-[2-(3-fluorophenyl)ethylamino]-N-[2-[2-(4-hydroxy-2-oxo-3H-1,3-benzothiazol-7-yl)ethylamino]ethyl]propanamide di-D-mandelate salt.

In one embodiment of the present invention, the second active ingredient is N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g dihydrobromide). This compound is described in WO 2008/096111.

In one embodiment of the present invention, the second active ingredient is indacaterol or a pharmaceutically acceptable salt thereof (e.g maleate).

In one embodiment of the present invention, the second active ingredient is N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate). This compound is described in WO 2008/075026.

In one embodiment of the present invention, the second active ingredient is 4-hydroxy-7-[(1R)-1-hydroxy-2-[2-[3-[[(2methoxyphenyl)methylamino]methyl]phenyl]ethylamino]ethyl]-3H-1,3-benzothiazol-2-one or a pharmaceutically acceptable salt thereof (e.g. hydrochloride). This compound is described in WO2007/106016.

In one embodiment of the present invention, the second active ingredient is 7-[(1R)-2-({2-[(3-{[2-(2-chlorophenyl)ethyl]amino}propyl)thio]ethyl}amino)-1-hydroxyethyl]-4-hydroxy-1,3-benzothiazol-2(3H)-one or a pharmaceutically acceptable salt (e.g. dihydrobromide). This compound is described in WO 2007/027134.

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1 (2H)-pyrazinyl]-benzamide or a salt thereof and a second active ingredient is a dual β$_2$ adrenoceptor agonist/M$_3$ receptor antagonist (MABA compound).

A MABA compound is a compound having dual activity as both a muscarinic antagonist and as a β$_2$-adrenoceptor agonist, for example a MABA is a compound disclosed in: WO2004089892, WO2004106333, US20040167167, WO2005111004, WO2005051946, US20050256114, WO2006023457, WO2006023460, US20060223858, US20060223859, WO2007107828, WO2008000483, U.S. Pat. No. 7,317,102 or WO2008041095. For example a MABA is: biphenyl-2-ylcarbamic acid 1-[2-(4-{[(R)-2-(3-formylamino-4-hydroxyphenyl)-2-hydroxyethylam-2,5-dimethylphenylcarbamoyl)ethyl]piperidin-4-yl ester; or succinic acid salt and 1,2-ethanedisulfonic of biphenyl-2-ylcarbamic acid 1-[2-(2-chloro-4-{[(R)-2-hydroxy-2-(8-hydroxy-2-oxo-1,2-dihydroquinolin-5-yl)ethylmino]methyl}-5-methoxyphenylcarbamoyl)ethyl]piperidin-4-yl ester; or naphthalene-1,5-disulfonic acid salt of biphenyl-2-ylcarbamic acid 1-(9-[(R)-2-hydroxy-2-(8-hydroxy-2-oxo-1,2-dihydro-quinolin-5-yl)ethylamino]nonyl}piperidin-4-yl ester or N-{5-[(1R)-2-((2-[4-(2-{3-[(1R)-3-(diisopropylamino)-1-phenylpropyl]-4-hydroxyphenyl}ethoxy)-phenyl]ethyl}amino)-1-hydroxyethyl]-2-hydroxyphenyl}methanesulfonamide optionally as the succinate salt.

In one embodiment of the present invention, the second active ingredient is [1-[3-[2-chloro-4-[[[(2R)-2-hydroxy-2-(8-hydroxy-2-oxo-1H-quinolin-5-yl)ethyl]amino]methyl]-5-methoxy-anilino]-3-oxo-propyl]-4-piperidyl]N-(2-phenylphenyl)carbamate or a pharmaceutically acceptable salt thereof. This chemical name is an IUPAC name (Lexichem).

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1 (2H)-pyrazinyl]-benzamide or a salt thereof and a second active ingredient is a corticosteroid.

In one embodiment of the present invention, the second active ingredient is a corticosteroid selected from alclometasone dipropionate, amelometasone, beclomethasone dipropionate, budesonide, butixocort propionate, biclesonide, blobetasol propionate, desisobutyrylciclesonide, dtiprednol dicloacetate, fluocinolone acetonide, fluticasone Furoate, fluticasone propionate, loteprednol etabonate (topical) or mometasone furoate.

In a further embodiment, the second active ingredient is a corticosteroid selected from triamcinolone acetonide (Pregna-1,4-diene-3,20-dione, 9-fluoro-11,21-dihydroxy-16,17-[(1-methylethylidene)bis(oxy)]-, (11.beta., 16.alpha.)-), QAE397, prednisone (Pregna-1,4-diene-3,11,20-trione, 17,21-dihydroxy-), mometasone furoate (Pregna-1,4-diene-3,20-dione, 9,21-dichloro-17-[(2-furanylcarbonyl)oxy]-11-hydroxy-16-methyl-, (11.beta., 16.alpha.)-), loteprednol etabonate (Androsta-1,4-diene-17-carboxylic acid, 17-[(ethoxycarbonyl)oxy]-11-hydroxy-3-oxo-, chloromethyl ester, (1), fluticasone propionate (Androsta-1,4-diene-17-carbothioic acid, 6,9-difluoro-1'-hydroxy-16-methyl-3-oxo-17-(1-oxopropoxy)-, S-(fluoromethyl) ester, (6.alpha., 11.beta., 16.alpha., 17.alpha.)-), fluticasone furoate (Androsta-1,4-diene-17-carbothioic acid, 6,9-difluoro-17-[(2-furanylcarbonyl)oxy]-11-hydroxy-16-methyl-3-oxo-, S-(fluoromethyl) ester, (6.alpha., 11.beta., 16.alpha., 17.alpha.)-), fluocinolone acetonide (Pregna-1,4-diene-3,20-dione, 6,9-difluoro-11,21-dihydroxy-16,17-[(1-methylethylidene)bis(oxy)]-, (6.alpha., 11.beta., 16.alpha.)-), dexamethasone cipecilate (Pregna-1,4-diene-3,20-dione, 21-[(cyclohexylcarbonyl)oxy]-17-[(cyclopropylcarbonyl)oxy]-9-fluoro-11-hydroxy-16-methyl-, (11.beta., 16.alpha.)-), desisobutyryl ciclesonide (Pregna-1,4-diene-3,20-dione, 16,17-[[(R)-cyclohexylmethylene]bis(oxy)]-11,21-dihydroxy-, (11.beta., 16.alpha.)-), clobetasol propionate (Pregna-1,4-diene-3,20-dione, 21-chloro-9-fluoro-11-hydroxy-16-methyl-17-(1-oxopropoxy)-, (11.beta.,16.beta.)-), ciclesonide (Pregna-1,4-diene-3,20-dione, 16,17-[[(R)-cyclohexylmethylene]bis(oxy)]-11-hydroxy-21-(2-methyl-1-oxopropoxy)-, (11.beta.,16.alpha.)-), butixocort propionate (Pregn-4-ene-3,20-dione, 11-hydroxy-17-(1-oxobutoxy)-21-[(1-oxopropyl)thio]-, (11.beta.)-), budesonide (Pregna-1,4-diene-3,20-dione, 16,17-[butylidenebis(oxy)]-11,21-dihydroxy-, (11.beta., 16.alpha.)-), beclomethasone dipropionate (Pregna-1,4-diene-3,20-dione, 9-chloro-1'-hydroxy-16-methyl-17,21-bis(1-oxopropoxy)-, (11.beta.,16.beta.)-), alclometasone dipropionate (Pregna-1,4-diene-3,20-dione, 7-chloro-1'-hydroxy-16-methyl-17,21-bis(1-oxopropoxy)-, (7.alpha.,11.beta.,16.alpha.)-), GSK870086, PF-251802 or PF-4171327.

In one embodiment, the second active ingredient is dexamethasone.

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof and a second active ingredient which is a non-steroidal Glucocorticoid Receptor (GR Receptor) Agonist.

A non-steroidal glucocorticoid receptor (GR) agonist is, for example, a compound disclosed in WO2008/076040, for example 2,2,2-Trifluoro-N-[(1R,2S)-1-[1-(4-fluorophenyl)indazol-5-yl]oxy-1-(3-methoxyphenyl)propan-2-yl]acetamide, N-[(1R,2S)-1-[1-(4-fluorophenyl)indazol-5-yl]oxy-1-(4-methylsulfonylphenyl)propan-2-yl]-2-hydroxyacetamide, N-[(1R*,2S*)-1-[1-(4-fluorophenyl)indazol-5-yl]oxy-1-(6-methoxypyridin-3-yl)propan-2-yl]cyclopropanecarboxamide, (2S)—N-[(1R,2S)-1-[1-(4-fluorophenyl)indazol-5-yl]oxy-1-phenyl-propan-2-yl]-2-hydroxy-propanamide, 2,2,2-Trifluoro-N-[(2S*,3S*)-3-[1-(4-fluorophenyl)indazol-5-yl]oxy-4-phenoxy-butan-2-yl]acetamide, N-[(1R,2S)-1-[1-(4-Fluorophenyl)indazol-5-yl]oxy-1-(3-methoxyphenyl)propan-2-yl]-N-propan-2-yl-oxamide, or a pharmaceutically acceptable salt thereof.

In one embodiment, the second active ingredient is 2,2,2-trifluoro-N-[(1R,2S)-1-[1-(4-fluorophenyl)indazol-5-yl]oxy-1-(3-methoxyphenyl)propan-2-yl]acetamide or a pharmaceutically acceptable salt thereof. This compound is described in WO2008/076048.

It is known that glucocorticoids, both endogenous and man-made/synthetic non-steroidal molecules can exert anti-inflammatory and immunosuppressive activity through binding to the glucocorticoid receptor. This receptor is a member of the steroid hormone receptor family of transcription factors which has a role in regulating human physiology such as inflammation as well as immune responses. In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof and a second active ingredient is a corticosteroid or a non-steroidal glucocorticoid receptor (GR Receptor) Agonist.

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof and a second active ingredient is an IKK2 kinase inhibitor.

An IKK2 inhibitor is, for example, 2-{[2-(2-Methylaminopyrimidin-4-yl)-1H-indole-5-carbonyl]-amino}-3-(phenylpyridin-2-yl-amino)-propionic acid or a compound as disclosed in WO 01/58890, WO 03/010158, WO 03/010163, WO 04/063185, WO 04/063186.

In one embodiment, the second active ingredient is 5-[2-[(3S)-pyrrolidin-3-yl]oxyphenyl]-2-ureido-thiophene-3-carboxamide (IUPAC name (Lexichem)

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof and a second active ingredient is a phosphodiesterase PDE4 inhibitor.

A PDE4 inhibitor is, for example, 6-fluoro-N-((1s,4s)-4-(6-fluoro-2,4-dioxo-1-(4'-(piperazin-1-ylmethyl)-biphenyl-3-yl)-1,2-dihydropyrido[2,3-d]pyrimidin-3(4H)-yl)cyclohexyl)imidazo[1,2-a]pyridine-2-carboxamide (as disclosed in. WO2008084223), or a salt thereof (for example a (1S)-(+)-10-Camphorsulfonic acid or trihydrochloride salt).

In one embodiment, the second active ingredient is 6-Fluoro-N-((1s,4s)-4-(6-fluoro-2,4-dioxo-1-(4'-(piperazin-1-ylmethyl)-biphenyl-3-yl)-1,2-dihydropyrido[2,3-d]pyrimidin-3(4H)-yl)cyclohexyl)imidazo[1,2-a]pyridine-2-carboxamide or a pharmaceutically acceptable salt thereof (e.g. (1S)-(+)-10-Camphorsulfonic acid salt) salt as described in PCT/GB2008/000061.

In one embodiment, the present invention provides a pharmaceutical product comprising, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof and a second active ingredient is an inhibitor of neutrophil elastase. Inhibitors of neutrophil elastase are a specific type of protease inhibitor.

In one embodiment, the second active ingredient is 6-[2-(4-cyano-phenyl)-2H-pyrazol-3-yl]-5-methyl-3-oxo-4-(3-trifluoromethyl-phenyl)-3,4-dihydro-pyrazine-2-carboxylic acid ethylamide. This compound is described in WO2007/129963.

Further examples of second active ingredients that may be utilised in the present invention are detailed below:—

An Adenosine A2A receptor antagonist is, for example, a compound such as UK-432097.

An antiinfective is, for example, an antibiotic such as Amoxicillin, Doxycycline, Trimethoprim sulpha, or a Cephalosporin.

An antioxidant is, for example, Allopurinol, Erdosteine, Mannitol, N-acetyl cysteine choline ester, N-acetyl cysteine ethyl ester, N-Acetylcysteine, N-Acetylcysteine amide or Niacin.

A CCR1 antagonist is, for example, a compound disclosed in WO2001/062728 or WO2001/098273, or a pharmaceutically acceptable salt thereof (such as a hydrochloride, trifluoroacetate, sulphate, (hemi)fumarate, benzoate, furoate or succinate salt).

Also, a CCR1 antagonist is, for example, N-{2-[((2S)-3-{[1-(4-chlorobenzyl)piperidin-4-yl]amino}-2-hydroxy-2-methylpropyl)oxy]-4-hydroxyphenyl}acetamide (see WO 2003/051839), or, 2-{2-Chloro-5-{[(2S)-3-(5-chloro-1'H,3H-spiro[1-benzofuran-2,4'-piperidin]-1'-yl)-2-hydroxypropyl]oxy}-4-[(methylamino)carbonyl]phenoxy}-2-methylpropanoic acid (see PCT publication no. WO 2008/010765), or a pharmaceutically acceptable salt thereof (for example a hydrochloride, sulphate, (hemi)fumarate, benzoate, furoate or succinate salt). In one embodiment the CCR1 antgonist is 4-({(2S)-3-[2-(acetylamino)-5-hydroxyphenoxy]-2-hydroxy-2-methylpropyl}ammonio)-1-(4-chlorobenzyl)piperidine (as described in WO2003/051839) or a pharmaceutically acceptable dsalt thereof. In a further embodiment, the CCR1 antagonist is 2-{2-Chloro-5-{[(2S)-3-(5-chloro-1'H,3H-spiro[1-benzofuran-2,4'-piperidin]-1'-yl)-2-hydroxypropyl]oxy}-4-[(methylamino)carbonyl]phenoxy}-2-methylpropanoic acid (as described in WO2008/010765) or a pharmaceutically acceptable salt thereof.

A chemokine antagonist (other than a CCR1 antagonist), for example, 656933 (N-(2-bromophenyl)-N'-(4-cyano-1H-1,2,3-benzotriazol-7-yl)urea), 766994 (4-({[({[(2R)-4-(3,4-dichlorobenzyl)morpholin-2-yl]methyl}amino)carbonyl]amino]methyl)benzamide), CCX-282, CCX-915, Cyanovirin N, E-921, INCB-003284, INCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) or Vicriviroc.

A chloride channel hCLCA1 blocker is, for example, as disclosed in WO2006/091112, WO2004/113286 and WO2001/038530.

A CRTh2 antagonist is, for example, a compound from WO 2004/106302, WO2004/089885, WO2005/018529 or WO2007/039741.

A DP1 antagonist is, for example, L888839 or MK0525.

An ENAC (Epithelial Sodium-channel blocker) is, for example, Amiloride, Benzamil, Triamterene, 552-02, PSA14984, PSA25569, PSA23682, AER002, Parion P-522 or a compound from WO2008031048.

A formyl peptide receptor antagonist is, for example, a compound from WO2007/144198.

A histone deacetylase activator is, for example, ADC4022, Aminophylline, a Methylxanthine or Theophylline.

An ICAM blocker is, for example, an anti-ICAM-1 monoclonal antibody (MAb) 1A6 from Antimicrobial Agents and Chemotherapy 2003, 47, 1503-1508.

A JNK inhibitor is, for example, a compound from WO2005/003123 or WO2003/051277.

A COX inhibitor is, for example, Celecoxib, Diclofenac sodium, Etodolac, Ibuprofen, Indomethacin, Meloxicam, Nimesulide, OC1768, OC2125, OC2184, OC499, OCD9101, Parecoxib sodium, Piceatannol, Piroxicam, Rofecoxib or Valdecoxib.

A lipoxygenase inhibitor is, for example, Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 or Zileuton ((±)-1-(1-Benzo[b]thien-2-ylethyl)-1-hydroxyurea)

A leukotriene receptor antagonist is, for example, Ablukast, Iralukast (CGP 45715A), Montelukast, Montelukast sodium, Ontazolast, Pranlukast, Pranlukast hydrate (mono Na salt), Verlukast (MK-679) or Zafirlukast.

A MEK-1 inhibitor is, for example, a compound disclosed in WO2007123939, WO2007025090 or WO2005051906.

An MPO Inhibitor is, for example, a Hydroxamic acid derivative (N-(4-chloro-2-methyl-phenyl)-4-phenyl-4-[[(4-propan-2-ylphenyl)sulfonylamino]methyl]piperidine-1-carboxamide), Piceatannol or Resveratrol, or a compound disclosed within U.S. Pat. No. 7,425,560, WO2003/089430, WO2006/062465 and WO2007/120098.

A PI 3 kinase γ inhibitor is, for example, a compound from WO2005/105801, WO2003/072557, and WO2007/082956.

A PPARγ agonist is, for example, Pioglitazone, Pioglitazone hydrochloride, Rosiglitazone Maleate, Rosiglitazone Maleate ((−)-enantiomer, free base), Rosiglitazone maleate/Metformin hydrochloride or Tesaglitizar.

A Protease Inhibitor is, for example, Alpha1-antitrypsin proteinase Inhibitor, EPI-HNE4, UT-77, ZD-0892 or a compound from WO 2006/004532, WO 2005/026123, WO 2002/0744767 or WO 22002/074751; or a TACE Inhibitor (for example DPC-333, Sch-709156 or Doxycycline); inhibitors of cathepsins for example inhibitors of cathepsin S (for example as disclosed in WO2002/14314), cathepsin L (for example as described within Bioorg. Med. Chem. 2004, 12, 4081), cathepsin K (for example WO 2001/47886), cathepsin B (for example tokaramide A and leupetin) and cathepsin C (dipeptidyl peptidase 1) (for example a compound from WO 2005/000800); inhibitors of neutrophil elastase, for example as disclosed in WO2005/026123 and WO2007/129963 (for example 6-[1-(4-cyanophenyl)-1H-pyrazol-5-yl]-N,5-dimethyl-3-oxo-4-[3-(trifluoromethyl)phenyl]-3,4-dihydropyrazine-2-carboxamide) and inhibitors of matrix metallo proteinases (for example ABT-518 or Ro-32-7315).

A RAR γ modulator (Retinoic acid gamma receptor modulator) is, for example, palovarotene (R667), a compound disclosed in WO2008064136 (agonists) or WO2006066978 (antagonists).

A Statin is, for example, Atorvastatin, Lovastatin, Pravastatin, Rosuvastatin or Simvastatin.

A Thromboxane Antagonist is, for example, Ramatroban or Seratrodast.

A Vasodilator is, for example, A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril), Liposomal treprostinil, PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine or Treprostinil sodium.

All the above second et seq active ingredients may be in the form of solvates, for example hydrates.

In one particular aspect the present invention provides a pharmaceutical product comprising the first and second active ingredients in admixture. Alternatively, the pharmaceutical product may, for example, be a kit comprising a preparation of the first active ingredient and a preparation of the second active ingredient and, optionally, instructions for the simultaneous, sequential or separate administration of the preparations to a patient in need thereof.

In another aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide and a second active ingredient selected from:

$\beta_2$ adrenoceptor agonist;
a MABA compound; or,
a muscarinic antagonist.

In a further aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt)); a second active ingredient and a third active ingredient, wherein the second and third active ingredients are selected from the active ingredients described hereto as second active ingredients.

In yet another aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt); a second active ingredient that is a $\beta_2$ adrenoceptor agonist; and, optionally, a third active ingredient that is selected from:
a non-steroidal Glucocorticoid Receptor (GR Receptor) Agonist;
a CCR1 antagonist;
a chemokine antagonist (not CCR1);
a corticosteroid;
an IKK2 inhibitor;
a muscarinic antagonist;
an inhibitor of neutrophil elastase or,
PDE4 inhibitor.

In yet another aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt)); a second active ingredient that is a MABA compound; and, optionally, a third active ingredient that is selected from:
a non-steroidal Glucocorticoid Receptor (GR Receptor) Agonist;
a CCR1 antagonist;
a chemokine antagonist (not CCR1);
a corticosteroid;
a non-steroidal Glucocorticoid Receptor (GR Receptor) Agonist;
an IKK2 inhibitor;
an inhibitor of neutrophil elastase or,
PDE4 inhibitor.

In a further aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt)); a second active ingredient that is a muscarinic antagonist; and, optionally, a third active ingredient that is selected from:
a non-steroidal Glucocorticoid Receptor (GR Receptor) Agonist;
a CCR1 antagonist;
a chemokine antagonist (not CCR1);
a corticosteroid;
a non-steroidal Glucocorticoid Receptor (GR Receptor) Agonist
an IKK2 inhibitor;
an inhibitor of neutrophil elastase; or,
a PDE4 inhibitor.

In another aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt), and a second active ingredient is a MABA compound having dual activity as both a muscarinic antagonist and as a $\beta_2$-adrenoceptor agonist, for example a MABA is a compound disclosed in: WO2004089892, WO2004106333, US20040167167, WO2005111004, WO2005051946, WO2006023457, WO2006023460, US20060223858, US20060223859, WO2007107828, WO2008000483, U.S. Pat. No. 7,317,102 or WO2008041095. For example the MABA is: biphenyl-2-ylcarbamic acid 1-[2-(4-{[(R)-2-(3-formylamino-4-hydroxyphenyl)-2-hydroxyethylam-2,5-dimethylphenylcarbamoyl)ethyl]piperidin-4-yl ester; or succinic acid salt and 1,2-ethanedisulfonic of biphenyl-2-ylcarbamic acid 1-[2-(2-chloro-4-{[(R)-2-hydroxy-2-(8-hydroxy-2-oxo-1,2-dihydroquinolin-5-yl)ethylmino]methyl}-5-methoxyphenylcarbamoyl)ethyl]piperidin-4-yl ester; or naphthalene-1,5-disulfonic acid salt of biphenyl-2-ylcarbamic acid 1-(9-[(R)-2-hydroxy-2-(8-hydroxy-2-oxo-1,2-dihydro-quinolin-5-yl)ethylamino]nonyl}piperidin-4-yl ester.

In another aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt), and a second active ingredient is a muscarinic antagonist, for example, Aclidinium bromide, Glycopyrrolate (such as R,R-, R,S-, S,R-, or S,S-glycopyrronium bromide), Oxitropium bromide, Pirenzepine, telenzepine, Tiotropium bromide, Darotropium ((1R,3R,5S)-3-(2-cyano-2,2-diphenylethyl)-8,8-dimethyl-8-azoniabicyclo[3,2,1]octane bromide), 3(R)-(2-hydroxy-2,2-dithien-2-ylacetoxy)-1-(3-phenoxypropyl)-1-azoniabicyclo[2.2.2]octane bromide (see WO 01/04118), or 3(R)-1-phenethyl-3-(9H-xanthene-9-carbonyloxy)-1-azoniabicyclo[2.2.2]octane bromide or (3R)-3-[(2S)-2-cyclopentyl-2-hydroxy-2-thien-2-ylacetoxy]-1-(2-phenoxyethyl)-1-azoniabicyclo[2.2.2]actane bromide (see WO 01/04118); or a quaternary ammonium salt (such as [2-((S)-Cyclohexyl-hydroxy-phenyl-methyl)-oxazol-5-ylmethyl]-dimethyl-(3-phenoxy-propyl)-ammonium salt, [2-((R)-Cyclohexyl-hydroxy-phenyl-methyl)-oxazol-5-ylmethyl]-dimethyl-(3-phenoxy-propyl)-ammonium salt, [2-((R)-Cyclohexyl-hydroxy-phenyl-methyl)-oxazol-5-ylmethyl]-dimethyl-(2-phenethyloxy-ethyl)-ammonium salt, [2-((R)-Cyclohexyl-hydroxy-phenyl-methyl)-oxazol-5-ylmethyl]-[3-(3,4-dichloro-phenoxy)-propyl]dimethyl-ammonium salt, [2-((R)-Cyclohexyl-hydroxy-phenyl-methyl)-oxazol-5-ylmethyl]-[2-(3,4-dichloro-benzyloxy)-ethyl]-dimethyl-ammonium salt, [2-(4-Chloro-benzyloxy)-ethyl]-[2-((R)-Cyclohexyl-hydroxy-phenyl-methyl)-oxazol-5-ylmethyl]-dimethyl-ammonium salt, or (R)-1-[2-(4-Fluoro-phenyl)-ethyl]-3-((S)-2-phenyl-2-piperidin-1-yl-propionyloxy)-1-azonia-bicyclo[2.2.2]octane; wherein the counter-ion is, for example, chloride, bromide, sulfate, methanesulfonate, benzenesulfonate (besylate), toluenesulfonate (tosylate), napthalenebissulfonate (napadisylate), phosphate, acetate, citrate, lactate, tartrate, mesylate, maleate, fumarate or succinate.

In a further aspect the present invention provides a pharmaceutical product comprising, in combination, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt), and a second active ingredient is Oxitropium bromide, Tiotropium bromide, Aclidinium bromide, Glycopyrrolate (such as R,R-, R,S-, S,R-, or S,S-glycopyrronium bromide) or Darotropium ((1R,3r,5S)-3-(2-cyano-2,2-diphenylethyl)-8,8-dimethyl-8-azoniabicyclo[3,2,1]octane bromide).

In one aspect of the invention the muscarinic receptor antagonist is a long acting muscarinic receptor antagonist, that is a muscarinic receptor antagonist with activity that persists for more than 12 hours. Examples of long acting muscarinic receptor antagonists include tiotropium bromide.

In another aspect the present invention provides a pharmaceutical product comprising, in combination, a first active ingredient which is N-cyclopropyl-3-fluoro-4-methyl-5-[3-

[[1-[2-[2-(methylamino)ethoxy]phenyl]cyclopropyl]amino]-2-oxo-1(2H)-pyrazinyl]-s benzamide or a salt thereof (such as the hydrochloride or L-tartaric acid salt), and a second active ingredient is Tiotropium bromide.

The first active ingredient and the second active ingredient of the pharmaceutical product of the present invention may be administered simultaneously, sequentially or separately to treat respiratory diseases. By simultaneously is meant that the active ingredients are in admixture, or they could be in separate chambers of the same inhaler. By sequential it is meant that the active ingredients are administered, in any order, one immediately after the other. They still have the desired effect if they are administered separately, but when administered in this manner they are generally administered less than 4 hours apart, conveniently less than two hours apart, more conveniently less than 30 minutes apart and most conveniently less than 10 minutes apart, for example less than 10 minutes but not one immediately after the other.

The active ingredients may be delivered to the lung and/or airways via oral administration in the form of a solution, suspension, aerosol or dry powder formulation. These dosage forms will usually include one or more pharmaceutically acceptable ingredients which may be selected, for example, from an adjuvant, carrier, binder, lubricant, diluent, stabilising agent, buffering agent, emulsifying agent, viscosity-regulating agent, surfactant, preservative, flavouring or colorant. The active ingredients of the present invention may also be administered by oral or parenteral (e.g. intravenous, subcutaneous, intramuscular or intraarticular) administration using conventional systemic dosage forms, such as tablets, capsules, pills, powders, aqueous or oily solutions or suspensions, emulsions and sterile injectable aqueous or oily solutions or suspensions. As will be understood by those skilled in the art, the most appropriate method of administering the active ingredients is dependent on a number of factors.

In another embodiment the first and second active ingredients are administered via a single pharmaceutical composition (that is, the first and second active ingredients are in admixture). Therefore, the present invention further provides a pharmaceutical composition comprising, in admixture, a first active ingredient which is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof (such as the hydrochloride or L-tartaric acid salt), and a second active ingredient as defined above. The pharmaceutical composition optionally further comprises a pharmaceutically acceptable adjuvant, diluent or carrier.

The pharmaceutical compositions of the present invention can be prepared by mixing the first active ingredient with the second active ingredient and a pharmaceutically acceptable adjuvant, diluent or carrier. Therefore, in a further aspect of the present invention there is provided a process for the preparation of a pharmaceutical composition, which comprises mixing the first and second active ingredients and a pharmaceutically acceptable adjuvant, diluent or carrier.

It will be understood that the therapeutic dose of each active ingredient administered in accordance with the present invention will vary depending upon the particular active ingredient employed, the mode by which the active ingredient is to be administered, and the condition or disorder to be treated.

In one embodiment of the present invention, the first active ingredient is administered via inhalation. When administered via inhalation the dose of the first active ingredient (that is N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide in: salt form, solvate form, or, solvate of salt form) will generally be in the range of from 0.1 microgram (µg) to 5000 µg, 0.1 to 1000 µg, 0.1 to 500 µg, 0.1 to 100 µg, 0.1 to 50 µg, 0.1 to 5 µg, 5 to 5000 µg, 5 to 1000 µg, 5 to 500 µg, 5 to 100 µg, 5 to 50 µg, 5 to 10 µg, 10 to 5000 µg, 10 to 1000 µg, 10 to 500 µg, 10 to 100 µg, 10 to 50 µg, 20 to 5000 µg, 20 to 1000 µg, 20 to 500 µg, 20 to 100 µg, 20 to 50 µg, 50 to 5000 µg, 50 to 1000 µg, 50 to 500 µg, 50 to 100 µg, 100 to 5000 µg, 100 to 1000 µg or 100 to 500 µg. The dose will generally be administered from 1 to 4 times a day, conveniently once or twice a day, and most conveniently once a day.

In one embodiment of the present invention the second active ingredient is administered by inhalation. When administered via inhalation the dose of the second active ingredient will generally be in the range of from 0.1 microgram (µg) to 5000 µg, 0.1 to 1000 µg, 0.1 to 500 µg, 0.1 to 100 µg, 0.1 to 50 µg, 0.1 to 5 µg, 5 to 5000 µg, 5 to 1000 µg, 5 to 500 µg, 5 to 100 µg, 5 to 50 µg, 5 to 10 µg, 10 to 5000 µg, 10 to 1000 µg, 10 to 500 µg, 10 to 100 µg, 10 to 50 µg, 20 to 5000 µg, 20 to 1000 µg, 20 to 500 µg, 20 to 100 µg, 20 to 50 µg, 50 to 5000 µg, 50 to 1000 µg, 50 to 500 µg, 50 to 100 µg, 100 to 5000 µg, 100 to 1000 µg or 100 to 500 µg. The dose will generally be administered from 1 to 4 times a day, conveniently once or twice a day, and most conveniently once a day.

In another embodiment the present invention provides a pharmaceutical product wherein the molar ratio of first active ingredient to second active ingredient is from 1:1000 to 1000:1, such as from 1:100 to 100:1, for example from 1:50 to 50:1, for example 1:20 to 20:1.

In one embodiment, the present invention provides a pharmaceutical product comprising, in combination, a first active ingredient as defined above, and a second active ingredient as defined above, wherein each active ingredient is formulated for inhaled administration. In a further aspect of this embodiment, the pharmaceutical product is in the form of a pharmaceutical composition comprising the first and second active ingredients in admixture, and which composition is formulated for inhaled administration.

The active ingredients of the present invention are conveniently delivered via oral administration by inhalation to the lung and/or airways in the form of a solution, suspension, aerosol or dry powder (such as an agglomerated or ordered mixture) formulation. For example a metered dose inhaler device may be used to administer the active ingredients, dispersed in a suitable propellant and with or without an additional excipient such as ethanol, a surfactant, lubricant or stabilising agent. A suitable propellant includes a hydrocarbon, chlorofluorocarbon or a hydrofluoroalkane (e.g. heptafluoroalkane) propellant, or a mixture of any such propellants, for example in a pressurised metered dose inhaler (pMDI). Preferred propellants are P134a and P227, each of which may be used alone or in combination with other another propellant and/or surfactant and/or other excipient. A nebulised aqueous suspension or, preferably, solution may also be employed, with or without a suitable pH and/or tonicity adjustment, either as a unit-dose or multi-dose formulation. A suitable device for delivering a dry powder is Turbuhaler®.

The pharmaceutical product of the present invention can, for example, be administered: via an inhaler having the first and second active ingredients in separate chambers of the inhaler such that on administration the active ingredients mix in either the mouthpiece of the inhaler or the mouth of a patient or both (for simultaneous use); or, where the first and second active ingredients are in separate inhalers, via separate inhalers (for separate or sequential use); or the first and second active ingredients are in admixture in an inhaler when the inhaler is supplied to a patient (for simultaneous use).

A dry powder inhaler may be used to administer the active ingredients, alone or in combination with a pharmaceutically acceptable carrier (such as lactose), in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices is available.

The combination of the present invention may be used to treat diseases of the respiratory tract such as obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

Accordingly, the present invention further provides a pharmaceutical product according to the invention for simultaneous, sequential or separate use in therapy.

The present invention further provides the use of a pharmaceutical product according to the invention in the manufacture of a medicament for the treatment of a respiratory disease, in particular chronic obstructive pulmonary disease, asthma, rhinitis, emphysema or bronchitis (such as chronic obstructive pulmonary disease or asthma; for example chronic obstructive pulmonary disease).

The present invention still further provides a method of treating a respiratory disease which comprises simultaneously, sequentially or separately administering:
(a) a therapeutically effective dose of a first active ingredient as defined above; and,
(b) a therapeutically effective dose of a second active ingredient as defined above; to a patient in need thereof.

In a further aspect the present invention provides the use of a pharmaceutical product, kit or composition as hereinbefore described for the treatment of a respiratory disease, in particular chronic obstructive pulmonary disease, asthma, rhinitis, emphysema or bronchitis (such as chronic obstructive pulmonary disease or asthma; for example chronic obstructive pulmonary disease).

In the context of the present specification, the term "therapy" also includes "prophylaxis" unless there are specific indications to the contrary. The terms "therapeutic" and "therapeutically" should be construed accordingly. Prophylaxis is expected to be particularly relevant to the treatment of persons who have suffered a previous episode of, or are otherwise considered to be at increased risk of, the condition or disorder in question. Persons at risk of developing a particular condition or disorder generally include those having a family history of the condition or disorder, or those who have been identified by genetic testing or screening to be particularly susceptible to developing the condition or disorder.

In one aspect, the present invention provides for the use of a product according to the invention in therapy.

In one aspect, the present invention provides for the use of a product according to the invention in the manufacture of a medicament for the treatment of a respiratory disease.

In one aspect, the present invention provides for the use of a product according to the invention in the manufacture of a medicament for the treatment of chronic obstructive pulmonary disease.

In one aspect, the present invention provides for the use of a product according to the invention in the manufacture of a medicament for the treatment of asthma.

In one aspect, the present invention provides a method of treating a respiratory disease, which method comprises simultaneously, sequentially or separately administering:
(a) a (therapeutically effective) dose of a first active ingredient according to the present invention; and
(b) a (therapeutically effective) dose of a second active ingredient according to the present invention.
to a patient in need thereof.

In one embodiment, the present invention provides a kit comprising a preparation of a first active ingredient which is, a preparation of a second active ingredient which is, and optionally instructions for the simultaneous, sequential or separate administration of the preparations to a patient in need thereof.

In one embodiment, the present invention provides a pharmaceutical composition comprising, in admixture, a first active ingredient which is N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof, and a second active ingredient which is selected from:
an Adenosine A2A receptor antagonist;
an anti-infective;
a non-steroidal Glucocorticoid Receptor (GR Receptor) Agonist;
an antioxidant;
a $\beta_2$ adrenoceptor agonist;
a CCR1 antagonist;
a chemokine antagonist (not CCR1);
a corticosteroid;
a CRTh2 antagonist;
a DP1 antagonist;
a formyl peptide receptor antagonist;
a Histone Deacetylase activator;
a chloride channel hCLCA1 blocker
an Epithelial sodium channel blocker (ENAC blocker)).
an Inter-cellular adhesion molecule 1 blocker (ICAM blocker);
an IKK2 kinase inhibitor;
a JNK kinase inhibitor;
a cyclooxygenase inhibitor (COX inhibitor);
a lipoxygenase inhibitor;
a leukotriene receptor antagonist;
a dual $\beta_2$ adrenoceptor agonist/$M_3$ receptor antagonist (MABA compound);
a MEK-1 kinase inhibitor
a myeloperoxidase inhibitor (MPO inhibitor);
a muscarinic antagonist;
a phosphodiesterase PDE4 inhibitor;
a phosphatidylinositol 3 (PI3)-kinase γ inhibitor (PI 3 kinase γ inhibitor)

a peroxisome proliferator activated receptor agonist (PPARγ agonist);
a protease inhibitor;
a retinoic acid receptor modulator (RAR μmodulator)
a Statin;
a thromboxane antagonist, or
a vasodilator.

DESCRIPTION OF FIGURES

FIG. 1: Effect of the combination of Compound A and Compound B on LPS stimulated TNFα production from human PBMC FIG. 2: Effect of the combination of Compound A and Compound C on LPS stimulated TNFα production from human PBMC FIG. 3: Effect of the combination of Compound A and Compound D on LPS stimulated TNFα production from human PBMC FIG. 4: Effect of the combination of Compound A and Compound E on LPS stimulated TNFα production from human PBMC FIG. 5: Effect of the combination of Compound A and Compound F on LPS stimulated TNFα production from human PBMC FIG. 6: Effect of the combination of Compound A and Compound G on LPS stimulated TNFα production from human PBMC FIG. 7: Effect of the combination of Compound A and Compound H on LPS stimulated TNFα production from human PBMC FIG. 8: Effect of the combination of Compound A and Compound I on LPS stimulated TNFα production from human PBMC FIG. 9: Effect of the combination of Compound A and Compound J on LPS stimulated TNFα production from human PBMC FIG. 10: Effect of the combination of Compound A and Compound K on LPS stimulated TNFα production from human PBMC FIG. 11: Effect of the combination of Compound A and Compound L on LPS stimulated TNFα production from human PBMC FIG. 12: Effect of the combination of Compound A and Compound M on LPS stimulated TNFα production from human PBMC FIG. 13: Effect of the combination of Compound A and Compound N on LPS stimulated TNFα production from human PBMC FIG. 14: Effect of the combination of Compound A and Compound O on LPS stimulated TNFα production from human PBMC FIG. 15: Effect of the combination of Compound A and Compound P on LPS stimulated TNFα production from human PBMC FIG. 16: Effect of the combination of Compound A and Compound Q on LPS stimulated TNFα production from human PBMC FIG. 17: Effect of the combination of Compound A and Compound R on LPS stimulated TNFα production from human PBMC FIG. 101: X-ray powder diffraction pattern of Crystalline Form A of Preparation 1 free base FIG. 102: X-ray powder diffraction pattern of Crystalline Form A of Preparation 2 dihydrochloride salt FIG. 103: X-ray powder diffraction pattern of Crystalline Form A of Preparation 3 L-Tartrate Salt FIG. 104: Cumulative concentration-response curves to Compound C in the presence of vehicle and Compound A (4 nM) in guinea pig trachea in vitro FIG. 105: Cumulative concentration-response curves to Compound E in the presence of vehicle and Compound A (4 nM) in guinea pig trachea in vitro FIG. 106: Cumulative concentration-response curves to Compound H in the presence of vehicle and Compound A (4 nM) in guinea pig trachea in vitro FIG. 107: Cumulative concentration-response curves to methacholine in the presence of vehicle, Compound D (3 nM) and a combination of Compound D (4 nM) and Compound A (4 nM) in guinea pig trachea in vitro FIG. 108: Cumulative concentration-response curves to methacholine in the presence of vehicle, Compound J (3 nM) and a combination of Compound J (3 nM) and Compound A (4 nM) in guinea pig trachea in vitro FIG. 109: Cumulative concentration-response curves to methacholine in the presence of vehicle, Compound K (2 nM) and a combination of Compound K (2 nM) and Compound A (4 nM) in guinea pig trachea in vitro FIG. 110: Cumulative concentration-response curves to methacholine in the presence of vehicle, Compound M (1 nM) and a combination of Compound M (1 nM) and Compound A (4 nM) in guinea pig trachea in vitro FIG. 111: Effect of the combination of Compound A and Dexamethasone (DEX) on LPS-stimulated production of IL-6 from COPD Alveolar Macrophages (Panel a): and Effect of the combination of Compound A and Dexamethasone (DEX) on LPS-stimulated production of TNFα from COPD Alveolar Macrophages (Panel b)

GENERAL PREPARATIVE METHODS

There follow methods for the preparation of certain compounds recited above.

$^1$H NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column or Phenomenex Gemini® using 0.1% aqueous trifluoroacetic acid: acetonitrile, 0.1% aqueous ammonia: acetonitrile or 0.1% ammonium acetate: acetonitrile as the eluent.

XRPD data were collected using a PANalytical CubiX PRO machine.

XRPD—PANalytical CubiX PRO

Data was collected with a PANalytical CubiX PRO machine in θ-2θ configuration over the scan range 2° to 40° 2θ with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC thermograms were measured using a TA Q1000 Differential Scanning calorimeter, with aluminium pans and pierced lids. The sample weights varied between 0.5 to 5 mg. The procedure was carried out under a flow of nitrogen gas (50 mL/min) and the temperature studied from 25 to 300° C. at a constant rate of temperature increase of 10° C. per minute.

GVS profiles were measured using a Dynamic Vapour Sorption DVS-1 instrument. The solid sample ca. 1-5 mg was placed into a glass vessel and the weight of the sample was recorded during a dual cycle step method (40 to 90 to 0 to 90 to 0% relative humidity (RH), in steps of 10% RH).

The following abbreviations have been used:

| DMF | N,N-dimethylformamide |
| DMSO | dimethylsulphoxide |
| THF | tetrahydrofuran |
| DMA | N,N-dimethylacetamide |
| DCM | dichloromethane |
| TBME | tert-butyl methyl ether |

Preparation 1

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide

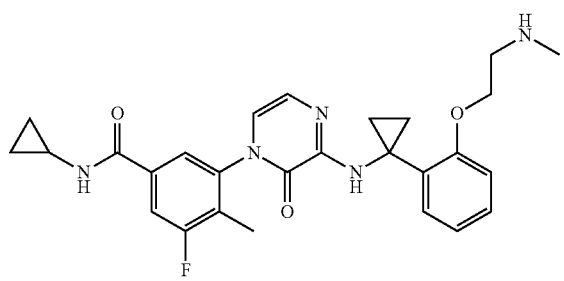 [SMILES: CNCCOc1ccccc1C1(Nc2nccn(-c3cc(C(=O)NC4CC4)cc(F)c3C)c2=O)CC1]

a) 2-Chloro-5-fluoro-4-methyl-benzoic acid methyl ester

To a solution of 1-bromo-2-chloro-5-fluoro-4-methylbenzene (70 g) dissolved in ethyl acetate (400 mL) was added N,N-diisopropylethylamine (161 mL), dichloro[1,1'-bis(diphenylphosphino)ferrocene]palladium(II) dichloromethane adduct (5.15 g) and methanol (120 mL). The resulting mixture was stirred at 90° C. for 24 h under carbon monoxide (4 bar) in a 1.5 L autoclave. Further dichloro[1,1'-bis(diphenylphosphino)ferrocene]palladium(II) dichloromethane adduct (2.57 g) was added and the reaction heated at 90° C. for a further 3 h. The cooled reaction mixture was evaporated to dryness and the residue purified by silica chromatography, eluting with 50% dichloromethane in iso-hexane to give the subtitle compound (57.7 g).

$^1$H NMR δ (DMSO-$d_6$) 7.64–7.50 (m, 2H), 3.90 (s, 3H), 2.31 (s, 3H).

b) 2-Chloro-5-fluoro-4-methyl-benzoic acid

A solution of 2-chloro-5-fluoro-4-methyl-benzoic acid methyl ester (Preparation 1a, 57.77 g) in methanol (400 mL) was treated with sodium hydroxide 2 M solution (285 mL) under nitrogen. The resulting mixture was stirred at 25° C. for 1 h. The reaction mixture was extracted with diethyl ether (discarded) and the aqueous layer diluted with 2 M hydrochloric acid (250 mL). The reaction mixture was extracted with ethyl acetate (500 mL). The combined organics were dried (MgSO$_4$), filtered and evaporated to afford the subtitle compound (51.6 g).

$^1$H NMR δ (DMSO-$d_6$) 13.66 (s, 1H), 7.68–7.39 (m, 2H), 2.36 (s, 3H).

c) 2-Chloro-5-fluoro-4-methyl-3-nitro-benzoic acid

A solution of 2-chloro-5-fluoro-4-methylbenzoic acid (Preparation 1b, 51.57 g) dissolved in conc sulfuric acid (143 mL) was treated with potassium nitrate (32.4 g) portionwise over 10 min at 0° C. under nitrogen. The resulting mixture was allowed to warm to room temperature before stirring at 50° C. for 1 h. The reaction mixture was quenched with ice water and the precipitate was collected and dried in vacuo to afford the subtitle compound (65.5 g).

$^1$H NMR δ (DMSO-$d_6$) 7.94 (d, 1H), 2.26 (s, 3H).

d) 2-Chloro-5-fluoro-4-methyl-3-nitro-benzoic acid methyl ester

A solution of chlorotrimethylsilane (200 mL) in methanol (300 mL) was treated with 2-chloro-5-fluoro-4-methyl-3-nitrobenzoic acid (Preparation 1c, 65.5 g) portionwise under nitrogen. The resulting solution was stirred at 20° C. for 16 h. Further chlorotrimethylsilane (100 mL) was added and the reaction heated at 50° C. for 6 h. The reaction mixture was evaporated to afford crude product which was diluted with water and extracted with ethyl acetate (300 mL). The organic extract was dried (MgSO$_4$), filtered and evaporated to afford the subtitle compound (53.4 g).

1H NMR δ (DMSO-$d_6$) 7.99 (d, 1H), 4.00 (s, 3H), 2.35 (s, 3H).

e) 3-Amino-5-fluoro-4-methyl-benzoic acid methyl ester

2-Chloro-5-fluoro-4-methyl-3-nitro-benzoic acid methyl ester (Preparation 1d, 53 g), 5% Pd/C (9 g) and ammonium formate (80 g) were stirred together in ethanol (500 mL) at 75° C. for 32 h. The reaction was filtered through celite and filtrate evaporated to a solid. This solid residue was dissolved in dichloromethane, washed with water. The separated aqueous layer was further extracted with dichloromethane (3×100 mL) and the combined organics dried (MgSO4) and evaporated. Analysis showed significant unreacted starting material. The reaction was repeated by new 5% P/C (9 g) and ammonium formate (80 g) together in ethanol (500 mL) and heating at 75° C. for 20 h. Further 5% Pd/C (9 g) and ammonium formate (80 g) were added and heating continued for 10 h. The mixture was filtered through celite and the filter cake was washed with further ethanol. The combined filtrates were evaporated, the residue dissolved in dichloromethane, washed with water. The separated aqueous layer was further extracted with dichloromethane (3×100 mL) and the combined organics dried (MgSO$_4$) and evaporated to afford the subtitle compound (34.7 g).

$^1$H NMR δ (CDCl$_3$) 7.15 (s, 1H), 7.12 (dd, 1H), 3.88 (s, 3H), 2.10 (d, 3H).

f) 3-[(Cyanomethyl)amino]-5-fluoro-4-methyl-benzoic acid, methyl ester

To a stirred solution of 3-amino-5-fluoro-4-methyl-benzoic acid methyl ester (Preparation 1e, 34.7 g) in THF (300 mL) at room temperature was added N,N-diisopropylethylamine (61.2 mL) followed by bromoacetonitrile (24.41 mL). The mixture was heated at reflux for 16 h, further bromoacetonitrile (4.8 mL) and N,N-diisopropylethylamine (12.5 mL) were added and heating was continued for 6 h. The reaction was cooled to room temperature and concentrated. 1N HCl (600 mL) and dichloromethane (800 mL) were added. This gave some solid precipitate which did not dissolve. Water (300 mL) was added to help identify layers. The lower organic layer containing solid and a bit of water was separated and this organic fraction was washed with 1M HCl/brine (400 mL of 1:1 mixture) before being dried (MgSO$_4$). A second drying (Na$_2$SO$_4$) was needed. After the drying agent was filtered off (washed through with 400 ml dichloromethane) the filtrate was concentrated (~60 g). This was azeotroped with toluene (400 mL) and final solvent removal gave subtitle compound (39.4 g).

$^1$H NMR δ (CDCl$_3$) 7.30 (d, 1H), 7.17 (s, 1H), 4.24 (d, 2H), 4.15–3.99 (m, 1H), 3.92 (s, 3H), 2.12 (s, 3H).

g) 3-(3,5-Dibromo-2-oxo-2H-pyrazin-1-yl)-5-fluoro-4-methyl-benzoic acid, methyl ester To a stirred solution of oxalyl bromide (49.9 mL) in dichloromethane (600 mL) at 0° C. under nitrogen was added 3-[(cyanomethyl)amino]-5-fluoro-4-methyl-benzoic acid methyl ester (Preparation 1f, 39.4 g) over 15 min. The mixture was allowed to warm to room temperature and stirred for 30 min then DMF (0.275 mL) was added and the mixture heated for 16 h at reflux. After cooling to 0° C., water (200 mL) was added over 15 min (caution) then the organic layer was separated, dried (MgSO$_4$) and evaporated. The residue was purified (SiO$_2$ chromatography eluting with dichloromethane) to afford the subtitle product (48.5 g).

$^1$H NMR δ (DMSO-d$_6$) 8.11 (s, 1H), 7.94 (s, 1H), 7.85 (dd, 1.5 Hz, 1H), 3.88 (s, 3H), 2.11 (d, 3H)

h) 1-(2-(Benzyloxy)phenyl)cyclopropanamine

Titanium(IV) isopropoxide (1.62 mL) was added to a stirred solution of 2-(benzyloxy)benzonitrile (1.05 g) in diethyl ether (25 mL) cooled to −78° C. under N$_2$ followed by the dropwise addition of ethylmagnesium bromide (3.67 mL of a 3M solution in diethylether). The resulting mixture was stirred at −78° C. for 10 min and then warmed to rt over 1 h. Boron trifluoride diethyl etherate (1.27 mL) was added dropwise and the mixture was stirred for 1 h. The reaction was quenched with 1M HCl (30 mL). Diethyl ether (30 mL) was added and the organic layer separated. To the aqueous layer was added aqueous 10% NaOH (50 mL) and diethyl ether and this was filtered through celite to remove solids (which were washed with further diethyl ether). This mixture was extracted with diethyl ether (2×70 mL) and dichloromethane (70 mL). All the organic layers were combined, dried (Na$_2$SO$_4$) and the solvents removed in vacuo. The residue was dissolved in dichloromethane and loaded on to an 10 g SCX cartridge. The impurities were washed through with methanol (50 mL) and discarded. Elution with 7N methanolic ammonia (25 mL) and evaporation in vacuo gave the subtitle compound as a brown oil (0.625 g).

$^1$H NMR δ (CDCl$_3$) 7.47 (d, 2H), 7.40 (t, 2H), 7.33 (t, 1H), 7.26-7.20 (m, 2H), 6.95 (d, 1H), 6.90 (td, 1H), 5.18 (s, 2H), 1.07 (dd, 2H), 0.89 (dd, 3H).

i) 3-[5-bromo-2-oxo-3-[[1-[2-(phenylmethoxy)phenyl]cyclopropyl]amino]-1(2H)-pyrazinyl]-5-fluoro-4-methyl-benzoic acid, methyl ester A solution of 1-(2-(benzyloxy)phenyl)cyclopropanamine (Preparation 1h, 5 g) in dioxane (200 mL) was treated with 3-(3,5-dibromo-2-oxo-2H-pyrazin-1-yl)-5-fluoro-4-methylbenzoic acid, methyl ester (Preparation 1g, 7.5 g) and N-ethyldiisopropylamine (5.36 mL) under nitrogen. The resulting solution was stirred at 100° C. for 8 h. The cooled reaction mixture was diluted with 2M HCl (300 mL), and extracted with ether (3×300 mL). The combined organics were dried (MgSO$_4$), filtered and evaporated to afford crude product. Purification (SiO$_2$ chromatography eluting with 20% ethyl acetate in iso-hexane) gave the subtitle compound. (9.20 g).

$^1$H NMR δ (DMSO-d$_6$) 7.82–7.76 (m, 2H), 7.59–7.49 (m, 3H), 7.41–7.26 (m, 3H), 7.24–7.15 (m, 1H), 7.06–6.98 (m, 2H), 6.89 (t, 1H), 5.22 (s, 1H), 3.85 (s, 2H), 3.31 (s, 3H), 2.03 (d, 3H), 1.25–1.07 (m, 4H).

j) 3-Fluoro-5-[3-[[1-(2-hydroxyphenyl)cyclopropyl]amino]-2-oxo-1(2H)-pyrazinyl]-4-methyl-benzoic acid, methyl ester To 3-[5-bromo-2-oxo-3-[[1-[2-(phenylmethoxy)phenyl]cyclopropyl]amino]-1(2H)-pyrazinyl]-5-fluoro-4-methyl-benzoic acid, methyl ester (Preparation 1i, 9.2 g) in ethanol (400 mL) was added ammonium formate (14.04 g) and 10% Pd/C (1.693 g). The reaction was heated at 75° C. for 1 h, filtered through celite washing the celite with further warm ethanol (100 mL) followed by dichloromethane (2000 mL) and the combined filtrates were evaporated, diluted with dichloromethane (1000 mL) and washed with water, dried (MgSO$_4$) and evaporated to give the subtitle compound (6.16 g).

$^1$H NMR δ (DMSO-d$_6$) 11.23 (s, 1H), 7.85–7.73 (m, 2H), 7.48–7.42 (m, 1H), 7.16-7.04 (m, 1H), 6.91–6.86 (m, 1H), 6.83–6.67 (m, 3H), 5.75 (s, 1H), 3.85 (s, 3H), 2.03 (s, 3H), 1.32–1.16 (m, 2H), 1.12–1.01 (m, 2H).

k) N-Cyclopropyl-3-fluoro-5-[3-[[1-(2-hydroxyphenyl)cyclopropyl]amino]-2-oxo-1(2H)-pyrazinyl]-4-methyl-benzamide Isopropylmagnesium chloride (30.1 ml of a 2M solution in THF) was added over 20 min to a solution of cyclopropylamine (10.61 mL) and 3-fluoro-5-[3-[[1-(2-hydroxyphenyl)cyclopropyl]amino]-2-oxo-1(2H)-pyrazinyl]-4-methyl-benzoic acid methyl ester (Preparation 1j, 6.16 g) in tetrahydrofuran (200 mL) and the reaction stirred at room temperature under nitrogen for 1 h. Water (100 mL) and 2M HCl (200 mL) were cautiously added and the aqueous layer extracted with dichloromethane (3×200 mL) and the combined organic extracts dried (MgSO$_4$) and the solvent removed to give the subtitle compound (5.00 g).

$^1$H NMR δ (DMSO-d$_6$) 11.14 (s, 1H), 8.52 (s, 1H), 8.46 (d, 1H), 7.74 (dd, 1H), 7.64 (s, 1H), 7.46 (dd, 1H), 7.13–7.08 (m, 1H), 6.91 (d, 1H), 6.82–6.72 (m, 3H), 2.88–2.78 (m, 1H), 1.99 (d, 3H), 1.30–1.20 (m, 2H), 0.88–0.79 (m, 2H), 0.70–0.63 (m, 2H), 0.55–0.50 (m, 2H).

l) 3-[3-[[1-[2-(2-chloroethoxy)phenyl]cyclopropyl]amino]-2-oxo-1(2H)-pyrazinyl]-N-cyclopropyl-5-fluoro-4-methyl-benzamide N-Cyclopropyl-3-fluoro-5-[3-[[1-(2-hydroxyphenyl)cyclopropyl]amino]-2-oxo-1(2H)-pyrazinyl]-4-methyl-benzamide (Preparation 1k, 5 g), 1-bromo-2-chloroethane (9.58 mL) and cesium carbonate (37.5 g) were stirred together in acetonitrile (200 mL) at 80° C. under nitrogen for 16 h. The cooled reaction mixture was evaporated to dryness, diluted with water (500 mL) and extracted with dichloromethane (3×300 mL). The combined organics were dried (MgSO$_4$), filtered and evaporated. The residue was triturated with 1:1 iso-hexane:diethyl ether to give the subtitle compound (4.60 g).

$^1$H NMR δ (DMSO-d$_6$) 8.45 (d, 1H), 7.72 (d, 1H), 7.60 (s, 1H), 7.51 (d, 1H), 7.27 (s, 1H), 7.24–7.16 (m, 1H), 7.00–6.84 (m, 2H), 6.75 (d, 1H), 4.30 (t, 2H), 4.00 (t, 2H), 2.93-2.77 (m, 1H), 1.95 (s, 3H), 1.31–1.02 (m, 4H), 0.75–0.62 (m, 2H), 0.58–0.47 (m, 2H).

m) N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide 3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Preparation 1l, 0.5 g) and 40% methylamine in water (0.697 mL) were heated at 100° C. in dioxane (8 mL) in a sealed tube for 24 h. Purification of the cooled solution by preparative HPLC (Waters Xbridge column—acetonitrile/0.2% ammonia mobile phase) gave the title compound (270 mg).

MS: APCI(+ve) 492 (M+H)$^+$.

$^1$H NMR δ (DMSO-d$_6$) 8.45 (1H, d), 7.73 (1H, d), 7.60 (1H, s), 7.52–7.47 (2H, m), 7.23–7.15 (1H, m), 6.95 (1H, d), 6.89–6.82 (2H, m), 6.73 (1H, d), 4.05 (2H, t), 2.89 (2H, t), 2.85–2.77 (1H, m), 2.35 (3H, s), 1.96 (3H, d), 1.25–0.97 (4H, m), 0.73–0.62 (2H, m), 0.57–0.48 (2H, m).

Preparation 1

Free Base Crystalline Form A

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide Crystalline Form A 3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Preparation 1l, 10 g) in dioxane (25 mL) was treated with methylamine (15 mL of a 40 wt % aqueous solution). The resulting mixture was stirred at 100° C. for 16 h in a sealed tube. The reaction mixture was cooled, filtered and the solvents removed in vacuo to give crude product (~10 g). The crude product (~8.0 g) was purified by RPHPLC (Waters X-Bridge column, 95-5% gradient of aqueous 0.2% ammonia in acetonitrile as mobile phase). The product containing fractions were combined, evaporated and triturated with diethyl ether overnight. The white solid was collected by filtration and dried in vacuo to afford the title compound (4.14 g).

NMR consistent with that described above in preparation 1.

MS: APCI(+ve) 492 (M+H)$^+$.

Elemental Analysis—Found (calculated): % C, 65.9 (66.0); % H, 6.1 (6.2); % N, 14.2 (14.3).

A sample of preparation 1 crystalline form A obtained by the procedure described above was analysed by XRPD, DSC and GVS. An XRPD diffraction pattern of preparation 1 crystalline form A is presented in FIG. 101. The melting temperature of preparation 1 crystalline form A as determined by DSC gave a single endothermic event, occurring at 163° C. (±2° C.), with a water uptake of 0.4% (±0.2%) between RH of 0%-80%, as measured by GVS.

Preparation 2

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide Dihydrochloride Salt Crystalline Form A To a solution of N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide (0.03 g) in MeOH (2 mL) was added a 4M solution of HCl in dioxane (0.5 ml). After being stirred overnight and evaporated to dryness, the residue was triturated in acetonitrile (2 ml) for 7 days. The solid was filtered off and dried in vacuo to afford the title compound (0.021 g).

MS: APCI(+ve) 492 (M+H)$^+$.

$^1$H NMR δ (DMSO-d$_6$) 8.99 (2H, s), 8.59 (1H, d), 7.85-7.72 (2H, m), 7.68 (1H, s), 7.33–7.22 (2H, m), 7.08–6.83 (4H, m), 4.32 (2H, t), 3.39 (3H, s), 2.91–2.77 (1H, m), 2.62 (2H, t), 2.06 (3H, s), 1.49–1.08 (4H, m), 0.74–0.64 (2H, m), 0.60–0.53 (2H, m) (Elemental Analysis—Chloride Ion: Found: Cl, 13.7%. Fits for 2.2±0.2 Cl equiv)

A sample of preparation 2 crystalline form A obtained by the procedure described above was analysed by XRPD. An XRPD diffraction pattern of preparation 2 crystalline form A is presented in FIG. 102

Preparation 3

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide L-Tartaric Acid Salt Crystalline Form A N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide (0.03 g) and L-tartaric acid (9 mg) were dissolved in MeOH (2 mL) at ambient temperature. After being stirred overnight and evaporated to dryness, the residue was triturated in acetonitrile (2 ml) for 7 days. The solid was filtered off and dried in vacuo to afford the title compound (0.021 g).

MS: APCI(+ve) 492 (M+H)$^+$.

$^1$H NMR δ (DMSO-d$_6$) 8.46 (1H, d), 7.80 (1H, s), 7.73 (1H, d), 7.62–7.55 (2H, m), 7.22 (1H, t), 7.00–6.86 (3H, m), 6.73 (1H, d), 4.21 (2H, t), 3.85 (2H, s), 3.29 (2H, t), 2.88–2.76 (1H, m), 2.61 (3H, s), 1.98 (3H, d), 1.30–1.11 (4H, m), 1.05–0.96 (1H, m), 0.73-0.62 (2H, m), 0.58–0.50 (2H, m).

Elemental Analysis—Found: % C, 57.7; H, 5.8; N, 11.0. $C_{27}H_{30}FN_5O_3 \cdot C_4H_6O_6$ requires: C, 58.0; H, 5.7; N, 10.9%

A sample of preparation 3 crystalline form A obtained by the procedure described above was analysed by XRPD. An XRPD diffraction pattern of preparation 3 crystalline form A is presented in FIG. 103.

Preparation 4

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide Alternative Synthesis 1 a)
Benzyl[2-(2-cyanophenoxy)ethyl]methylcarbamate

To a stirred suspension of sodium hydride (60% w/w, 8.23 g, 205.7 mmol) in dry THF (350 mL) under an inert atmosphere was added 2-fluorobenzonitrile (98% w/w, 20.34 g, 164.6 mmol) and the resulting mixture cooled to 2° C. (batch temperature). 2-(Methylamino)ethanol (16.04 mL, 197.5 mmol) was added at a rate commensurate with controlled hydrogen gas evolution. At the end of the addition, the mixture was allowed to warm to ambient temperature. After stirring overnight at ambient temperature, the reaction mixture was concentrated in vacuo to ~50 mL and partitioned between diethyl ether (200 mL) and water (200 mL). The aqueous phase was adjusted to pH 12 with aq. sodium hydroxide (1 M) and the phases separated. The aqueous fraction was re-extracted with diethyl ether (2×200 mL). Any interfacial gel was removed by filtration of the biphasic mixture through a short Celite pad before the phase separation. The organic fractions were combined, washed with brine (600 mL), dried over sodium sulfate and concentrated in vacuo to afford crude 2-[2-(methylamino)ethoxy]benzonitrile as an orange oil (32.26 g, ~164.6 mmol). This was dissolved in THF (195 mL) under an inert atmosphere and triethylamine (51.4 mL, 365 mmol) added. The stirred solution was chilled in an ice-water bath and benzyl chloroformate (37.0 mL, 238 mmol) added over 1 h. At the end of the addition, the reaction was allowed to warm slowly to ambient temperature where it was held overnight. Any residual benzyl chloroformate was then quenched through the addition of diethylamine (20 mL, 497 mmol). The resulting thick slurry was filtered through a short Celite pad, and the filtrate concentrated in vacuo. The residue was partitioned between aq. hydrochloric acid (0.2 M, 200 mL) and TBME (200 mL). The phases were separated and the organic phase washed with brine (100 mL), dried over sodium sulfate and concentrated in vacuo to ~120 mL. Isohexane was added by syringe pump until cloudiness was observed whereupon the mixture was left to stir at ambient temperature overnight, during which time crystallisation occurred. The slurry was filtered through 11 μm filter paper. The filter cake was washed with TBME/isohexane (1:1 v/v, 20 mL) and dried overnight (30° C., 400 mbar) to afford benzyl[2-(2-cyanophenoxy)ethyl]methylcarbamate (30.25 g) as a colourless solid. The mother liquors from the crystallisation and filtrate from the cake wash were combined, concentrated to dryness in vacuo and purified by Biotage chromatography on silica gel, eluting with an ethyl acetate/isohexane gradient, to afford further benzyl [2-(2-cyanophenoxy)ethyl]methylcarbamate (13.96 g) as a pale yellow solid. The material was combined to give benzyl [2-(2-cyanophenoxy)ethyl]methylcarbamate (44.21 g, 99.9% w/w).

Mp 52° C. (TBME/isohexane).

$^1$H NMR (400 MHz, DMSO-$d_6$, 90° C.) δ 7.67 (1H, dd, J=7.7, 1.6 Hz), 7.62 (1H, ddd, J=8.4, 7.7, 1.7 Hz), 7.37–7.27 (5H, m), 7.22 (1H, d, J=8.6 Hz), 7.09 (1H, ddd, J=7.6, 7.5, 0.5 Hz), 5.09 (2H, s), 4.30 (2H, t, J=5.6 Hz), 3.67 (2H, t, J=5.6 Hz), 3.03 (3H, s). LC-MS (ES+) m/z 311 (MH$^+$, 100%).

b) Benzyl[2-[2-(1-aminocyclopropyl)phenoxy]ethyl] methylcarbamate trifluoroacetic acid salt To a stirred solution of 2,2'-bipyridine (70 mg, 0.45 mmol) in dry 2-Me-THF (181 mL) at ambient temperature under an inert atmosphere was added drop-wise methyllithium (3.18 M in diethoxymethane, 0.62 mL, 1.97 mmol) until a lilac colour was observed. ClTi(O$^i$Pr)$_3$ (95% w/w, 91.4 mL, 363.6 mmol) was added to give a yellow solution. After cooling the reaction mixture to −60° C. (jacket temperature), methyllithium (3.18 M in diethoxymethane, 130.9 mL, 416.3 mmol) was added by syringe pump over 70 min. The mixture was allowed to warm to −20° C. during the addition and then to warm further to ambient temperature over 110 min to leave a solution of MeTi(O$^i$Pr)$_3$ (0.99 M in diethoxymethane/2-Me-THF, assayed against 1,5-cyclooctadiene).

A nitrogen-sparged solution of lithium iodide (80.78 g, 0.60 mol), dry isopropanol (45.5 mL, 0.60 mol) and 2,2'-bipyridine (0.83 g, 5.28 mmol) in dry 2-Me-THF (868 mL) was stirred at ambient temperature under an inert atmosphere. The mixture was briefly heated to 50° C. (batch temperature) to fully dissolve the lithium iodide. After cooling to −10° C. (jacket temperature), methyllithium (3.18 M in diethoxymethane, 180 mL, 572.4 mmol) was added by syringe pump over 15 min. After the addition was complete, the jacket temperature had increased to 10° C. The addition of further methyllithium (3.18 M in diethoxymethane, 11.6 mL, 36.9 mmol) in small aliquots was sufficient to induce a permanent colour change to lilac. The reaction mixture was then cooled to 0° C. (batch temperature) and a portion of the previously prepared solution of MeTi(O$^i$Pr)$_3$ (301 mL, 0.99 M in diethoxymethane/2-Me-THF, 297.5 mmol) was added over 25 min. At the end of the addition, the reaction solution was warmed to 20° C. (batch temperature) and benzyl[2-(2-cyanophenoxy)ethyl]methylcarbamate (Preparation 4a, 98.5% w/w, 75.04 g, 238.2 mmol) was charged. Neat diethylzinc (30.5 mL, 298 mmol) was then added by syringe pump over 85 min, during which time the reaction mixture was diluted with further 2-Me-THF (122 mL). After an overnight hold at ambient temperature, the mixture was cooled to 0° C. and discharged into a vigorously stirred ice-cold solution of citric acid (230.97 g, 1190 mmol) and trifluoroacetic acid (27.14 g, 238.0 mmol) in water (1000 mL). This produced a yellow organic fraction and an indigo aqueous fraction. The phases were separated and the organic phase warmed to 20° C. (batch temperature) and washed with aq. sodium hydroxide (2 M, 200 mL). The initial indigo aqueous fraction was re-extracted with 2-Me-THF (100 mL). The organic fractions were combined and concentrated in vacuo to ~750 mL. The residual solution was then extracted with aq. citric acid (0.1 M, 8×100 mL). Aq. sodium hydroxide (46/48% w/w, 50.76 g, 600 mmol) was added to the combined citric acid extracts at 6° C. (batch temperature) to afford a solution of pH 10. Further aq. sodium hydroxide (46/48% w/w, ~2 mL) was then added to basify the solution to pH>10. The basic aqueous phase was extracted with isopropyl acetate (2×200 mL, 1×100 mL); each organic extract was washed with brine (50 mL). The combined organic phase was filtered through a 0.45 μm membrane to leave a solution of benzyl [2-[2-(1-aminocyclopropyl)phenoxy]ethyl]methylcarbamate (12.74% w/w, 364.05 g, 136.2 mmol) which was concentrated in vacuo to leave benzyl [2-[2-(1-aminocyclopropyl)phenoxy]ethyl]methylcarbamate as an oil.

$^1$H NMR (400 MHz, DMSO-$d_6$, 90° C.) δ 7.35–7.27 (5H, m), 7.20 (1H, dd, J=7.5, 1.8 Hz), 7.15 (1H, ddd, J=8.0, 7.5, 1.8 Hz), 6.95 (1H, d, J=8.0 Hz), 6.85 (1H, ddd, J=8.5, 7.3, 1.0 Hz), 5.10 (2H, s), 4.19 (2H, t, J=5.6 Hz), 3.72 (2H, t, J=5.6 Hz), 3.03 (3H, s), 2.06 (2H, br s), 0.77–0.75 (2H, m), 0.72–0.68 (2H, m).

In order to form a salt, this oil was chilled in an ice-water bath and a solution of trifluororacetic acid (15.53 g, 136.2 mmol) in isopropyl acetate (210 mL) was added portion-wise. The solution was warmed to 63° C. (batch temperature) and seeded with benzyl [2-[2-(1-aminocyclopropyl)phenoxy] ethyl]methylcarbamate trifluoroacetic acid salt (24 mg). The mixture was cooled to 62° C. (batch temperature) to create a seed bed, before being ramp-cooled to 50° C. (batch temperature) at a rate of 1° C./h, and then to 0° C. (batch temperature) at a rate of 10° C./h. Further trifluoroacetic acid (3.11 g, 27.3 mmol) was added to ensure quantitative salt formation. After holding for 6 h at 0° C., the slurry was filtered through 11 μm filter paper. The filter cake was washed with isopropyl acetate (2×100 mL) and dried overnight (40° C., 400 mbar) to afford benzyl [2-[2-(1-aminocyclopropyl)phenoxy]ethyl]methylcarbamate trifluoroacetic acid salt (54.48 g, 98.9% w/w) as a colourless solid.

Mp 111-112° C. (isopropanol/heptane).

$^1$H NMR (400 MHz, DMSO-$d_6$, 90° C.) δ 8.04 (3H, br s), 7.39-7.29 (7H, m), 7.0 (1H, app d, J=8.0 Hz), 6.98 (1H, ddd, J=7.6, 7.4, 0.9 Hz), 5.11 (2H, s), 4.24 (2H, t, J=5.5 Hz), 3.75 (2H, t, J=5.5 Hz), 3.02 (3H, s), 1.26 (2H, dd, J=7.2, 5.9 Hz), 1.07 (2H, dd, J=7.2, 5.9 Hz).

LC-MS (ES+) m/z 341 (MH$^+$, [Free base], 100%).

c) Methyl 3-amino-5-fluoro-4-methylbenzoate sulfuric acid salt

To a solution of methyl 3-fluoro-5-iodo-4-methylbenzoate (115.5 g, 392.8 mmol) in toluene (~1600 mL) at ambient temperature was charged benzophenone imine (67.6 g, 373.0 mmol), 1,1'-bis(diphenylphosphino)ferrocene (9.80 g, 17.68 mmol) and cesium carbonate (179.2 g, 550.0 mmol). The reaction vessel was vacuum purged with nitrogen three times. Tris(dibenzylideneacetone)dipalladium(0) (5.34 g, 6.05 mmol) was added before the vessel was again vacuum purged with nitrogen three times. The reaction mixture was then stirred and heated to reflux for 4 d before being cooled to ambient temperature and filtered through GF/F filter paper under a nitrogen atmosphere. The filter cake was washed with toluene (230 mL) and the filtrates combined and washed with aq. sodium sulfite (5% w/w, 580 mL). The phases were separated and the aq. phase re-extracted with toluene (580 mL). The organic fractions were combined and washed with water (580 mL), dried over sodium sulfate and filtered through GF/F filter paper. The filter cake was washed with toluene (230 mL) and the combined filtrates concentrated to ~1000 mL in vacuo. After cooling the solution to ambient temperature, TBME (1040 mL) was charged followed by decolourising charcoal (60 g). The slurry was heated to 45-50° C. and then cooled to ambient temperature over 1 h and filtered through GF/F filter paper. The filter cake was washed with TBME/toluene (1:1 v/v, 2×230 mL). The filtrates were combined to afford a solution of methyl 3-[(diphenylmethylene)amino]-5-fluoro-4-methylbenzoate to which methanol (127 mL, 3135.4 mmol) was added. Sulfuric acid (21 mL, 394.0 mmol) was then charged over at least 1 h ensuring that the temperature was maintained in the range 18-23° C. The resulting slurry was filtered through 100 μm cloth. The filter cake was washed with TBME (580 mL) and dried on the filter under a flow of nitrogen for at least 2 h. The isolated solid was then slurried in acetonitrile (500 mL) at ambient temperature for 4-5 h before being filtered through 100 μm cloth. The filter cake was washed with acetonitrile (1×300 mL, 1×115 mL) and dried on the filter at up to 45° C. to afford methyl 3-amino-5-fluoro-4-methylbenzoate sulfuric acid salt (92.2 g, 94.5% w/w).

$^1$H NMR (400 MHz, DMSO-$d_6$) δ 7.21 (1H, s), 6.94 (1H, d, J=10.1 Hz), 5.83 (br s), 3.81 (3H, s), 2.04 (3H, d, J=1.5 Hz).

Methyl 3-amino-5-fluoro-4-methylbenzoate sulfuric acid salt was converted to methyl 3-(3,5-dibromo-2-oxo-1(2H)-pyrazinyl)-5-fluoro-4-methylbenzoate using similar procedures to those disclosed in preparations 1f and 1g.

d) Methyl 3-[3-[1-[2-[2-[(benzyloxycarbonyl)methylamino]ethoxy]phenyl]cyclopropylamino]-5-bromo-2-oxo-1(2H)-pyrazinyl]-5-fluoro-4-methylbenzoate A solution of benzyl [2-[2-(1-aminocyclopropyl)phenoxy]ethyl]methylcarbamate (Preparation 4b, 68.1% w/w, 102.2 mg, 204 μmol), methyl 3-(3,5-dibromo-2-oxo-1(2H)-pyrazinyl)-5-fluoro-4-methylbenzoate (Preparation 1g, 94.5 mg, 225 μmol) and N,N-diisopropylethylamine (137 μL, 818 μmol) in 1,4-dioxane (3 mL) was heated to 90° C. (jacket temperature) in a sealed reaction tube for 3 h, before being left to stir overnight at ambient temperature. Further methyl 3-(3,5-dibromo-2-oxo-1(2H)-pyrazinyl)-5-fluoro-4-methylbenzoate (8.6 mg, 20.4 μmol) was added and the reaction mixture re-heated to 90° C. (jacket temperature) for a further 90 min. The solution was then concentrated in vacuo before being purified by preparative TLC on silica, eluting with ethyl acetate/isohexane (1:2 v/v), to afford methyl 3-[3-[1-[2-[2-[(benzyloxycarbonyl)methylamino]ethoxy]phenyl]cyclopropylamino]-5-bromo-2-oxo-1(2H)-pyrazinyl]-5-fluoro-4-methylbenzoate (125.7 mg) as a white foam.

$^1$H NMR (400 MHz, DMSO-$d_6$) δ 7.78–7.65 (2H, m), 7.51–7.50 (1H, d, J=7.3 Hz), 7.29–7.26 (5H, m), 7.22–7.15 (1H, m), 7.01 (1H, s), 6.95–6.86 (2H, m), 5.07 (2H, s), 4.13–4.10 (2H, m), 3.83 (3H, s), 3.71 (2H, t, J=5.3 Hz), 2.99–2.97 (3H, m), 1.99 (3H, d, J=1.7 Hz), 1.12 (2H, m), 1.01–0.98 (2H, m).

LC-MS (ES+) m/z 679 (MH$^+$, 92%).

e) Benzyl[2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate A solution of cyclopropylamine (261.9 μL, 3.70 mmol) in dry THF (2 mL) under an inert atmosphere was chilled in an ice-water bath and freshly titrated isopropylmagnesium chloride (1.46 M in THF, 1.27 mL, 1.85 mmol) was added. A portion of this chloromagnesium cyclopropylamide solution (0.524 M in THF, 2.12 mL, 1.11 mmol) was added via syringe to a stirred solution of methyl 3-[3-[1-[2-[2-[(benzyloxycarbonyl)methylamino]ethoxy]phenyl]cyclopropylamino]-5-bromo-2-oxo-1(2H)-pyrazinyl]-5-fluoro-4-methylbenzoate (Preparation 4d, 125.7 mg, 185 μmol) in dry THF (2 mL) under an inert atmosphere. After 30 min, ethyl acetate (1 mL) was added before the reaction mixture was poured into ice-cold saturated aq. ammonium chloride (10 mL) and extracted with diethyl ether (3×10 mL). The organic extracts were combined, washed with brine (30 mL), dried over sodium sulfate and concentrated in vacuo. The residue was purified by preparative TLC on silica, eluting with ethyl acetate/isohexane/methanol (50:50:1 v/v), to afford benzyl [2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate (79.4 mg) as a white foam.

Alternatively, the subtitle compound may be accessed through a telescoped procedure from methyl 3-(3,5-dibromo-2-oxo-1(2H)-pyrazinyl)-5-fluoro-4-methylbenzoate (Preparation 1g) avoiding the need to isolate methyl 3-[3-[1-[2-[2-[(benzyloxycarbonyl)methylamino]ethoxy]phenyl]cyclopropylamino]-5-bromo-2-oxo-1(2H)-pyrazinyl]-5-fluoro-4-methylbenzoate (Preparation 4d), as follows: To a stirred solution of methyl 3-(3,5-dibromo-2-oxo-1(2H)-pyrazinyl)-5-fluoro-4-methylbenzoate (Preparation 1g, 18.7 g, 44.4 mmol) and benzyl [2-[2-(1-aminocyclopropyl)phenoxy]ethyl]methylcarbamate trifluoroacetic acid salt (Preparation 4b, 20.0 g, 44.0 mmol) in toluene (200 mL) under an inert atmosphere was added N,N-diisopropylethylamine (26.9 mL, 154.0 mmol). The reaction mixture was heated to 105° C. (jacket temperature) for 2 h and then cooled slowly to ambient temperature. The resulting orange slurry was quenched with water (200 mL) and the phases separated. The organic phase was washed with aq. sodium bisulfate solution (1 M, 3×200 mL) and brine (200 mL) and then concentrated in vacuo. The residue was purified by dry flash chromatography, gradient eluting with ethyl acetate/toluene. A portion of this solution containing methyl 3-[3-[1-[2-[2-[(benzyloxycarbonyl)methylamino]ethoxy]phenyl]cyclopropylamino]-5-bromo-2-oxo-1(2H)-pyrazinyl]-5-fluoro-4-methylbenzoate (2.0 g, 2.8 mmol) was dried by azeotropic distillation with toluene. The residual toluene solution (~18 mL) was cooled to 35° C. (jacket temperature) and cyclopropylamine (588 µL, 8.3 mmol) and sodium methoxide (30% w/w, 1.3 mL, 6.9 mmol) were added. The reaction mixture was stirred at 35° C. for 3 h and then quenched with aq. triethylamine (10% v/v, 5 mL). The phases were separated and the organic phase washed with aq. triethylamine (10% v/v, 2×5 mL). The solution was concentrated to dryness in vacuo to afford a yellow foam that was purified by Biotage chromatography, eluting with an ethyl acetate/isohexane gradient, and then crystallised from toluene/isohexane to afford benzyl [2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate (1.06 g, 93.5% w/w) as a colourless solid.

Mp 116-120° C. (toluene/isohexane).

$^1$H NMR (400 MHz, DMSO-$d_6$, 90° C.) δ 8.23 (1H, d, J=3.9 Hz), 7.72 (1H, dd, J=10.1, 1.6 Hz), 7.63 (1H, d, J=1.6 Hz), 7.56 (1H, dd, J=9.2, 1.6 Hz), 7.48 (1H, br s), 7.34–7.27 (5H, m), 7.20 (1H, ddd, J=8.2, 7.4, 1.7 Hz), 6.96–6.88 (3H, m), 5.11 (2H, s), 4.18 (2H, t, J=5.5 Hz), 3.75 (2H, t, J=5.5 Hz), 3.02 (3H, s), 2.86 (1H, ttd, J=7.4, 4.0, 3.9 Hz), 1.99 (3H, d, J=1.9 Hz), 1.21–1.06 (4H, m), 0.72–0.67 (2H, m), 0.60–0.56 (2H, m).

LC-MS (ES+) m/z 704 (MH$^+$, 92%).

f) N-Cyclopropyl-3-fluoro-4-methyl-5-[3-[1-[2-[2-(methylamino)ethoxy]phenyl]cyclopropylamino]-2-oxo-1(2H)-pyrazinyl]benzamide 10% Pd/C (87 L paste ex. Johnson Matthey, 110 mg) was washed with isopropanol (10 mL) and then suspended in further isopropanol (10 mL). A sample of this suspension (291 µL, ~3.2 mg Pd/C) was added to a solution of benzyl [2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate (Preparation 4e, 10.5 mg, 14.9 µmol) and ammonium formate (33.3 mg, 512 µmol) in isopropanol (0.1 mL). The reaction vessel was sealed and the suspension heated to 80° C. (jacket temperature) for 10 min. The reaction mixture was then filtered through Celite and the cake washed with ethyl acetate. The filtrates were combined and washed with brine that had been basified to pH 12 with KOH. The solution was filtered through a short pad of sodium sulfate and concentrated to dryness in vacuo to afford N-cyclopropyl-3-fluoro-4-methyl-5-[3-[1-[2-[2-(methylamino)ethoxy]phenyl]cyclopropylamino]-2-oxo-1(2H)-pyrazinyl]benzamide (6.0 mg) as a colourless solid.

$^1$H NMR (600 MHz, DMSO-$d_6$) δ 8.47 (1H, d, J=4.2 Hz), 7.73 (1H, d, J=10.3 Hz), 7.61 (1H, s), 7.52 (1H, s), 7.50 (1H, dd, J=7.5, 1.7 Hz), 7.19 (1H, td, J=7.8, 1.7 Hz), 6.96 (1H, d, J=8.1 Hz), 6.88 (1H, d, J=4.6 Hz), 6.86 (2H, t, J=7.4 Hz), 6.74 (1H, d, J=4.6 Hz), 4.09–4.02 (2H, m), 2.93–2.87 (2H, m), 2.87–2.81 (1H, m), 2.36 (3H, s), 1.99-1.94 (3H, m), 1.23–1.14 (3H, m), 1.06–1.00 (1H, m), 0.71–0.65 (2H, m), 0.58–0.49 (2H, m).

LC-MS (ES+) m/z 492 (MH$^+$, 100%).

Preparation 5

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide Alternative Synthesis 2 a)
Benzyl[2-(2-cyanophenoxy)ethyl]methylcarbamate

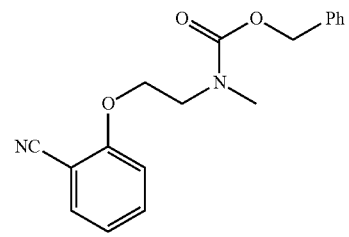 [SMILES: CN(CCOc1ccccc1C#N)C(=O)OCc1ccccc1]

To a stirred suspension of sodium hydride (60% w/w, 8.23 g, 205.7 mmol) in dry THF (350 mL) under an inert atmosphere was added 2-fluorobenzonitrile (20.34 g, 164.6 mmol) and the resulting mixture cooled to 2° C. (batch temperature). 2-(Methylamino)ethanol (16.04 mL, 197.5 mmol) was added at a rate commensurate with controlled hydrogen gas evolution. At the end of the addition, the mixture was allowed to warm to ambient temperature and held overnight. The reaction mixture was then concentrated in vacuo to ~50 mL and partitioned between diethyl ether (200 mL) and water (200 mL). The aqueous phase was adjusted to pH 12 with aq. sodium hydroxide (1 M) and the phases separated. The aqueous fraction was re-extracted with diethyl ether (2×200 mL). Any interfacial gel was removed by filtration of the biphasic mixture through a short Celite pad before the phase separation. The organic fractions were combined, washed with brine (600 mL), dried over sodium sulfate and concentrated in vacuo to afford crude 2-[2-(methylamino)ethoxy]benzonitrile as an orange oil. This was dissolved in THF (195 mL) under an inert atmosphere and triethylamine (51.4 mL, 365 mmol) added. The stirred solution was cooled to 0-5° C. and benzyl chloroformate (37.0 mL, 238 mmol) added over 1 h. At the end of the addition, the mixture was allowed to warm slowly to ambient temperature where it was held overnight. Any residual benzyl chloroformate was then quenched through the addition of diethylamine (20 mL, 497 mmol). The resulting thick slurry was filtered through a short Celite pad, and the filtrate concentrated in vacuo. The residue was partitioned between aq. hydrochloric acid (0.2 M, 200 mL) and TBME (200 mL). The phases were separated and the organic phase washed with brine (100 mL), dried over sodium sulfate and concentrated in vacuo to ~120 mL. Isohexane was added slowly until cloudiness was observed whereupon the mixture was left to stir at ambient temperature overnight. The resulting slurry was filtered through 11 µm filter paper. The filter cake was washed with TBME/isohexane (1:1 v/v, 20 mL) and dried overnight (30° C., 400 mbar) to afford benzyl [2-[2-cyanophenoxy)ethyl]methylcarbamate (30.25 g). The mother liquors from the crystallisation and filtrate from the cake wash were combined, concentrated to dryness in vacuo and purified by chromatography on silica gel, eluting with an ethyl acetate/isohexane gradient, to afford further benzyl [2-[2- cyanophenoxy)ethyl]methylcarbamate (13.96 g). The solids were combined to give benzyl [2-(2-cyanophenoxy)ethyl]methylcarbamate (44.21 g, 99.9% w/w). Mp 52° C. (TBME/isohexane).

$^1$H NMR (400 MHz, DMSO-$d_6$, 90° C.) δ 7.67 (1H, dd, J=7.7, 1.6 Hz), 7.62 (1H, ddd, J=8.4, 7.7, 1.7 Hz), 7.37–7.27 (5H, m), 7.22 (1H, d, J=8.6 Hz), 7.09 (1H, ddd, J=7.6, 7.5, 0.5 Hz), 5.09 (2H, s), 4.30 (2H, t, J=5.6 Hz), 3.67 (2H, t, J=5.6 Hz), 3.03 (3H, s).

LC-MS (ES+) m/z 311 (MH$^+$, 100%).

b) Benzyl[2-[2-(1-aminocyclopropyl)phenoxy]ethyl] methylcarbamate trifluoroacetic acid salt

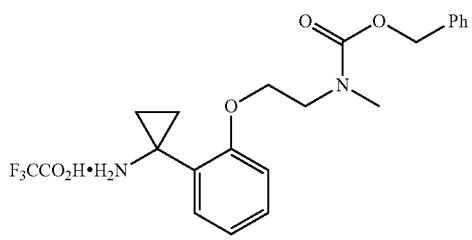

To a stirred solution of 2,2'-bipyridine (70 mg, 0.45 mmol) in dry 2-Me-THF (181 mL) at ambient temperature under an inert atmosphere was added drop-wise methyllithium (3.18 M in diethoxymethane, 0.62 mL, 1.97 mmol) until a lilac colour was observed. ClTi(O$^i$Pr)$_3$ (95% w/w, 91.4 mL, 363.6 mmol) was added to give a yellow solution. After cooling the reaction mixture to −60° C. (jacket temperature), methyllithium (3.18 M in diethoxymethane, 130.9 mL, 416.3 mmol) was added by syringe pump over 70 min. The mixture was allowed to warm to −20° C. during the addition and then to warm further to ambient temperature over 110 min to leave a solution of MeTi(O$^i$Pr)$_3$ (0.99 M in diethoxymethane/2-Me-THF, assayed against 1,5-cyclooctadiene).

A nitrogen-sparged solution of lithium iodide (80.78 g, 0.60 mol), dry isopropanol (45.5 mL, 0.60 mol) and 2,2'-bipyridine (0.83 g, 5.28 mmol) in dry 2-Me-THF (868 mL) was stirred at ambient temperature under an inert atmosphere. The mixture was briefly heated to 50° C. (batch temperature) to fully dissolve the lithium iodide. After cooling to −10° C. (jacket temperature), methyllithium (3.18 M in diethoxymethane, 180 mL, 572.4 mmol) was added by syringe pump over 15 min. After the addition was complete, the jacket temperature had increased to 10° C. The addition of further methyllithium (3.18 M in diethoxymethane, 11.6 mL, 36.9 mmol) in small aliquots was sufficient to induce a permanent colour change to lilac. The reaction mixture was then cooled to 0° C. (batch temperature) and a portion of the previously prepared solution of MeTi(O$^i$Pr)$_3$ (301 mL, 0.99 M in diethoxymethane/2-Me-THF, 297.5 mmol) was added over 25 min. At the end of the addition, the reaction solution was warmed to 20° C. (batch temperature) and benzyl[2-(2-cyanophenoxy)ethyl]methylcarbamate (75.04 g, 238.2 mmol) was charged. Neat diethylzinc (30.5 mL, 298 mmol) was then added by syringe pump over 85 min, during which time the reaction mixture was diluted with further 2-Me-THF (122 mL). After an overnight hold at ambient temperature, the mixture was cooled to 0° C. and discharged into a vigorously stirred ice-cold solution of citric acid (230.97 g, 1190 mmol) and trifluoroacetic acid (27.14 g, 238.0 mmol) in water (1000 mL). This produced a yellow organic fraction and an indigo aqueous fraction. The phases were separated and the organic phase warmed to 20° C. (batch temperature) and washed with aq. sodium hydroxide (2 M, 200 mL). The initial indigo aqueous fraction was re-extracted with 2-Me-THF (100 mL). The organic fractions were combined and concentrated in vacuo to ~750 mL. The residual solution was then extracted with aq. citric acid (0.1 M, 8×100 mL). Aq. sodium hydroxide (46/48% w/w, 50.76 g, 600 mmol) was added to the combined citric acid extracts at 6° C. (batch temperature) to afford a solution of pH 10. Further aq. sodium hydroxide (46/48% w/w, ~2 mL) was then added to basify the solution to pH>10. The basic aqueous phase was extracted with isopropyl acetate (2×200 mL, 1×100 mL); each organic extract was washed with brine (50 mL). The combined organic phase was filtered through a 0.45 μm membrane to leave a solution of benzyl [2-[2-(1-aminocyclopropyl)phenoxy]ethyl]methylcarbamate (12.74% w/w, 364.05 g, 136.2 mmol). After concentration in vacuo, the resulting oil was chilled in an ice-water bath and a solution of trifluororacetic acid (15.53 g, 136.2 mmol) in isopropyl acetate (210 mL) was added portion-wise. The solution was warmed to 63° C. (batch temperature) and seeded with benzyl [2-[2-(1-aminocyclopropyl)phenoxy]ethyl]methylcarbamate trifluoroacetic acid salt (24 mg). The mixture was cooled to 62° C. (batch temperature) to create a seed bed, before being ramp-cooled to 50° C. (batch temperature) at 1° C./h, and then to 0° C. (batch temperature) at 10° C./h. Further trifluoroacetic acid (3.11 g, 27.3 mmol) was added to ensure quantitative salt formation. After holding for 6 h at 0° C., the slurry was filtered through 11 μm filter paper. The filter cake was washed with isopropyl acetate (2×100 mL) and dried overnight (40° C., 400 mbar) to afford benzyl [2-[2-(1-aminocyclopropyl)phenoxy]ethyl]methylcarbamate trifluoroacetic acid salt (54.48 g, 98.9% w/w).

Mp 111-112° C. (isopropanol/heptane).

$^1$H NMR (400 MHz, DMSO-$d_6$, 90° C.) δ 8.04 (3H, br s), 7.39–7.29 (7H, m), 7.0 (1H, app d, J=8.0 Hz), 6.98 (1H, ddd, J=7.6, 7.4, 0.9 Hz), 5.11 (2H, s), 4.24 (2H, t, J=5.5 Hz), 3.75 (2H, t, J=5.5 Hz), 3.02 (3H, s), 1.26 (2H, dd, J=7.2, 5.9 Hz), 1.07 (2H, dd, J=7.2, 5.9 Hz).

LC-MS (ES+) m/z 341 (MH$^+$, 100%).

c) Methyl 3-amino-5-fluoro-4-methylbenzoate sulfuric acid salt

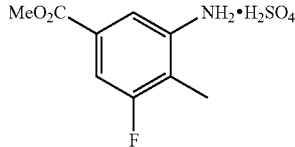

To a solution of methyl 3-fluoro-5-iodo-4-methylbenzoate (115.5 g, 392.8 mmol) in toluene (~1600 mL) at ambient temperature was charged benzophenone imine (67.6 g, 373.0 mmol), 1,1'-bis(diphenylphosphino)ferrocene (9.80 g, 17.68 mmol) and cesium carbonate (179.2 g, 550.0 mmol). The reaction vessel was vacuum purged with nitrogen three times. Tris(dibenzylideneacetone)dipalladium(0) (5.34 g, 6.05 mmol) was added before the vessel was again vacuum purged with nitrogen three times. The reaction mixture was then stirred and heated to reflux for 4 d before being cooled to ambient temperature and filtered through GF/F filter paper under a nitrogen atmosphere. The filter cake was washed with toluene (230 mL) and the filtrates combined and washed with aq. sodium sulfite (5% w/w, 580 mL). The phases were separated and the aq. phase re-extracted with toluene (580 mL).

The organic fractions were combined and washed with water (580 mL), dried over sodium sulfate and filtered through GF/F filter paper. The filter cake was washed with toluene (230 mL) and the combined filtrates concentrated to ~1000 mL in vacuo. After cooling the solution to ambient temperature, TBME (1040 mL) was charged followed by decolourising charcoal (60 g). The slurry was heated to 45-50° C. and then cooled to ambient temperature over 1 h and filtered through GF/F filter paper. The filter cake was washed with TBME/toluene (1:1 v/v, 2×230 mL). The filtrates were combined to afford a solution of methyl 3-[(diphenylmethylene) amino]-5-fluoro-4-methylbenzoate to which methanol (127 mL, 3135.4 mmol) was added. Sulfuric acid (21 mL, 394.0 mmol) was then charged over at least 1 h ensuring that the temperature was maintained in the range 18-23° C. The resulting slurry was filtered through 100 μm cloth. The filter cake was washed with TBME (580 mL) and dried on the filter under nitrogen for at least 2 h. The isolated solid was then slurried in acetonitrile (500 mL) at ambient temperature for 4-5 h before being filtered through 100 μm cloth. The filter cake was washed with acetonitrile (1×300 mL, 1×115 mL) and dried on the filter at up to 45° C. to afford methyl 3-amino-5-fluoro-4-methylbenzoate sulfuric acid salt (92.2 g, 94.5% w/w).

$^1$H NMR (400 MHz, DMSO-$d_6$) δ 7.21 (1H, s), 6.94 (1H, d, J=10.1 Hz), 5.83 (br s), 3.81 (3H, s), 2.04 (3H, d, J=1.5 Hz).

d) Methyl 3-(cyanomethylamino)-5-fluoro-4-methylbenzoate

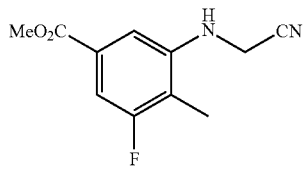 [SMILES: COC(=O)c1cc(F)c(C)c(NCC#N)c1]

To a solution of N,N-diisopropylethylamine (187 mL, 1073.6 mmol) in THF (240 mL) at 60-65° C. was added a solution of methyl 3-amino-5-fluoro-4-methylbenzoate sulfuric acid salt (80.0 g, 268.8 mmol) in THF (720 mL), maintaining the temperature in the range 45-65° C. Bromoacetonitrile (56.2 mL, 806.8 mmol) was charged and the solution heated to reflux for 3 d before concentration to 8 rel. vols. by distillation at atmospheric pressure. The solution was cooled to ambient temperature and water (1000 mL) added, maintaining the temperature in the range 18-23° C. The pH was adjusted to 1.2-1.5 with aq. hydrochloric acid (4 M, ~80 mL) and the resulting slurry stirred at ambient temperature for 2 h before being filtered through 100 μm filter cloth under nitrogen. The filter cake was washed with mixed heptanes (2×320 mL) and dried under nitrogen at up to 45° C. to afford methyl 3-(cyanomethylamino)-5-fluoro-4-methylbenzoate (54.9 g, 99.1% w/w).

$^1$H NMR (400 MHz, CDCl$_3$) δ 7.29 (1H, dd, T=1.1, 9.6 Hz), 7.16 (1H, s), 4.23 (2H, d, J=6.8 Hz), 4.15-4.03 (1H, m), 3.92 (3H, s), 2.11 (3H, d, T=1.7 Hz).

e) Methyl 3-[3,5-d]bromo-2-oxo-1(2H)-pyrazinyl]-5-fluoro-4-methylbenzoate

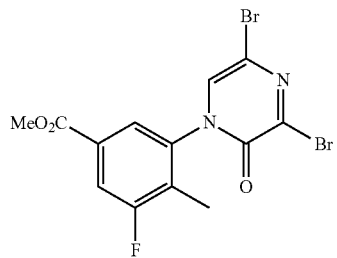 [SMILES: COC(=O)c1cc(F)c(C)c(-n2cc(Br)nc(Br)c2=O)c1]

To a solution of oxalyl bromide (25.5 mL, 266.3 mmol) in dichloromethane (350 mL) at 2° C. was charged portionwise methyl 3-(cyanomethylamino)-5-fluoro-4-methylbenzoate (20.0 g, 88.2 mmol). The solution was warmed to 25° C. over 30 min and then held for 60 min, before being heated to 32° C. over 15 min and being held overnight. The solution was cooled to 5° C. and water (100 mL) was charged over 30 min. Aq. sodium chloride (10% w/w, 100 mL) was then charged before the mixture was heated to 25° C. and held for 10 min. The phases were separated and to the lower organic phase was charged methanol (200 mL). The solution was concentrated by distillation under atmospheric pressure (325 mL distillate removed) and then cooled to 0° C. The mixture was held for 60 min before being filtered. The filter cake was washed with methanol (2×60 mL) and dried under vacuum at 40° C. to afford methyl 3-[3,5-d]bromo-2-oxo-1(2H)-pyrazinyl]-5-fluoro-4-methylbenzoate (22.5 g, 99.6% w/w).

$^1$H NMR (400 MHz, DMSO-$d_6$) δ 8.11 (1H, s), 7.94 (1H, s), 7.84 (1H, d, J=9.4 Hz), 3.89 (3H, s), 2.12 (3H, s).

LC-MS (ES+) m/z 679 (MH$^+$, 92%).

f) Benzyl[2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl] methylcarbamate

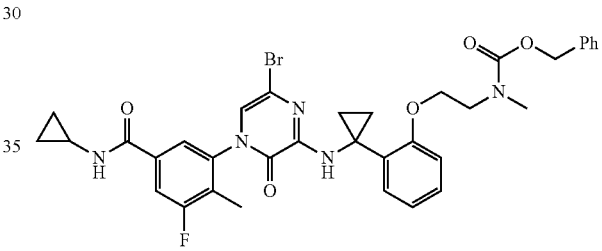

To a slurry of methyl 3-[3,5-d]bromo-2-oxo-1(2H)-pyrazinyl]-5-fluoro-4-methylbenzoate (7.58 g, 18.0 mmol) and benzyl [2-[2-(1-aminocyclopropyl)phenoxy]ethyl]methylcarbamate trifluoroacetic acid salt (8.11 g, 17.9 mmol) in toluene (76 mL) was added N,N-diisopropylethylamine (11 mL, 63.1 mmol). The mixture was heated to 95° C. and held for 2 h before being cooled back to 25° C. Water (76 mL) was charged and the mixture stirred for 10 min. The phases were separated and the upper organic phase washed with aq. sodium bisulfate (1 M, 3×76 mL) and aq. sodium chloride (10% w/w, 76 mL). The resulting solution was dried by azeotropic distillation with toluene (3×38 mL) to leave a toluene solution of methyl 3-[3-[1-[2-[2-[(benzyloxycarbonyl)methylamino]ethoxy]phenyl]cyclopropylamino]-5-bromo-2-oxo-1(2H)-pyrazinyl]-5-fluoro-4-methylbenzoate.

{$^1$H NMR (400 MHz, DMSO-$d_6$) δ 7.78–7.65 (2H, m), 7.51–7.50 (1H, d, J=7.3 Hz), 7.29–7.26 (5H, m), 7.22–7.15 (1H, m), 7.01 (1H, s), 6.95–6.86 (2H, m), 5.07 (2H, s), 4.13–4.10 (2H, m), 3.83 (3H, s), 3.71 (2H, t, J=5.3 Hz), 2.99–2.97 (3H, m), 1.99 (3H, d, J=1.7 Hz), 1.12 (2H, m), 1.01–0.98 (2H, m).

LC-MS (ES+) m/z 679 (MH$^+$, 92%).}

To this solution was charged methanolic sodium methoxide (30% w/w, 10.2 mL, 54.4 mmol) followed by cyclopropylamine (5.1 mL, 72.0 mmol). The mixture was held at 25° C. for 90 min before being washed with aq. sodium chloride (10% w/w containing 0.2% w/w triethylamine, 3×76 mL). The concentration of the solution was adjusted to 10 rel. vol. with respect to the starting methyl 3-(3,5-dibromo-2-oxo-1 (2H)-pyrazinyl)-5-fluoro-4-methylbenzoate by addition of further toluene (~19 mL). The solution was then heated to 100° C., and held for 30 min; cooled to 20° C. at 10° C./h, and held for 1 h; heated to 80° C. over 1 h, and held for 30 min; and finally cooled to 10° C. at 20° C./h before being held for 2 h. The resulting slurry was filtered. The filter cake was washed with toluene (2×30 mL) and dried under vacuum at 40° C. to afford benzyl [2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate (8.0 g, 89.0% w/w). Mp 116-120° C. (toluene/isohexane).

$^1$H NMR (400 MHz, DMSO-$d_6$, 90° C.) δ 8.23 (1H, d, J=3.9 Hz), 7.72 (1H, dd, J=10.1, 1.6 Hz), 7.63 (1H, d, J=1.6 Hz), 7.56 (1H, dd, J=9.2, 1.6 Hz), 7.48 (1H, br s), 7.34-7.27 (5H, m), 7.20 (1H, ddd, J=8.2, 7.4, 1.7 Hz), 6.96-6.88 (3H, m), 5.11 (2H, s), 4.18 (2H, t, J=5.5 Hz), 3.75 (2H, t, J=5.5 Hz), 3.02 (3H, s), 2.86 (1H, ttd, J=7.4, 4.0, 3.9 Hz), 1.99 (3H, d, J=1.9 Hz), 1.21-1.06 (4H, m), 0.72-0.67 (2H, m), 0.60-0.56 (2H, m).

LC-MS (ES+) m/z 704 (MH$^+$, 92%).

g) N-Cyclopropyl-3-fluoro-4-methyl-5-[3-[1-[2-[2-(methylamino)ethoxy]phenyl]cyclopropylamino]-2-oxo-1(2H)-pyrazinyl]benzamide

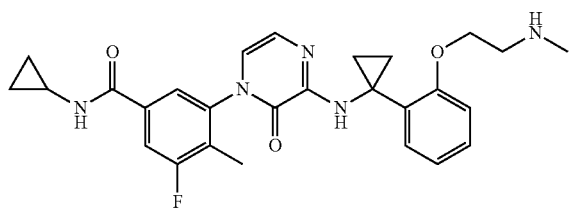 [SMILES: CNCCOc1ccccc1C1(Nc2nccn(-c3cc(C(=O)NC4CC4)cc(F)c3C)c2=O)CC1]

To a slurry of benzyl [2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate (15.0 g, 19.0 mmol), ammonium formate (4.9 g, 76.0 mmol) and 5% Pd/C (8.20 g, 3.8 mmol) in ethanol (150 mL) was charged water (6.8 mL, 379.8 mmol) and formic acid (1.49 mL, 388.0 mmol). The mixture was heated to 50° C. and held for 1 h before being cooled to 20° C. The mixture was filtered through a Celite pad, and the filter cake washed with ethanol (3×15 mL). The filtrates were combined and distilled (60° C. jacket temperature) to adjust the concentration of the solution to 2 rel. vol. with respect to the starting benzyl [2-[2-[1-[[6-bromo-4-[5-(cyclopropylcarbamoyl)-3-fluoro-2-methylphenyl]-3-oxo-3,4-dihydro-2-pyrazinyl]amino]cyclopropyl]phenoxy]ethyl]methylcarbamate. Isopropyl acetate (75 mL) was charged and the mixture cooled to 40° C. at 0.25° C./min. After seeding with the subtitle compound hydrobromide salt, the mixture was cooled further to 20° C. at 0.25° C./min. Isopropyl acetate (75 mL) was charged and the slurry cooled to 5° C. before being held for 1 h. The slurry was then filtered. The filter cake was washed with isopropyl acetate (15 mL) and dried under vacuum on the filter until de-liquoring was complete. The filter cake was then slurried in ethyl acetate (150 mL) and aq. sodium hydroxide (1 M, 150 mL) charged. The biphasic mixture was stirred at 20-25° C. until full dissolution was achieved (~30 min). The phases were separated and the upper organic phase washed with aq. sodium hydroxide (1 M, 150 mL). The solution was then heated to 50° C. and distilled under reduced pressure to double the concentration (75 mL distillate removed). The solution was heated to 70° C. and heptane (56 mL) charged slowly. After seeding with the subtitle compound, the mixture was cooled to 25° C. at 0.25° C./min. Further heptane (19 mL) was charged slowly and the slurry cooled to 5° C. before being held for 1 h. The slurry was then filtered. The filter cake was washed with heptane (15 mL) and dried under vacuum at 40° C. to afford N-cyclopropyl-3-fluoro-4-methyl-5-[3-[1-[2-[2-(methylamino)ethoxy]phenyl]cyclopropylamino]-2-oxo-1(2H)-pyrazinyl]benzamide (6.0 g, 96.0% w/w).

$^1$H NMR (600 MHz, DMSO-$d_6$) δ 8.47 (1H, d, J=4.2 Hz), 7.73 (1H, d, J=10.3 Hz), 7.61 (1H, s), 7.52 (1H, s), 7.50 (1H, dd, J=7.5, 1.7 Hz), 7.19 (1H, td, J=7.8, 1.7 Hz), 6.96 (1H, d, J=8.1 Hz), 6.88 (1H, d, J=4.6 Hz), 6.86 (2H, t, J=7.4 Hz), 6.74 (1H, d, J=4.6 Hz), 4.09-4.02 (2H, m), 2.93-2.87 (2H, m), 2.87-2.81 (1H, m), 2.36 (3H, s), 1.99-1.94 (3H, m), 1.23-1.14 (3H, m), 1.06-1.00 (1H, m), 0.71-0.65 (2H, m), 0.58-0.49 (2H, m).

LC-MS (ES+) m/z 492 (MH$^+$, 100%).

Example 1

Evaluation of Compound Activity on Intra-Alveolar Neutrophil Migration after Aerosol Challenge with Lipopolysacchamide (LPS) in Rats LPS challenge in rats causes an influx of inflammatory cells into the lungs. Rats are challenged either with an aerosol of 0.9% w/v saline or 0.1-0.5 mg/mL LPS in 0.9% saline for 30 min or an intratracheal dose of 0.1-10 µg/kg. This is repeated up to 8 times according to the experimental protocol. Rats are dosed with vehicle, standard compound or test compound by the appropriate route and frequency at various time points before and after challenge depending upon the experimental protocol. Test compound groups could either be the same compound at different doses or single doses of different compounds or a combination of the two. Test compounds are given by intraperitoneal, intravenous or subcutaneous injection or by inhalation or intratracheal administration.

The rats are euthanized at various time points after challenge depending upon the nature of the study, but typically 4 hr after LPS challenge with 1 mL pentobarbitone sodium. A tracheotomy is performed and a cannula inserted. The airway is then lavaged using 3 mL sterile PBS at room temperature. The PBS is left in the airway for 10 sec before being removed. The PBS containing cells is placed into a 15 mL centrifuge tube on ice. This process is repeated three times.

An aliquot of BAL fluid is removed and a differential cell count performed using a Sysmex cell counter (Sysmex UK, Milton Keynes). Cytospin slides are prepared by adding a 100 µL aliquot of BAL fluid into cytospin funnels in a Shandon Cytospin3 operated at 700 rpm for 5 min. Slides are stained on the Hema-Tek-2000 automatic slide stainer, using Wright-Giemsa stain and typically, 200 cells are counted under a microscope. Cells are classified as eosinophils, neutrophils and mononuclear cells (mononuclear cells included monocytes, macrophages and lymphocytes) and are expressed as a percentage of the total count.

Example 2

Evaluation of Lung Function in Anaesthetised Guinea-Pigs

Male Dunkin-Hartley guinea-pigs (300-600 g) are weighed and dosed with either vehicle or compound in an appropriate vehicle according to the experimental protocol via the intratracheal route under recoverable gaseous anaesthesia (5% halothane in oxygen). Following dosing, the animals are administered supplemental oxygen and monitored until full recovery. Typically a dose volume of 0.5 mL/kg is used for the intratracheal route. In a dose response study, animals are dosed with compound or vehicle two hours prior to the administration of bronchoconstrictor agent (e.g. histamine or methacholine). Test compound groups could either be the same compound at different doses or single doses of different compounds or a combination of the two.

The guinea-pigs are anaesthetised with pentobarbitone (1 mL/kg of 60 mg/mL solution intraperitoneally) approximately 30 min prior to the first bronchoconstrictor administration. The trachea is cannulated and the animal ventilated using a constant volume respiratory pump (Harvard Rodent Ventilator model 683) at a rate of 60 breaths/min and a tidal volume of 5 mL/kg. A jugular vein is cannulated for the administration of bronchoconstrictor agent or maintenance anaesthetic (0.1 mL of pentobarbitone solution, 60 mg/mL, as required).

The animals are then transferred to a Flexivent System (SCIREQ, Montreal, Canada) in order to measure airway resistance. The animals are ventilated (quasi-sinusoidal ventilation pattern) at 60 breaths/min at a tidal volume of 5 mL/kg. A positive end expiratory pressure of 2-3 cmH$_2$O is applied. Respiratory resistance is measured using the Flexivent "snapshot" facility (1 second duration, 1 Hz frequency). Once stable baseline resistance value has been obtained the animals are given histamine dihydrochloride or methacholine in ascending doses (histamine; 0.5, 1, 2, 3 and 5 µg/kg, i.v., methacholine; 3, 10 and 30 µg/kg, i.v.) at approximately 4-minute intervals via the jugular catheter. After each administration of histamine or methacholine, the peak resistance value is recorded. Guinea pigs are euthanised with approximately 1.0 mL pentobarbitone sodium (Euthatal) intravenously after the completion of the lung function measurements.

Percentage bronchoprotection produced by a compound is calculated at each dose of histamine or methacholine as follows:

$$\% \text{ bronchoprotection} = \frac{\% \text{ changeR}_{veh} - \% \text{ changeR}_{cmpd}}{\% \text{ changeR}_{veh}}$$

Where % change $R_{veh}$ is the mean of the maximum percentage change in airway resistance in the vehicle treated group.

Example 3

Evaluation of Compounds on Antigen Induced Eosinophilia in Ovalbumin Sensitised Brown Norway Rats On day 0 of the study Brown Norway rats are given a subcutaneous injection of 500 µg ovalbumin adsorbed onto 100 mg aluminium hydroxide in 0.4 mL saline in two distinct sites, approximately 0.2 mL per site. Day 14 and 15 following sensitisation the rats are challenged with aerosolised ovalbumin for 15 min. The rats are placed in groups of 10 in an acrylic box (internal dimensions 320 mm wide×320 mm deep×195 mm high, 20 L volume). A volume of 8 mL of 10 mg/mL ovalbumin in 0.9% saline, or 0.9% saline alone, is placed in each of two jet nebulizers (Sidestream®, Profile Respiratory Systems Ltd.). Compressed air at 6 L/min is passed through each nebulizer and the output of the nebulizers is passed into the box containing the rats.

Rats are dosed via the appropriate route with vehicle, standard compound or test compound at various time points before and after challenge depending upon the experimental protocol. Rats are euthanised with 0.5 mL pentobarbitone sodium (Euthatal) intraperitoneally at various times after challenge. A tracheotomy is performed and the trachea cannulated. The airway is then lavaged using 3 mL sterile PBS at room temperature. The PBS is left in the airway for 10 sec before being removed. The PBS containing cells is placed into a 15 mL centrifuge tube on ice. This process is repeated three times. The final volume recovered is recorded. An aliquot of BAL fluid is removed and counted using a Sysmex (Sysmex UK, Milton Keynes).

Cytospin slides are prepared by adding a 100 µL aliquot of BAL fluid into cytospin funnels in a Shandon Cytospin 3 operated at 700 rpm for 5 min. Slides are stained on the Hema-Tek-2000 automatic slide stainer, using Wright-Giemsa stain and typically, 200 cells are counted under a microscope. Cells are classified as eosinophils, neutrophils and mononuclear cells. Mononuclear cells included monocytes, macrophages and lymphocytes.

Example 4

Evaluation on the Effect of Compound on Lung Function and BAL-Neutrophilia Following Acute Smoke Exposure in the Mouse BALB/c or C57BL6/J mice undergo whole body exposure to main stream smoke (50 min/12 cigarettes) and fresh air once or twice a day for 1-9 days. Mice are dosed via the appropriate route with vehicle, standard compound or test compound at various time points before and after challenge depending upon the experimental protocol. On the final day of the experiment, mice are either killed with euthatal 0.2 mL i.p. and broncho-aveolar lavage fluid obtained for analysis of white blood cell infiltration (as described above) or lung function is assessed using a Flexivent System (SCIREQ, Montreal, Canada). Alternatively lung mechanics are measured using a forced manoeuvres system (EMMS).

Mice are anaesthetised with pentobarbitone (1/10 dilution at a dose volume of 1 mL/kg intraperitoneally). The trachea is cannulated and the animal transferred to the Flexivent System where they are ventilated (quasi-sinusoidal ventilation pattern) at a rate of 150 breath/min and a tidal volume of 10 mL/kg in order to measure airways resistance. Respiratory resistance is measured using the Flexivent "snapshot" facility (1 second duration, 1 Hz frequency). Mice are euthanised with approximately 0.5 mL pentobarbitone sodium (Euthatal) intravenously after the completion of the lung function measurements.

Example 5

Inhibition of Lipopolysacchamide (LPS)-Induced TNFα Production in Human Peripheral Blood Mononuclear Cells Human isolated peripheral blood mononuclear cells (PBMCs) were pre-incubated with a range of concentrations of the p38 inhibitor compound N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide (Compound A), alone or in the presence of a range of concentrations of a second compound with a distinct pharmacological activity for 18 hr at 37° C. After the pre-incubation period, the cells were then incubated with LPS (1 μg/mL) for 4 hr at 37° C. to induce TNFα production. The total assay volume was 200 μL. At the end of the incubation period, 25 μL of the culture supernatant was analysed to quantify the TNFα released using a Flourescence-linked immunosorbance assay (FLISA). Fluorescence levels were read on an FMAT plate reader. Inhibition curves were fitted using a 4-parameter logistic equation in a non-linear curve fitting routine and activity was expressed as $pIC_{50}$. In this series of experiments, the test of Compound A alone gave a $pIC_{50}$ for inhibition of LPS-induced TNFα production from human PBMC of 8.1±0.32, n=17

In the particular series of experiments described below, compound A was tested in combination with each of the Compounds B to R described in Table 1. In Table 1 the chemical structure of each of the exemplified compounds is depicted together with the chemical name used in the present specification to denote the compound parent structure.

TABLE 1

| Compound | Name/Parent Structure | Other name or description |
|---|---|---|
| A | N-cyclopropyl-3-fluoro-4-methyl-5-[3-[[1-[2-[2-(methylamino)ethoxy]phenyl]cyclopropyl]amino]-2-oxo-pyrazin-1-yl]benzamide 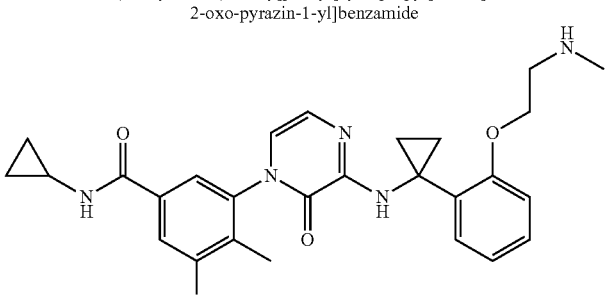 | An inhibitor of p38 kinase |
| B | [2-((R)-cyclohexyl-hydroxy-phenyl-methyl)-oxazol-5-ylmethyl]-dimethyl-(3-phenoxy-propyl)-ammonium bromide (WO2007/017669) 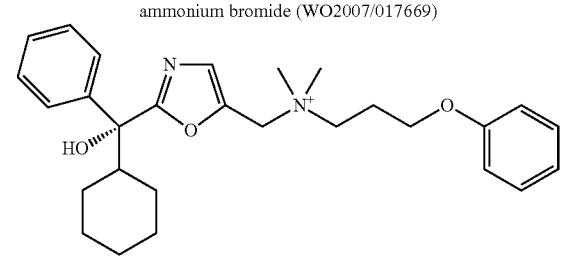 | A muscarinic receptor antagonist |

TABLE 1-continued

Compounds

| Compound | Name/Parent Structure | Other name or description |
|---|---|---|
| C | N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (WO2008/096111)<br />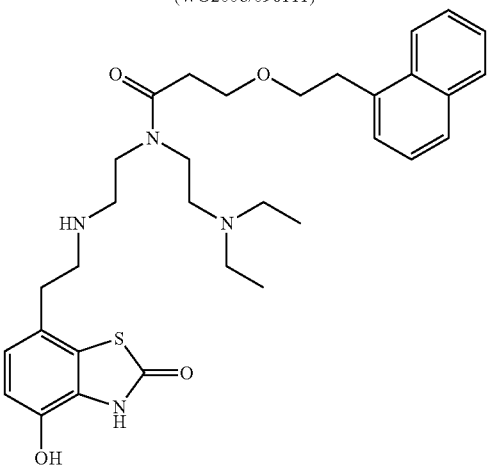 | A β2-adreno-ceptor agonist |
| D | [(3R)-1-(3-phenoxypropyl)quinuclidin-1-ium-3-yl]2-hydroxy-2,2-bis(2-thienyl)acetate bromide (IUPAC name (Lexichem))<br />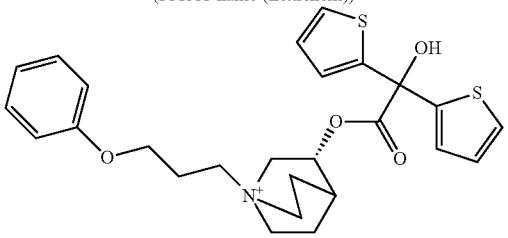 | Aclidinium bromide A muscarinic receptor antagonist |
| E | 5-[(1R)-2-[(5,6-diethylindan-2-yl)amino]-1-hydroxy-ethyl]-8-hydroxy-1H-quinolin-2-one maleate (IUPAC name (Lexichem))<br />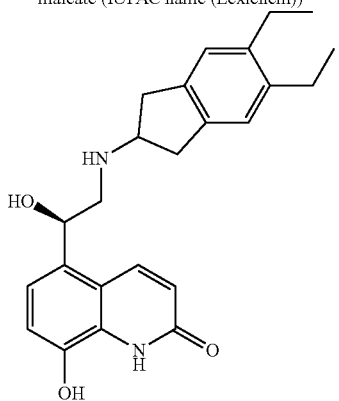 | Indacaterol A β2-adreno-ceptor agonist |

TABLE 1-continued

Compounds

| Compound | Name/Parent Structure | Other name or description |
|---|---|---|
| F | 7-[(1R)-2-({2-[(3-{[2-(2-chlorophenyl)ethyl]amino}propyl)thio]ethyl}amino)-1-hydroxyethyl]-4-hydroxy-1,3-benzothiazol-2(3H)-one dihydrobromide (WO2007/027134) | A β2-adrenoceptor agonist |
| G | 4-hydroxy-7-[(1R)-1-hydroxy-2-[2-[3-[[(2-methoxyphenyl)methylamino]methyl]phenyl]ethylamino]ethyl]-3H-1,3-benzothiazol-2-one (IUPAC name (Lexichem)) | A β2-adrenoceptor agonist |
| H | N-Cyclohexyl-N³-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide di-D-mandelate (WO2008/075026) | A β2-adrenoceptor agonist |
| I | [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-bissulfonate (WO2008/096149) | A muscarinic receptor antagonist |

TABLE 1-continued

Compounds

| Compound | Name/Parent Structure | Other name or description |
|---|---|---|
| J | (R)-1-[2-(4-fluoro-phenyl)-ethyl]-3-((S)-2-phenyl-2-piperidin-1-yl-propionyloxy)-1-azonia-bicyclo[2.2.2]octane 4-methylbenzenesulfonate (WO2008/75005) | A muscarinic receptor antagonist |
| K | ((R)-3-(1-phenyl-cycloheptanecarbonyloxy)-1-(pyridin-2-ylcarbamoylmethyl)-1-azonia-bicyclo[2.2.2]octane bromide (WO2009/139708) | A muscarinic receptor antagonist |
| L | [(3R)-1,1-dimethylpyrrolidin-1-ium-3-yl](2R)-2-cyclopentyl-2-hydroxy-2-phenyl-acetate iodide (IUPAC name (Lexichem)) | Glycopyrrolate A muscarinic receptor antagonist |
| M | (1R,2R,4S,5S,7S)-7-{[hydroxy(dithiophen-2-yl)acetyl]oxy}-9,9-dimethy-3-oxa-9-azoniatricyclo[3.3.1.0~2,4~]nonane bromide (IUPAC name (ACD)) | Tiotropium A muscarinic receptor antagonist |

TABLE 1-continued

Compounds

| Compound | Name/Parent Structure | Other name or description |
|---|---|---|
| N | [1-[3-[2-chloro-4-[[[(2R)-2-hydroxy-2-(8-hydroxy-2-oxo-1H-quinolin-5-yl)ethyl]amino]methyl]-5-methoxy-anilino]-3-oxo-propyl]-4-piperidyl]N-(2-phenylphenyl)carbamate (IUPAC name (Lexichem)) 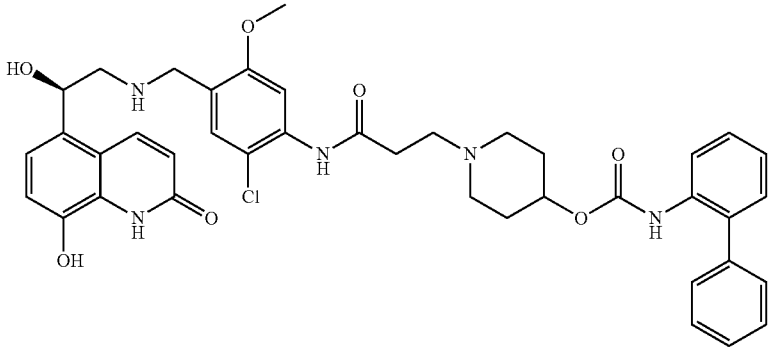 [SMILES: COc1cc(NC(=O)CCN2CCC(OC(=O)Nc3ccccc3-c3ccccc3)CC2)c(Cl)cc1CNC[C@H](O)c1ccc(O)c2[nH]c(=O)ccc12] | GSK961081 A combined muscarinic receptor antagonist β2-adreno-ceptor agonist (MABA) |
| O | 5-[2-[(3S)-pyrrolidin-3-yl]oxyphenyl]-2-ureido-thiophene-3-carboxamide (IUPAC name (Lexichem)) 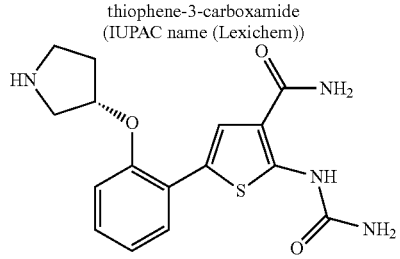 | An inhibitor of I kappaB kinase 2 |
| P | 2,2,2-Trifluoro-N-[(1R,2S)-1-[1-(4-fluorophenyl)indazol-5-yl]oxy-1-(3-methoxyphenyl)propan-2-yl]acetamide (WO2008/076048) 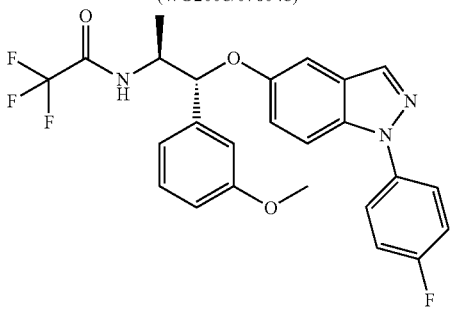 | A selective glucocorticoid receptor agonist |

TABLE 1-continued

Compounds

| Compound | Name/Parent Structure | Other name or description |
|---|---|---|
| Q | 6-Fluoro-N-((1s,4s)-4-(6-fluoro-2,4-dioxo-1-(4'-(piperazin-1-ylmethyl)-biphenyl-3-yl)-1,2-dihydropyrido[2,3-d]pyrimidin-3(4H)-yl)cyclohexyl)imidazo[1,2-a]pyridine-2-carboxamide (PCT/GB2008/000061) | An inhibitor of type 4 cAMP phosphodiesterase (PDE4) |
| R | 6-[2-(4-Cyano-phenyl)-2H-pyrazol-3-yl]-5-methyl-3-oxo-4-(3-trifluoromethyl-phenyl)-3,4-dihydro-pyrazine-2-carboxylic acid ethylamide (WO2007/129963) | An inhibitor of neutrophil elastase |

The pIC$_{50}$ and maximal inhibition achieved for combinations of Compound A with the muscarinic receptor antagonists Compound B (FIG. 1), Compound D (FIG. 3), Compound I (FIG. 8), Compound J (FIG. 9), Compound K (FIG. 10), Compound L (FIG. 11) and Compound M (FIG. 12) are shown in Tables 2, 4, 9, 10, 11, 12 and 13 respectively.

The pIC$_{50}$ and maximal inhibition achieved for combinations of Compound A with the β$_2$-adrenoceptor agonists Compound C (FIG. 2), Compound E (FIG. 4), Compound F (FIG. 5), Compound G (FIG. 6) and Compound H (FIG. 7) are shown in Tables 3, 5, 6, 7 and 8 respectively.

The pIC$_{50}$ and maximal inhibition achieved for combinations of Compound A with the combined muscarinic receptor antagonist β2-adrenoceptor agonist Compound N (FIG. 13) is shown in Table 14.

The pIC$_{50}$ and maximal inhibition achieved for combinations of Compound A with the IkappaB kinase-2 inhibitor Compound O (FIG. 14) is shown in Table 15.

The pIC$_{50}$ and maximal inhibition achieved for combinations of Compound A with the selective glucocorticoid receptor agonist Compound P (FIG. 15) is shown in Table 16.

The pIC$_{50}$ and maximal inhibition achieved for combinations of Compound A with the type 4 phosphodiesterase inhibitor Compound Q (FIG. 16) is shown in Table 17.

The pIC$_{50}$ and maximal inhibition achieved for combinations of Compound A with the neutrophil elastase inhibitor Compound R (FIG. 17) is shown in Table 18.

TABLE 2

Effect of the combination of Compound A and Compound B on LPS stimulated TNFα production from human PBMC

| Compound | Concentration (M) | pIC$_{50}$ Compound A | % Inhibition @ 1000 nM |
|---|---|---|---|
| Compound B | 0 | 7.7 | 88 |
| Compound B | $1 \times 10^{-10}$ | 7.4 | 86 |
| Compound B | $1 \times 10^{-9}$ | 7.1 | 89 |
| Compound B | $1 \times 10^{-8}$ | 7.3 | 88 |
| Compound B | $1 \times 10^{-7}$ | 7.4 | 89 |
| Compound B | $1 \times 10^{-6}$ | 7.7 | 90 |

TABLE 3

Effect of the combination of Compound A and Compound C on LPS stimulated TNFα production from human PBMC

| Compound | Concentration (M) | pIC$_{50}$ Compound A | % Inhibition @ 1000 nM |
|---|---|---|---|
| Compound C | 0 | 7.7 | 88 |
| Compound C | $1 \times 10^{-10}$ | 7.4 | 82 |
| Compound C | $1 \times 10^{-9}$ | 7.1 | 85 |
| Compound C | $1 \times 10^{-8}$ | 7.8 | 88 |
| Compound C | $1 \times 10^{-7}$ | 7.6 | 91 |
| Compound C | $1 \times 10^{-6}$ | 7.8 | 91 |

TABLE 4

Effect of the combination of Compound A and Compound D on LPS stimulated TNFα production from human PBMC

| Compound | Concentration (M) | pIC$_{50}$ Compound A | % Inhibition @ 1000 nM |
|---|---|---|---|
| Compound D | 0 | 7.7 | 88 |
| Compound D | $1 \times 10^{-10}$ | 7.7 | 89 |
| Compound D | $1 \times 10^{-9}$ | 7.6 | 85 |
| Compound D | $1 \times 10^{-8}$ | 8.2 | 85 |
| Compound D | $1 \times 10^{-7}$ | 7.8 | 87 |
| Compound D | $1 \times 10^{-6}$ | 8.0 | 87 |

TABLE 5

Effect of the combination of Compound A and Compound E on LPS stimulated TNFα production from human PBMC

| Compound | Concentration (M) | pIC$_{50}$ Compound A | % Inhibition @ 1000 nM |
|---|---|---|---|
| Compound E | 0 | 7.7 | 88 |
| Compound E | $1 \times 10^{-10}$ | 7.8 | 89 |
| Compound E | $1 \times 10^{-9}$ | 7.9 | 92 |
| Compound E | $1 \times 10^{-8}$ | 8.2 | 92 |
| Compound E | $1 \times 10^{-7}$ | 8.2 | 92 |
| Compound E | $1 \times 10^{-6}$ | 8.3 | 94 |

TABLE 6

Effect of the combination of Compound A and Compound F on LPS stimulated TNFα production from human PBMC

| Compound | Concentration (M) | pIC$_{50}$ Compound A | % Inhibition @ 1000 nM |
|---|---|---|---|
| Compound F | 0 | 8.5 | 93 |
| Compound F | $1 \times 10^{-10}$ | 8.4 | 91 |
| Compound F | $1 \times 10^{-9}$ | 9.0 | 97 |
| Compound F | $1 \times 10^{-8}$ | 9.0 | 98 |
| Compound F | $1 \times 10^{-7}$ | 9.2 | 100 |
| Compound F | $1 \times 10^{-6}$ | 8.7 | 98 |

TABLE 7

Effect of the combination of Compound A and Compound G on LPS stimulated TNFα production from human PBMC

| Compound | Concentration (M) | pIC$_{50}$ Compound A | % Inhibition @ 1000 nM |
|---|---|---|---|
| Compound G | 0 | 8.5 | 93 |
| Compound G | $1 \times 10^{-10}$ | 8.3 | 94 |
| Compound G | $1 \times 10^{-9}$ | 8.8 | 92 |
| Compound G | $1 \times 10^{-8}$ | 9.0 | 95 |
| Compound G | $1 \times 10^{-7}$ | 9.0 | 97 |
| Compound G | $1 \times 10^{-6}$ | 9.0 | 98 |

TABLE 8

Effect of the combination of Compound A and Compound H on LPS stimulated TNFα production from human PBMC

| Compound | Concentration (M) | pIC$_{50}$ Compound A | % Inhibition @ 1000 nM |
|---|---|---|---|
| Compound H | 0 | 8.0 | 99 |
| Compound H | $1 \times 10^{-10}$ | 8.0 | 99 |
| Compound H | $1 \times 10^{-9}$ | 8.1 | 103 |
| Compound H | $1 \times 10^{-8}$ | 8.4 | 100 |
| Compound H | $1 \times 10^{-7}$ | 8.7 | 101 |
| Compound H | $1 \times 10^{-6}$ | 8.4 | 101 |

TABLE 9

Effect of the combination of Compound A and Compound I on LPS stimulated TNFα production from human PBMC

| Compound | Concentration (M) | pIC$_{50}$ Compound A | % Inhibition @ 1000 nM |
|---|---|---|---|
| Compound I | 0 | 8.0 | 96 |
| Compound I | $1 \times 10^{-10}$ | 7.8 | 96 |
| Compound I | $1 \times 10^{-9}$ | 8.1 | 99 |
| Compound I | $1 \times 10^{-8}$ | 8.0 | 100 |
| Compound I | $1 \times 10^{-7}$ | 8.3 | 104 |
| Compound I | $1 \times 10^{-6}$ | 8.5 | 103 |

TABLE 10

Effect of the combination of Compound A and Compound J on LPS stimulated TNFα production from human PBMC

| Compound | Concentration (M) | pIC$_{50}$ Compound A | % Inhibition @ 1000 nM |
|---|---|---|---|
| Compound J | 0 | 7.9 | 92 |
| Compound J | $1 \times 10^{-10}$ | 7.7 | 97 |
| Compound J | $1 \times 10^{-9}$ | 7.8 | 102 |
| Compound J | $1 \times 10^{-8}$ | 8.0 | 94 |
| Compound J | $1 \times 10^{-7}$ | 8.1 | 99 |
| Compound J | $1 \times 10^{-6}$ | 7.9 | 97 |

TABLE 11

Effect of the combination of Compound A and Compound K on LPS stimulated TNFα production from human PBMC

| Compound | Concentration (M) | pIC$_{50}$ Compound A | % Inhibition @ 1000 nM |
|---|---|---|---|
| Compound K | 0 | 7.8 | 93 |
| Compound K | $1 \times 10^{-10}$ | 7.7 | 95 |
| Compound K | $1 \times 10^{-9}$ | 7.4 | 99 |
| Compound K | $1 \times 10^{-8}$ | 7.9 | 95 |
| Compound K | $1 \times 10^{-7}$ | 8.1 | 103 |
| Compound K | $1 \times 10^{-6}$ | 8.0 | 101 |

TABLE 12

Effect of the combination of Compound A and Compound L on LPS stimulated TNFα production from human PBMC

| Compound | Concentration (M) | pIC$_{50}$ Compound A | % Inhibition @ 1000 nM |
|---|---|---|---|
| Compound L | 0 | 7.9 | 94 |
| Compound L | $1 \times 10^{-10}$ | 7.9 | 98 |
| Compound L | $1 \times 10^{-9}$ | 7.8 | 100 |
| Compound L | $1 \times 10^{-8}$ | 7.9 | 91 |
| Compound L | $1 \times 10^{-7}$ | 7.9 | 99 |
| Compound L | $1 \times 10^{-6}$ | 7.8 | 95 |

TABLE 13

Effect of the combination of Compound A and Compound M on LPS stimulated TNFα production from human PBMC

| Compound | Concentration (M) | pIC$_{50}$ Compound A | % Inhibition @ 1000 nM |
|---|---|---|---|
| Compound M | 0 | 7.9 | 94 |
| Compound M | $1 \times 10^{-10}$ | 7.8 | 95 |
| Compound M | $1 \times 10^{-9}$ | 8.2 | 91 |
| Compound M | $1 \times 10^{-8}$ | 8.0 | 97 |
| Compound M | $1 \times 10^{-7}$ | 8.2 | 95 |
| Compound M | $1 \times 10^{-6}$ | 7.9 | 96 |

TABLE 14

Effect of the combination of Compound A and Compound N on LPS stimulated TNFα production from human PBMC

| Compound | Concentration (M) | pIC$_{50}$ Compound A | % Inhibition @ 1000 nM |
|---|---|---|---|
| Compound N | 0 | 8.6 | 96 |
| Compound N | $1 \times 10^{-10}$ | 8.5 | 100 |
| Compound N | $1 \times 10^{-9}$ | 8.7 | 100 |
| Compound N | $1 \times 10^{-8}$ | 8.8 | 101 |
| Compound N | $1 \times 10^{-7}$ | 8.8 | 102 |
| Compound N | $1 \times 10^{-6}$ | 8.4 | 102 |

TABLE 15

Effect of the combination of Compound A and Compound O on LPS stimulated TNFα production from human PBMC

| Compound | Concentration (M) | pIC$_{50}$ Compound A | % Inhibition @ 1000 nM |
|---|---|---|---|
| Compound O | 0 | 8.4 | 97 |
| Compound O | $1 \times 10^{-10}$ | 8.1 | 103 |
| Compound O | $1 \times 10^{-9}$ | 8.4 | 99 |
| Compound O | $1 \times 10^{-8}$ | 8.2 | 100 |
| Compound O | $1 \times 10^{-7}$ | 8.0 | 104 |
| Compound O | $1 \times 10^{-6}$ | — | 105 |

TABLE 16

Effect of the combination of Compound A and Compound P on LPS stimulated TNFα production from human PBMC

| Compound | Concentration (M) | pIC$_{50}$ Compound A | % Inhibition @ 1000 nM |
|---|---|---|---|
| Compound P | 0 | 8.3 | 97 |
| Compound P | $1 \times 10^{-10}$ | 8.6 | 102 |
| Compound P | $1 \times 10^{-9}$ | 9.0 | 103 |
| Compound P | $1 \times 10^{-8}$ | 8.8 | 103 |
| Compound P | $1 \times 10^{-7}$ | 9.0 | 102 |
| Compound P | $1 \times 10^{-6}$ | 8.7 | 100 |

TABLE 17

Effect of the combination of Compound A and Compound Q on LPS stimulated TNFα production from human PBMC

| Compound | Concentration (M) | pIC$_{50}$ Compound A | % Inhibition @ 1000 nM |
|---|---|---|---|
| Compound Q | 0 | 8.3 | 97 |
| Compound Q | $1 \times 10^{-10}$ | 8.0 | 99 |
| Compound Q | $1 \times 10^{-9}$ | 8.6 | 101 |
| Compound Q | $1 \times 10^{-8}$ | 8.4 | 101 |
| Compound Q | $1 \times 10^{-7}$ | 8.6 | 102 |
| Compound Q | $1 \times 10^{-6}$ | 8.5 | 103 |

TABLE 18

Effect of the combination of Compound A and Compound R on LPS stimulated TNFα production from human PBMC

| Compound | Concentration (M) | pIC$_{50}$ Compound A | % Inhibition @ 1000 nM |
|---|---|---|---|
| Compound R | 0 | 8.3 | 97 |
| Compound R | $1 \times 10^{-10}$ | 7.9 | 98 |
| Compound R | $1 \times 10^{-9}$ | 8.1 | 100 |
| Compound R | $1 \times 10^{-8}$ | 8.0 | 98 |
| Compound R | $1 \times 10^{-7}$ | 7.8 | 101 |
| Compound R | $1 \times 10^{-6}$ | 7.4 | 101 |

Example 6

Evaluation of Bronchodilator Activity in the Guinea-Pig Isolated Tracheal Ring Preparation Guinea-pigs (300-600 g) were killed by cervical dislocation and the trachea removed. After clearing the adherent connective tissue, the trachea was cut into segments (2-3 cartilage rings in width) and suspended in 10 ml organ baths containing modified Krebs' solution (mM; NaCl, 90; NaHCO$_3$, 45; KCl, 5; MgSO$_4$.7H$_2$O, 0.5; Na$_2$HPO$_4$.2H$_2$O, 1; CaCl$_2$, 2.25; glucose, 10; pH 7.4, gassed with 5% CO$_2$, 95% O$_2$ at 37° C.). The tracheal rings were attached to an isometric force transducer for the measurement of isometric tension.

The tissues were washed and a force of 1 g was applied to each tissue.

Protocol A: The rings were pre-contracted with methacholine (1 μM) and a cumulative (0.3 nM-3 μM) isoprenaline concentration effect curve constructed. The rings were washed and either Compound A (4 nM) or vehicle was added. The rings were then contracted with a second concentration of methacholine (1 μM). Once the contraction had reached a plateau cumulative concentration response curves to Compound C (0.1 nM-1 μM), Compound E (1 nM-1 μM) or Compound H (0.1 nM-1 μM) were constructed. Data were collected using the ADInstruments chart4 software, the maximum tension generated at each concentration of agonist was recorded and the response expressed as percentage relaxation (mean±s.e.mean). The data was fitted to a four parameter logistic and a potency value ($pEC_{50}$) generated (expressed as mean±s.e.mean).

Protocol B: A cumulative concentration effect curve to methacholine (3 nM-30 μM) was constructed and then the tissue was washed. Vehicle, Compound D (3 nM), Compound J (3 nM), Compound K (2 nM), or Compound M (1 nM), alone or in combination with 4 nM Compound A, were added to the tissue and allowed to equilibrate for 1 hr. A second extended cumulative concentration response curve to methacholine was constructed (3 nM-1 mM). Data were collected using the ADInstruments chart4 software, the maximum tension generated at each concentration of agonist was recorded and the results were expressed as percentage of the maximum response measured in the first curve. Then, $pEC_{50}$ values were calculated from the first (untreated) and second (compound treated) methacholine concentration response curves and an apparent $pA_2$ value, was calculated assuming a Schild plot slope of 1 (expressed as mean±s.e.mean).

The compounds tested are denoted by the letters used in Table 1 of Example 5 (e.g. N-cyclopropyl-3-fluoro-4-methyl-5-[3-[[1-[2-[2(methylamino)ethoxy]phenyl]cyclopropyl]amino]-2-oxo-pyrazin-1-yl]benzamide is Compound A)

Assessment of the combination of Compound C and Compound A: The $pEC_{50}$ value to Compound C was 8.0±0.05, the $pEC_{50}$ value of Compound C in the presence of Compound A (4 nM) was 8.0±0.07 (n=4; Table 18, FIG. 104).

Assessment of the combination of Compound E and Compound A: The $pEC_{50}$ value to Compound E was 7.8±0.08, the $pEC_{50}$ value of Compound E in the presence of Compound A (4 nM) was 7.7±0.10 (n=4; Table 18, FIG. 105).

Assessment of the combination of Compound H and Compound A: The $pEC_{50}$ value to Compound H was 9.2±0.03, the $pEC_{50}$ value of Compound H in the presence of Compound A (4 nM) was 9.2±0.10 (n=4; Table 18, FIG. 106).

Assessment of the combination of Compound D and Compound A: The $pA_2$ value of Compound D was 10.7±0.09, the $pA_2$ value of Compound D in the presence of Compound A (4 nM) was 10.5±0.07 (n=4; Table 19, FIG. 107).

Assessment of the combination of Compound J and Compound A: The $pA_2$ value of Compound J was 9.9±0.12, the $pA_2$ value of Compound J in the presence of Compound A (4 nM) was 10.1±0.10 (n=4; Table 19, FIG. 108).

Assessment of the combination of Compound K and Compound A: The $pA_2$ value of Compound K was 9.9±0.10, the $pA_2$ value of Compound K in the presence of Compound A (4 nM) was 9.9±0.15 (n=4; Table 19, FIG. 109).

Assessment of the combination of Compound M and Compound A: The $pA_2$ value of Compound M was 11.9±0.04, the $pA_2$ value of Compound M in the presence of Compound A (4 nM) was 12.0±0.08 (n=4; Table 19, FIG. 110).

TABLE 18

Potency ($pEC_{50}$) values for Compounds C, E and H alone and in the presence of Compound A (4 nM) in guinea pig trachea in vitro.

| Compound | $pEC_{50}$ value | $pEC_{50}$ in the presence of Compound A | n |
|---|---|---|---|
| C | 8.0 ± 0.05 | 8.0 ± 0.07 | 4 |
| E | 7.8 ± 0.08 | 7.7 ± 0.10 | 4 |
| H | 9.2 ± 0.03 | 9.2 ± 0.10 | 4 |

$pEC_{50}$ values expressed as mean ± s.e. mean

TABLE 19

Apparent pA2 values for Compounds D, J, K and M alone and in the presence of Compound A (4 nM) in guinea pig trachea in vitro.

| Compound | $pA_2$ value | $pA_2$ in the presence of Compound A | n |
|---|---|---|---|
| D | 10.7 ± 0.09 | 10.5 ± 0.07 | 4 |
| J | 9.9 ± 0.12 | 10.1 ± 0.10 | 4 |
| K | 9.9 ± 0.10 | 9.9 ± 0.15 | 4 |
| M | 11.9 ± 0.04 | 12.0 ± 0.08 | 4 |

$pA_2$ values expressed as mean ± s.e. mean

Example 7

Inhibition of Lipopolysacchamide (LPS)-Induced TNFα and IL-6 Production of Alveolar Macrophages from COPD Patients Bronchoscopy Bronchoscopies were performed after the patients had been sedated. The bronchoscope was wedged peripherally and 0.9% (wt/vol) warmed normal saline instilled into the bronchial tree. Retrieved broncho-alveolar lavage (BAL) fluid was kept on ice until cell isolation.

Isolation of Alveolar Macrophages

BAL fluid was filtered (100 μm filter) and centrifuged (400 g for 10 min) to collect total BAL cells. These cells were re-suspended in RPMI (Sigma-Aldrich, Poole, England) supplemented with 10% (v/v) foetal calf serum (Invitrogen, Paisley, Scotland), 2 mM L-glutamine (Invitrogen), 100 U/mL penicillin, 100 μg/mL streptomycin (Sigma-Aldrich) and 0.25 μg/mL amphoteracin B (Sigma-Aldrich). Viable cell count was assessed by Trypan Blue exclusion and then the suspension volume adjusted to yield a cell density of $1 \times 10^6$/mL. A 0.1 mL portion of this suspension was seeded into individual wells of 96-well culture plates, which were incubated for 2 hr in a humidified 5% $CO_2$ atmosphere at 37° C. Alveolar macrophages were isolated as the adherent cells, following a wash with pre-warmed, supplemented RPMI media to remove non-adherent cells. Culture plates containing adherent cells were left overnight in a standard incubator with humidified 5% $CO_2$ atmosphere at 37° C.

Assay of Compound Effect on Mediator Production by LPS-Stimulated Alveolar Macrophages After replacement of the supplemented RPMI, alveolar macrophages were pre-incubated for 2 hr with a range of concentrations of the p38 kinase inhibitor, Compound A, either alone or in the presence of a range of concentrations of the corticosteroid, Dexamethasone. The alveolar macrophages were then incubated for 24 hr with LPS (1 μg/mL), with some wells to define baseline production not receiving LPS. Culture plates were then briefly centrifuged (10 min at 400 g) and the culture supernatant collected for analysis by ELISA (R&D Systems) to quantify the amount of released TNFα and IL-6. All cell incubations were performed in a standard incubator with humidified 5% $CO_2$ atmosphere at 37° C.

The data for each donor were transformed to represent the percentage of mediator production in the absence of both Compound A and Dexamethasone, without subtraction of background production. The mean values and standard deviation of percentage inhibition for all donors was then used for combination analyses.

Data Analysis

Combination and Benefit indices were calculated by fitting the inhibition data to a model that is an extension of Berenbaum's combination index (Isobolographic, algebraic, and search methods in the analysis of multiagent synergy. Berenbaum M. C. J Amer Coll Toxicol 7:927-938, 1988), allowing for the calculation of a single combination index over a set of combination doses, as described (Using R For Flexible Modeling Of Pre-Clinical Combination Studies, Harbron, C. USER2009). Calculations were carried out by using the nls( ) curve-fitting function in the R statistical programming language, with normal approximations on the log-scale to generate confidence intervals and significance levels for the combination indices. Combination indices significantly lower than one are termed synergistic. The Benefit Index was calculated in the same manner as the combination index, but assuming that Compound A had no effect as a monotherapy. A value of the benefit index significantly lower than one represents a benefit of the combination over the monotherapy.

Inhibition data for production of TNFα and IL-6 are shown in FIG. 111, representing the averaged results with alveolar macrophages from either 3 (IL-6) or 4 (TNFα) donors. The calculated Combination and Benefit indices for each mediator are shown in Table 20.

TABLE 20

Combination and Benefit Indices (t) for Interaction of Compound A and Dexamethasone to inhibit LPS-stimulated IL-6 and TNFα from COPD Alveolar Macrophages

|  |  | τ | Lower Confidence Interval | Upper Confidence Interval | p-Value* |
|---|---|---|---|---|---|
| IL-6 | Combination Index | 0.296 | 0.0747 | 1.17 | 0.086 |
|  | Benefit Index | 0.057 | 0.0045 | 0.74 | 0.030 |
| TNFα | Combination Index | 0.457 | 0.1981 | 1.05 | 0.069 |
|  | Benefit Index | 0.012 | 0.0011 | 0.15 | 0.0006 |

*Significance of value of τ different from 1.

The invention claimed is:
1. A pharmaceutical product comprising:
N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide or a salt thereof, and budesonide.

* * * * *